(12) United States Patent
Tripp et al.

(10) Patent No.: US 11,122,832 B2
(45) Date of Patent: Sep. 21, 2021

(54) METHODS AND COMPOSITIONS TO IMPROVE WEIGHT LOSS AND CARDIOMETABOLIC HEALTH BEYOND DIET AND EXCERCISE

(71) Applicant: Nature's Sunshine Products, Inc., Lehi, UT (US)

(72) Inventors: Matthew L. Tripp, Saratoga Springs, UT (US); Clinton J. Dahlberg, Saratoga Springs, UT (US); John G. Babish, Brooktondale, NY (US); Joseph Lamb, Lehi, UT (US); Joseph J. Ou, Saratoga Springs, UT (US); Sarah Elison, Spanish Fork, UT (US); Wei Gao, Lehi, UT (US); Mohan Kaadige, Salt Lake City, UT (US); Holly Brabazon, Lehi, UT (US)

(73) Assignee: Nature's Sunshine Products, Inc., Lehi, UT (US)

(*) Notice: Subject to any disclaimer, the term of this patent is extended or adjusted under 35 U.S.C. 154(b) by 54 days.

(21) Appl. No.: 16/083,488

(22) PCT Filed: Mar. 6, 2017

(86) PCT No.: PCT/US2017/021007
§ 371 (c)(1),
(2) Date: Sep. 7, 2018

(87) PCT Pub. No.: WO2017/155898
PCT Pub. Date: Sep. 14, 2017

(65) Prior Publication Data
US 2019/0261669 A1  Aug. 29, 2019

Related U.S. Application Data

(60) Provisional application No. 62/441,089, filed on Dec. 30, 2016, provisional application No. 62/321,727, filed on Apr. 12, 2016, provisional application No. 62/304,783, filed on Mar. 7, 2016.

(51) Int. Cl.
| | |
|---|---|
| *A23L 33/135* | (2016.01) |
| *A23L 33/11* | (2016.01) |
| *A23L 33/115* | (2016.01) |
| *A23L 33/155* | (2016.01) |
| *A23L 33/105* | (2016.01) |
| *A23L 33/00* | (2016.01) |
| *A23C 9/13* | (2006.01) |

(Continued)

(52) U.S. Cl.
CPC .......... *A23L 33/135* (2016.08); *A23C 9/1307* (2013.01); *A23L 27/34* (2016.08); *A23L 33/105* (2016.08); *A23L 33/11* (2016.08); *A23L 33/115* (2016.08); *A23L 33/15* (2016.08); *A23L 33/155* (2016.08); *A23L 33/30* (2016.08); *A23V 2002/00* (2013.01); *A23V 2200/02* (2013.01); *A23V 2200/30* (2013.01); *A23V 2200/328* (2013.01); *A23V 2200/332* (2013.01); *A23V 2250/214* (2013.01); *A23V 2250/2112* (2013.01); *A23V 2250/2131* (2013.01); *A23V 2250/21166* (2013.01); *A23V 2250/702* (2013.01); *A23V 2250/704* (2013.01); *A23V 2250/708* (2013.01); *A23V 2250/71* (2013.01); *A23V 2250/712* (2013.01); *A23Y 2220/00* (2013.01); *A23Y 2240/00* (2013.01); *A23Y 2300/00* (2013.01)

(58) Field of Classification Search
CPC combination set(s) only.
See application file for complete search history.

(56) References Cited

U.S. PATENT DOCUMENTS

| | | | |
|---|---|---|---|
| 6,383,482 B1 | 5/2002 | Gorsek | |
| 8,968,804 B2* | 3/2015 | Pan | G09B 19/0092 |
| | | | 426/2 |
| 9,220,741 B2* | 12/2015 | Shirazi | A61K 31/522 |

(Continued)

FOREIGN PATENT DOCUMENTS

| | | |
|---|---|---|
| CN | 105194658 | 12/2015 |
| JP | H091997-95452 | 4/1997 |

(Continued)

OTHER PUBLICATIONS

Sanchez, M. et al., Br. J. Nutri 2014 vol. 111, pp. 1507-1519.*

(Continued)

*Primary Examiner* — Heidi Reese
(74) *Attorney, Agent, or Firm* — Thorpe North & Western, LLP; David W. Osborne

(57) ABSTRACT

A weight loss system is presented herein. In one embodiment, the weight loss system that accelerates weight loss in a subject eating a caloric restricted diet with a minimum daily protein intake of about 3 oz. and engaging in daily physical activity equivalent to about 5,000 steps per day is presented. The weight loss system can comprise an effective amount of: an antimicrobial component that includes berberine, *cinnamon* and curcumin; fish oil; a probiotic component that includes *Lactobacillus* spp., *Bifidobacterium* spp., and *Streptococcus* spp.; an antioxidant, phytochemical component that includes apple extract, grape extract, green tea extract, and olive extract; and a vitamin component that includes vitamins A, B, C, D, and E. The weight loss system can stimulate a weight loss of at least 3% more than if not administered to the subject. Further presented herein is a method of facilitating weight loss in a subject and a method of improving the health of a subject participating in a weight loss program.

38 Claims, 13 Drawing Sheets

(51) Int. Cl.
*A23L 33/15* (2016.01)
*A23L 27/30* (2016.01)

(56) References Cited

U.S. PATENT DOCUMENTS

| | | |
|---|---|---|
| 2006/0088643 A1 | 4/2006 | Fugal et al. |
| 2006/0280815 A1 | 12/2006 | Gardiner et al. |
| 2010/0215783 A1 | 8/2010 | Mcneary |
| 2012/0052137 A1 | 3/2012 | Shirazi et al. |
| 2014/0255370 A1 | 9/2014 | Schreuder et al. |
| 2014/0308248 A1 | 10/2014 | Giampapa |

FOREIGN PATENT DOCUMENTS

| | | |
|---|---|---|
| JP | H101998-33190 | 2/1998 |
| JP | 2004536136 | 12/2004 |
| JP | 2013541108 | 11/2013 |
| JP | 2014176385 | 9/2014 |
| JP | 2015520176 | 7/2015 |
| WO | WO 2007/088046 A2 | 8/2007 |
| WO | WO 2016/149424 A1 | 9/2016 |

OTHER PUBLICATIONS

Hord et al.; "Food Sources of Nitrates and Nitrites: The Physiologic Context for Potential Health Benefits." The American Journal of Clinical Nutrition; May 13, 2009; vol. 90, Issue 1; pp. 1-10.

Asahi Food & Healthcare.; "Weight Control Shakes." Mintel; Retrieved from www.gnpd.com, Database accession No. 1785877; XP055626129; May 31, 2012; 5 Pages.

European Search Report Application No. 17763844.2, dated Oct. 10, 2019, 11 Pages.

Iovate Health Sciences.; "Smart Weight Loss Starter Kit." Mintel; Retrieved from www.gnpd.com, database accession No. 583481; XP002750919; Aug. 2011; 4 Pages.

Living Fuel.; "Optimized Superfood Meal Replacement." Mintel; Retrieved from www.gnpd.com, Database Assession No. 10237526; Oct. 17, 2005; 4 Pages.

Thomson Scientific.; "XP-002794611." Database WPI Week 201414; AN 2014-B66814; Nov. 27, 2013; 3 Pages; Abstract.

* cited by examiner

METHODS AND COMPOSITIONS TO IMPROVE WEIGHT LOSS AND CARDIOMETABOLIC HEALTH BEYOND DIET AND EXCERCISE

RELATED APPLICATION DATA

This application claims the benefit of U.S. Provisional Application No. 62/304,783 filed on Mar. 7, 2016; U.S. Provisional App. No. 62/321,727 filed on Apr. 12, 2016; and U.S. Provisional App. No. 62/441,089 filed on Dec. 30, 2016, each of which is incorporated herein by reference.

BACKGROUND

Significant portions of individuals in developed countries are overweight or obese which puts the individual at an increased risk for health problems. In addition, being overweight or obese can affect an individual's lifestyle; including but not limited to, their physical ability to participate in certain activities, wardrobe choices, and/or the individual's self-impression.

BRIEF DESCRIPTION OF THE DRAWINGS

Features and advantages of the invention will be apparent from the detailed description that follows, and which taken in conjunction with the accompanying figures, together illustrate features of the invention. It is understood that the figures merely depict exemplary embodiments and are, therefore, not to be considered limiting in scope.

DETAILED DESCRIPTION

Figure 1:
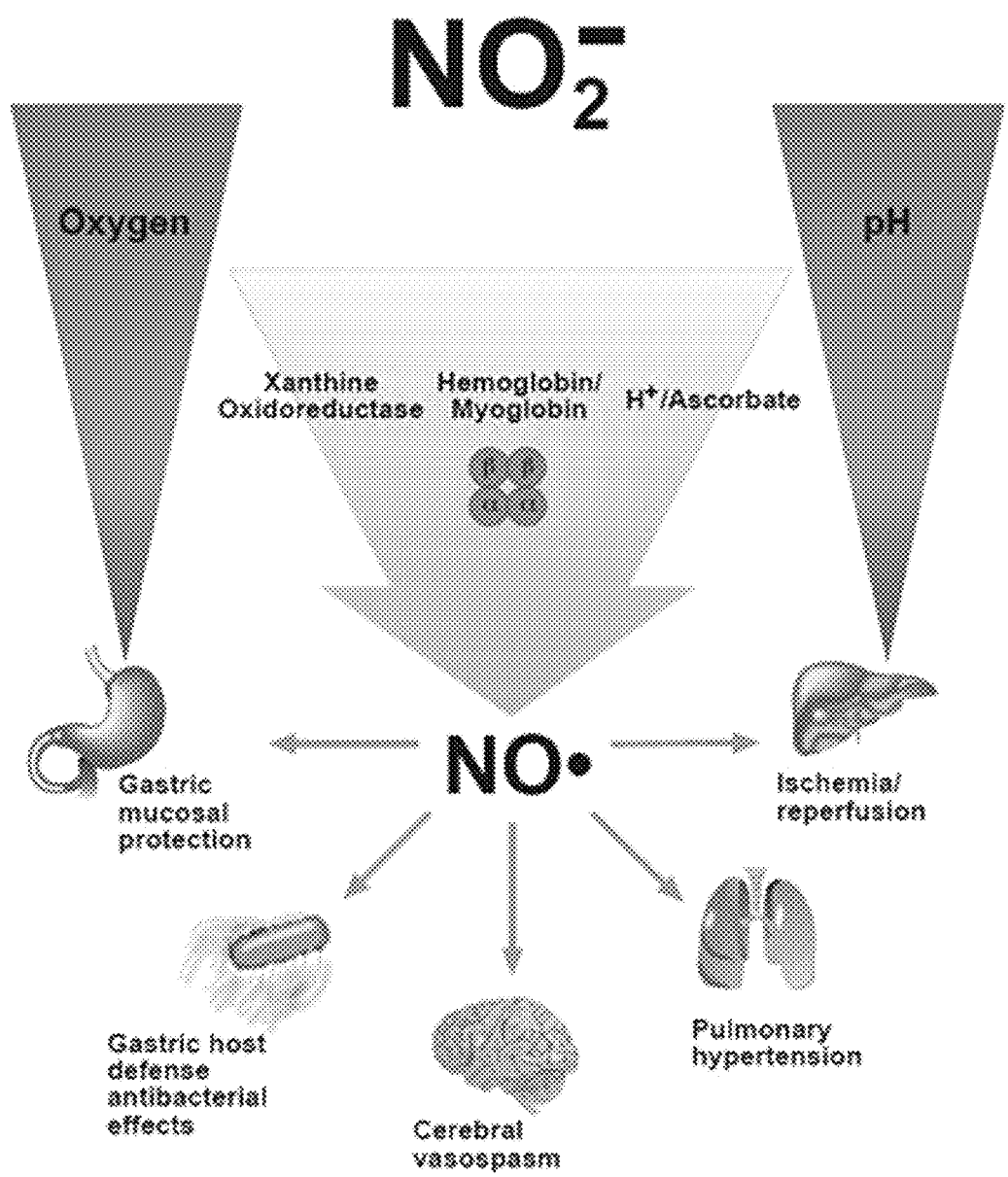
FIG. 1 is a schematic illustration of dual enzymatic and non-enzymatic pathways for nitric oxide production from nitrite.

Before invention embodiments are disclosed and described, it is to be understood that no limitation to the particular structures, process steps, or materials disclosed herein is intended, but also includes equivalents thereof as would be recognized by those ordinarily skilled in the relevant arts. It should also be understood that terminology employed herein is used to describe particular examples only and is not intended to be limiting. The same reference numerals in different drawings represent the same element. Numbers provided in flow charts and processes are provided for clarity in illustrating steps and operations and do not necessarily indicate a particular order or sequence. Unless defined otherwise, all technical and scientific terms used herein have the same meaning as commonly understood by one of ordinary skill in the art to which this disclosure belongs. In the specification and the appended claims, the singular forms include plural referents unless the context clearly dictates otherwise.

As used in this written description, the singular forms "a," "an," and "the" specifically also include express support for plural referents, unless the content clearly dictates otherwise. For example, "an excipient" provides support for one or more excipients.

The term "about" as used herein refers to a degree of deviation. It means approximately, in the region of, roughly, or around. When the term "about" is used in conjunction with a numerical value or range, it modifies that value or range by extending the boundaries a little above and below the numerical values set forth, for example 1, 2, 3, 4, or 5 numerical units above or below. It is understood that support in this specification for numerical values or other parameters used in connection with the term "about" is also provided for the exact numerical value or parameter itself as though "about" were not used.

Concentrations, amounts, and other numerical data may be expressed or presented herein in a range format. It is to be understood that such a range format is used merely for convenience and brevity and thus should be interpreted flexibly to include not only the numerical values explicitly recited as the limits or endpoints of the range, but also to include all the individual numerical values and/or sub-ranges encompassed within that range as if each numerical value (including fractions) and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 2.6, 3, 3.8, and 4 and sub-ranges such as from 1-3, from 2-4, and from 3-5, etc., as well as 1, 2, 3, 4, and 5, individually.

As used herein, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in the written description, like "comprising" or "including," it is understood that direct support should be afforded also to "consisting essentially of" language as well as "consisting of" language as if stated explicitly and vice versa.

As used herein, "bergamot" refers to bergamot orange (Citrus bergamia Risso), derivatives, and extracts thereof. This citrus species, grows abundantly in the Calabria region of southern Italy. Bergamot comprises two 3-hydroxymethylglutaryl (HMG) derivatives of naturally occurring flavonoid glycosides brutieridin and melitidin. These glycosides are the HMG derivatives of glucosylated hesperetin and naringenin, respectively, and have a structural similarity to the commercially available HMG-CoA reductase inhibitors known as the statins. In this application, bergamot can be used interchangeably herein to refer to the Citrus bergamia and/or an extract or derivative thereof unless the context clearly dictates otherwise.

As used herein a "concentrate" refers to dried powder, slurry or suspension derived from a component that does not include the use of any solvents during the concentration process.

As used herein "cardiometabolic-associated pathologies" or "cardiometabolic risk factors" refers to any disease or condition that increases the risk of those pathologies associated with cardiovascular dysfunction. This can result from a combination of decreasing the localized production of NO and increasing myeloperoxidase activity at the same site. Non-limiting examples of such diseases or conditions include without limitation, angina, arterial plaque buildup, deep vein thrombosis, dementia, diabetes (types, 1, 2 and 3), diabetic foot disorders, elevated glucose, insulin or HOMA score, elevated hs-CRP (levels greater than 1.0 pmol/L), elevated myeloperoxidase (levels greater than 350 pmol/L), endothelial dysfunction, erectile dysfunction, fibrinogen levels greater than 370 pmol/L, HDL modification, heart attack, heart failure, hypertension (BP greater than 140/90), lipoprotein-associated phospholipase A2 (LpPLA2 levels greater than 200 pmol/L), macular degeneration, monocyte-mediated arterial plaque formation, oxidation of LDL, periodontal disease, peripheral arterial disease, platelet stickiness, portal hypertension, pregnancy/pre-eclampsia, pulmonary hypertension, renal failure, serum low density lipoprotein (LDL) greater than 150 mg/dL, serum triglycerides greater than 150 mg/dL, sleep apnea, smooth muscle cell proliferation, stroke, and vasculitis.

The term "dosage unit" is understood to mean a unitary, i.e. a single dose which is capable of being administered to a subject or patient, and that may be readily handled and packed, remaining as a physically and chemically stable unit dose comprising either the active ingredient as such or a mixture of it with solid or liquid pharmaceutical vehicle materials. Dosages can be, but are not limited to oral, nasal, enteral, parenteral, transdermal, transmucosal, rectal, opthalmic, vaginal, etc.

The term "extract" refers to those substances prepared using a solvent, e.g., ethanol, water, steam, superheated water, methanol, hexane, chloroform liquid, liquid $CO_2$, liquid $N_2$, propane, supercritical $CO_2$, or any combination thereof. Extracts, as used herein, can refer to an extract in a liquid form, or can refer to a product obtained from further processing of the liquid form, such as a dried powder or other solid form. Extracts may take many forms including but not limited to: solid, liquid, particulate, chopped, distillate, etc. and may be performed by any number of procedures or protocols, such as chopping, grinding, pulverizing, boiling, steaming, soaking, steeping, infusing, applying a gas, etc., and may employ any suitable reagents, such as water, alcohol, steam, or other organic materials. Extracts typically have a given purity percentage and can be relatively to highly pure. In some embodiments, extracts can be phytoextracts made from specific parts of a source, such as the skin, pulp, leaves, flowers, fruits of a plant etc., or can be made from the whole source. In some aspects an extract may include one or more active fractions or active agents. In some extracts, maltodextrin can be added as a carrier. In some aspects, the purity of an extract can be controlled by, or be a function of the extraction process or protocol.

As used herein, "formulation" and "composition" can be used interchangeably and refer to a combination of at least two ingredients. In some embodiments, at least one ingredient may be an active agent or otherwise have properties that exert physiologic activity when administered to a subject.

As used herein, "linear inhibitory effect" or "dose-response" refers to a linear decrease in secretion or biosynthesis resulting from all concentrations of the inhibiting material over a dose-response curve. For example, inhibition at low concentrations followed by a failure of inhibition or increased secretion at higher concentrations represents a lack of a linear inhibitory effect.

As used herein, "more effectively" is used to describe relative biological responses elicited by compounds or formulations wherein the response elicited by one formulation is greater per unit of time (e.g. more rapidly) or per unit dose (e.g. mg/kg body weight).

As used herein, the term "meal replacement formulation" refers to a combination of nutritional ingredients assembled in an amount and variety sufficient to effectively provide the nutritional and caloric values of an otherwise desired meal. In one example the meal replacement formulation can be designed to provide a minimum of about 180 calories, 5 g. fat, 16 g. carbohydrate, 3 to 5 g. fiber, and 20 g. protein per serving as well as other optional compounds such as ascorbic acid, biotin, Chlorella spp., Chlorella vulgaris, chromium nicotinate, copper citrate, D-calcium pantothenate, cyanocobalamin, flax seed, Linum usitatissimum, folic acid, fructooligosaccharide (fiber), magnesium oxide, manganese citrate, maltodextrin, medium chain triglycerides, natural vanilla flavor, niacinamide, potassium citrate potassium iodide, riboflavin, sugar cane (*Saccharum officinarum*), sodium molybdate dihydrate, sodium selenate (selenium), soy protein isolate, *stevia* leaf extract/*Stevia rebaudiana*, thiamin HCl, tricalcium phosphate, vitamin a palmitate, vitamin D3, xanthan gum, zinc citrate, cellulose gum, guar gum, pyridoxine hydrochloride, salt, and vitamin E tocopherol.

As used herein, "pharmaceutically acceptable" refers generally to materials which are suitable for administration to a subject in connection with an active agent or ingredient. For example, a "pharmaceutically acceptable carrier" can be any substance or material that can be suitably combined with an active agent to provide a composition or formulation suitable for administration to a subject. Excipients, diluents, and other ingredients used in or used to prepare a formulation or composition for administration to a subject can be used with such term.

As used herein, "physical activity equivalent to at least 5,000 steps per day" refers to any physical activity performed by an individual that burns a number of calories that is approximately equivalent to a number of calories burned if that same individual were to walk at least 5,000 steps in one 24 hour period. As a general example, such an amount may be a minimum of 250 calories. Examples of physical activity can include without limitation, the jogging, dancing, cleaning, lifting weights, swimming, biking, hiking, climbing stairs, aerobic exercise, etc.

As used herein the term "primary therapeutic agent" designates the presence of a therapeutic agent in a composition at an amount greater than the total combined amount of the extracts providing a combined or synergistic effect in the composition.

The term "prevent" and its variants refer to prophylaxis against a particular undesirable physiological condition. The prophylaxis may be partial or complete. Partial prophylaxis may result in the delayed onset of a physiological condition. The person skilled in the art will recognize the desirability of delaying onset of a physiological condition, and will know to administer the compositions of the invention to subjects who are at risk for certain physiological conditions in order to delay the onset of those conditions. For example, the person skilled in the art will recognize that obese subjects are at elevated risk for conditions such as diabetes and coronary artery disease. Thus, the person skilled in the art can administer compositions to increase insulin sensitivity in an obese subject, whereby the onset of diabetes mellitus or dyslipemia may be prevented entirely or delayed.

The term, "subject," "subjects," "subjects in need thereof," and "individuals" includes humans as well as non-human subjects. It will be understood that the subject to which a compound of the invention is administered need not suffer from a specific traumatic state. Indeed, the compounds of the invention may be administered prophylactically. The terms "subject," "subjects," "subjects in need thereof," and "individuals" can be used interchangeably herein.

As used herein, "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent in a composition. Particularly, elements that are identified as being "substantially free of" are either completely absent from the composition, or are included only in amounts which are small enough so as to have no measurable effect on the composition.

As used herein, the term "solvent" refers to a liquid of gaseous, aqueous or organic nature possessing the necessary characteristics to extract solid material from a plant product. Examples of solvents would include, but not limited to, water, steam, superheated water, methanol, ethanol, ethyl acetate, hexane, chloroform, liquid $CO_2$, liquid $N_2$, propane, or any combinations of such materials.

The phrase "effective amount," "therapeutically effective amount," or "therapeutically effective rate(s)" of an active ingredient refers to a non-toxic, but sufficient amount or delivery rates of the active ingredient, to achieve therapeutic results in treating a disease or condition for which the ingredient is being delivered. It is understood that various biological factors may affect the ability of a substance to perform its intended task. Therefore, an "effective amount," "therapeutically effective amount, "or "therapeutically effective rate(s)" may be dependent in some instances on such biological factors. Further, while the achievement of" therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

The term "therapeutic," "therapeutically," and the like are used to encompass therapeutic, palliative, and/or prophylactic uses.

As used herein, "therapeutically effective time window" means the time interval wherein administration of the compounds of the invention to the subject in need thereof reduces or eliminates the deleterious effects or symptoms. In a preferred embodiment, the compound of the invention is administered proximate to the deleterious effects or symptoms.

The terms "treat," "treating," or "treatment" as used herein and as well understood in the art, mean an approach for obtaining beneficial or desired results, including without limitation clinical results in a subject being treated. Beneficial or desired results can include, but are not limited to, alleviation or amelioration of one or more signs or symptoms of a condition, diminishment of extent of disease, stabilizing (i.e. not worsening) the state of a disease or condition, delaying or slowing of disease progression, amelioration or palliation of the disease state, diminishment of the reoccurrence of disease, and remission (whether partial or total), whether detectable or undetectable. For example, where the physiological state is obesity, the term "treatment" refers to reducing the body fat mass, improving the body mass or improving the body fat ratio of a subject. "Treat," "treating," and "treatment" can also mean prolonging survival as compared to expected survival if not receiving treatment and can be prophylactic. Such prophylactic treatment can also be referred to as prevention or prophylaxis of a disease or condition. The prophylaxis may be partial or complete. Partial prophylaxis may result in the delayed onset of a physiological condition. The person skilled in the art will recognize that treatment may, but need not always, include remission or cure.

As use herein, "administering" a compound or agent to a subject refers to imparting the compound or agent to the subject in a way that provides the subject with a positive physiologic or health benefit as a result of the administration. A number of specific administration routes are known, such as oral, enteral, transdermal, transmucosal, parenteral, intravenous, and injectable administration.

As used herein, "co-administer," "co-administration," and "co-administering," refer to administering two or more active agents, compounds, extracts, supplements, etc. in a way that allows the active agents, compounds, extracts, supplements, etc. to have a concomitant or overlapping physiological effect on a subject. As such, co-administration includes both administration of multiple agents to a subject at the same time or within a time relative to one another that allows the physiologic or in-vivo effect or result of each agent to take place in a simultaneous or overlapping manner.

As used herein, "linear inhibitory effect" or "dose-response" refers to a linear decrease in secretion or biosynthesis resulting from all concentrations of the inhibiting material over a dose-response curve. For example, inhibition at low concentrations followed by a failure of inhibition or increased secretion at higher concentrations represents a lack of a linear inhibitory effect.

As used herein, "compounds" may be identified either by their chemical structure, chemical name, or common name. When the chemical structure, chemical name, or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form, and mixtures thereof. Accordingly, the chemical structures encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in un-solvated forms as well as solvated forms, including hydrated forms and as N-oxides. In general, compounds may be hydrated, solvated or N-oxides. Certain compounds may exist in multiple crystalline or amorphous forms. Also contemplated are congeners, analogs, hydrolysis products, metabolites, and precursor or prodrugs of the compound. In general, all physical forms are equivalent for the uses contemplated herein and are intended to be within the scope of the present disclosure.

Comparative terms such as "more effectively," "greater than," "improved," "enhanced," "increased," "decreased," and like terms can be used to state a result achieved or property present in a formulation or process that has a measurably better or more positive outcome than the thing to which comparison is made. For example, when referring to an improved health of a subject the comparison may be made to the health of the subject prior to engaging in the activity which improved the health of the subject. Moreover, such terms can be used to qualify a property of a component in a composition, a biological response, or a result that is measurably different from the same component when administered individually, a biological response that is markedly different from the expected biological response without the administration of a component or a composition, or a result that is measurably different from the results that occur using known methods. In one example, "increased or decreased concentration, secretion, or biosynthesis," means an appreciable or measurable increase or decrease in amount (e.g. by at least 3%), concentration, rate of secretion or amount of biosynthesis of the referent compound.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

In 2014 more than 1.9 billion adults, 18 years and older (38% of men and 40% of women) were overweight. Of these over 600 million were obese, this equates to about 13% of the world's adult population (11% of men and 15% of women). The worldwide prevalence of obesity is an increasing problem, which has more than doubled between 1980 and 2014. Obesity is prevalent amongst every income level and in high, middle, and low income countries. Sixty-five percent of the world's population lives in a country where more death occurs from an individual being overweight or obese than an individual being underweight.

Several diseases and conditions are attributable to weight. Globally, 44% of diabetes, 23% of ischemic heart disease, and between 7%-41% of certain cancers can be linked to and/or attributed to an inflicted individual being overweight or obese. Curbing the global obesity epidemic requires a population-based multi-sectoral, multi-disciplinary, and culturally relevant approach. Many claims have been made by many different individuals regarding the superiority of one diet or another for inducing weight loss. In 48 unique randomized trials (including 7,286 individuals) and compared with no diet, the largest weight loss was associated with low-carbohydrate diets (8.73 kg [95% confidence interval (hereinafter "CI"), 7.27 to 10.20 kg] at 6-month follow-up and 7.25 kg [95% CI, 5.33 to 9.25 kg] at 12-month follow-up) and low-fat diets (7.99 kg [95% CI, 6.01 to 9.92 kg] at 6-month follow-up and 7.27 kg [95% CI, 5.26 to 9.34 kg] at 12-month follow-up). It appears that weight loss differences among the studied diets were minimal.

Implementation of dietary supplementation programs for much of the population remains challenging and largely unsubstantiated. Individuals suffer from a lack of information regarding the safety, tolerance, and acceptability of both lifestyle medicine programs and nutritional supplementation programs. Clinical trials utilizing a protocol approved by the Copernicus Group IRB, have demonstrated the short-term benefits of a lifestyle modification program and additional benefits to be gained from appropriate nutritional supplementation. The consensus, however, remains that supplementation is not necessary to further weight loss in well-designed weight loss diet programs as diet vs. diet+supplementation yielded identical amounts of weight loss in the study.

Even though the healthy properties of functional foods and nutraceuticals still need to be fully elucidated, available data suggest that well-designed supplements, containing a ratio of omega-3 polyunsaturated fatty acids and antioxidants, specific probiotic strains, and selected polyphenols and prebiotics, could be useful in metabolic syndrome prevention and treatment. The gut microbiome seems to be the main target and player in the interactions occurring between probiotics, prebiotics, omega 3 polyunsaturated fatty acids, and polyphenols. Growth and metabolism of gut microflora can be managed with specific prebiotics and polyphenols. Without wishing to be limited to theory, the Applicant believes that probiotic bacteria may operate on three levels of host functionality to enhance gut microbioma and extra intestinal functions namely, (1) interfering with the growth of pathogenic bacteria in the lumen of the GUT via changing the microenvironment through production of secondary metabolites such as lactic, acetate, proprionate and butyrate; (2) strengthening the epithelial gut lining's barrier function and mucosal immunity as well as mucus production; and (3) effect the systemic immune system, as well as other cell and organ systems such as the liver. Despite this belief, the Applicant is unaware of a balance that has ever been clinically demonstrated with weight loss.

Nitric oxide (NO) is a free radical actively produced in the human body, and is the smallest signaling molecule known. NO exerts crucial roles in vascular and neuronal signal transduction, smooth muscle contractility, bioenergetics, improved gut barrier function, platelet adhesion and aggregation, immunity, and cell death regulation (FIG. 1; Table 1). Accumulated evidence suggests that a defective control of NO levels results in pathologies such as hypertension, cardiovascular dysfunctions, neuro-degeneration, arthritis, asthma, and septic shock.

One of the prevailing theories is that pulses of NO in the picomolar to low nanomolar range are by and large physiological; whereas, cell persistence at micromolar concentrations may become pathological. Evidence is growing that the dark side of NO, resides in its concentration levels, the production of peroxynitrite and other reactive oxygen and nitrogen species, the type of biomolecule reacting with the NO, and, when present, the cell bioenergetic changes that can be induced, which can strongly contribute to physiological or pathological outcomes (e.g. interactions with myeloperoxidase).

Figure 2:
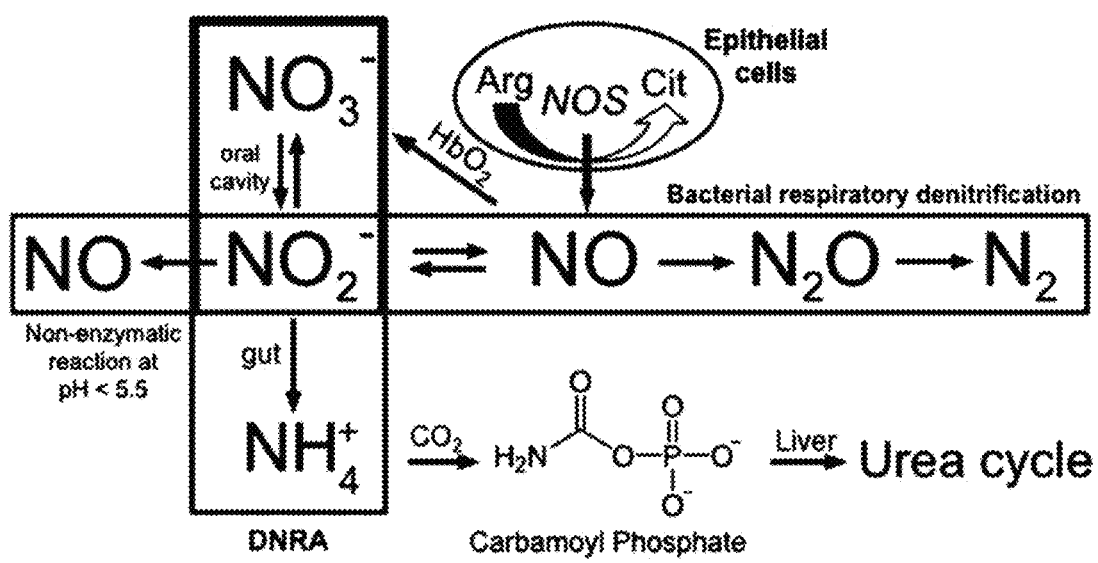
FIG. 2 is a schematic illustration of the nitrogen pathways in the human gut.

As depicted in FIG. 2, the amino acid L-arginine, dietary nitrate (NO3), and nitrite (NO2) can serve as sources for production of NO(x) (a diverse group of metabolites NO, nitrosothiols, and nitroalkenes). NO(x) production occurs via nitric oxide synthase enzymes (NOS), ultraviolet light exposure to skin, and mammalian nitrate/nitrite reductases in tissues, respectively. NO(x) are responsible for the hypotensive, anti-platelet, and cytoprotective effects of dietary nitrates and nitrites.

Enzymatically, NO is produced by nitric oxide synthases which utilize L-arginine and molecular oxygen as substrates and require the cofactors of reduced nicotinamide-adenine-dinucleotide phosphate (NADPH), flavin adenine dinucleotide (FAD), flavin mononucleotide (FMN), and (6R-)5,6,7,8-tetrahydrobiopterin (BH(4)). All of the isoforms of NOS can bind calmodulin and contain heme.

Neuronal NOS (nNOS, NOS I) is constitutively expressed in central and peripheral neurons, as well as, some other cell types. Its functions include synaptic plasticity in the central nervous system (CNS), central regulation of blood pressure, smooth muscle relaxation, and vasodilatation via peripheral nitrergic nerves. These nitrergic nerves are of particular importance in the relaxation of corpus cavernosum and penile erection. Phosphodiesterase 5 inhibitors (sildenafil, vardenafil, and tadalafil) require at least a residual nNOS activity for their action.

TABLE 1

Examples of Established Functions of Nitric Oxide in Physiological Systems

| System | Function |
|---|---|
| Cardiovascular | Controls vascular tone. |
| | Relaxes vascular smooth muscles and reduces blood pressure. |
| | Dilates vessels and relieves the pain of angina. |
| | Inhibits the aggregation of platelets within the vessels and prevents thrombotic events. |
| | Controls vascular tone. |
| | Relaxes vascular smooth muscles and reduces blood pressure. |
| | Dilates vessels and relieves the pain of angina. |
| | Inhibits the aggregation of platelets within the vessels and prevents thrombotic events. |
| Nervous | Acts as a neurotransmitter, including in the autonomic nervous system. |
| | Increases cerebral blood flow and oxygenation to the brain. |
| | Important mediator in penile erection during sexual arousal. |
| Pulmonary | Dilates pulmonary vessels. |
| | Benefits Adult Respiratory Distress Syndrome, pulmonary hypertension and Chronic Obstructive Airway Disease. |
| | Produced in abnormal amounts in inflammatory lung conditions. |
| | Concentration of NO in exhaled air can be taken as a marker of airway inflammation. |
| Gastrointestinal | Regulates the relaxation of smooth muscles. |
| | Controls peristalsis and the function of sphincters. |
| | Improve gut barrier function |
| | Gut microbiome supports increasing NO3 production |
| Renal | Increases blood flow to the kidney due to its vasodilatory effect,. |
| | Increases the glomerular filtration rate and the production of urine. |
| Immune | Modulates T cell-mediated immune response. |

Inducible NOS (iNOS, NOS II) is involved in immune responses, binds calmodulin and produces NO as an immune defense mechanism. Inducible NOS can be expressed in many cell types and can be expressed in response to lipopolysaccharide, cytokines, or other agents. iNOS generates large amounts of NO that have cytostatic effects on parasitic target cells. iNOS contributes to the pathophysiology of inflammatory diseases and septic shock.

Endothelial NOS (eNOS, NOS III) is mainly expressed in endothelial cells. Endothelial NOS keeps blood vessels dilated, controls blood pressure, and has numerous vasoprotective and anti-atherosclerotic effects. Pharmacologically, vascular oxidative stress can be reduced and eNOS functionality restored with renin- and angiotensin-converting enzyme-inhibitors, with angiotensin receptor blockers, and with statins. eNOS inhibitors such as asymmetric-dimethyl-L-arginine (ADMA) inhibit NO synthesis in vivo by competing with L-arginine at the active site of eNOS. In addition, eNOS possesses the ability to be "uncoupled" to produce superoxide anion instead of NO. Reduced NO bioavailability may play an essential role in cardiovascular pathologies and metabolic diseases. Cardiovascular risk factors can lead to oxidative stress, eNOS uncoupling, and endothelial dysfunction in the vasculature.

Endogenous synthesis is an important contributor to human's overall exposure to nitrate and ultimately production of NO. Once produced through NOS, NO has a half-life of approximately 1 second, can be quickly oxidized to nitrite and nitrate, or react with thiols or amines. Approximately 50% of the circulating levels of plasma nitrite reflect endogenous NO production, while steady-state levels of plasma nitrite and nitrate are determined primarily by diet. The bioavailability of dietary $NO_3$ is 100%. Following absorption, $NO_3$ may be reduced by facultative anaerobic bacteria on the dorsal surface of the tongue to nitrite, which can be chemically (low pH) and enzymatically (xanthine oxidoreductase, myoglobin, cytochrome P450, complexes of the mitochondrial electron transport chain) further reduced to NO. (See FIG. 1). It is not completely understood how NO is released from $NO_3$, and $NO_2$ at specific sites when needed.

Vegetables are the most abundant source of nitrates in the human diet; approximately 80% of dietary nitrates are derived from vegetable consumption; sources of nitrites include vegetables, fruit, and processed meats (See Table 2). Vegetables contribute more than 85% of the daily dietary intake of nitrate. The standard U.S. diet contains 50 mg to 120 mg nitrate while the standard Mediterranean Diet provides an estimated 400 mg nitrate per day.

Orally consumed $NO_3$ reaches a peak plasma concentration in approximately 1 hour; the half-life of plasma $NO_3$ is approximately 5-8 hours. Because $NO_3$ is a relatively small anion and is not protein bound, its pharmacokinetics and half-life suggest that it is reabsorbed in the renal tubules. $NO_3$ is excreted in the urine directly or after conversion to urea. Clearance of $NO_3$ from blood to urine is approximately 20 mL/min in adults indicating considerable renal tubular reabsorption of the ion. It is estimated that 96% of the filtered $NO_2$ and $NO_3$ is reabsorbed in the renal tubules.

Physiological concentrations of L-arginine in healthy individuals are sufficient to saturate eNOS, which occurs at approximately 3 μmol arginine/L. Supplementation, however, may be beneficial in special conditions such as malnutrition, excessive ammonia production, burns, infections, peritoneal dialysis, rapid growth, urea synthesis disorders, and/or sepsis. Since serum concentrations of L-arginine are normally in excess with respect to eNOS formation of NO, it is likely that there is no change in plasma concentration of $NO_2$ and $NO_3$ as a result of L-arginine supplementation. Acute L-arginine supplementation of 6 g does not increase plasma concentration of NOx over 120 minutes in healthy individuals with normal plasma concentrations of ADMA. Despite this, L-Arginine deficiency syndromes in humans involve dysregulation of system functions described in Table 1. L-arginine or L-citrulline supplementation may help treat individuals with atherosclerosis risk factors, such as hypercholesterolemia, hypertension, all forms of diabetes mellitus, kidney failure, hyperhomocysteinemia, smoking, and aging (See Table 1), all of which are conditions that are associated with reduced NO biosynthesis through eNOS.

TABLE 2

Nitrate Content of Selected Vegetables in Mediterranean Diet[†]

| Vegetable | Nitrate Content [mg/kg] |
|---|---|
| Beans | 400 |
| Beets | 1500 |
| Carrots | 170 |
| Eggplant | 460 |
| Fennel | 2,000 |
| Potatoes | 120 |
| Zucchini | 810 |

[†]Hord, N. G., et al. (2009). "Food sources of nitrates and nitrites: the physiologic context for potential health benefits." *Am. J. Clin. Nutr,* 90(1): 1-10.

In humans and other animals, dysregulation of NO is involved in the etiology of many diseases, such as Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, heart attack, heart failure, hypertension, immune deficiency, inflammatory bowel disease, leaky gut, macular degeneration, monocyte-mediated arterial plaque formation, motor dysfunction, multiple sclerosis, obesity, oxidation of LDL, periodontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, vasculitis, and diseases associated with skin such as slow wound healing, wrinkles, and premature signs of aging.

In one embodiment, a weight loss system is presented herein. An exemplary weight loss system can accelerate weight loss in a subject eating a caloric restricted diet with a minimum daily protein intake of about 3 oz. and engaging in daily physical activity equivalent to about 5,000 steps per day. In one example, the weight loss system can include an effective amount of an antimicrobial component that includes berberine, *cinnamon*, or curcumin or a combination thereof; fish oil; a probiotic component that includes *Lactobacillus* spp., *Bifidobacterium* spp., and *Streptococcus* spp.; an antioxidant phytochemical component that includes apple extract, grape extract, green tea extract, and olive extract; and a vitamin component that includes vitamins A, B, C, D, and E.

In one example, the caloric restricted diet can include a total daily caloric intake of from about 1,200 calories to about 2,200. In an additional example, the total daily caloric intake can be from about 1,200 to about 1,700 calories. In another example, the caloric restricted diet can include a total daily caloric intake from about 1,300 calories to about 1,450 calories. In yet another embodiment, the caloric restricted diet can include a total daily caloric intake of at least about 1,700 calories. In a further embodiment, the caloric restricted diet can comprise a total daily caloric intake of at least about 1,200 calories.

In some embodiments, the caloric restricted diet can be a high phytonutrient and protein rich diet. In other embodiments, the caloric restricted diet can be a low fat diet. In some examples, the caloric restricted diet can include limiting at least one of sugars, refined carbohydrates, and grains. In another example can include limiting at least two of sugars, refined carbohydrates, and grains. In yet another example, the caloric restricted diet can include limiting sugars, refined carbohydrates, and grains.

The caloric restricted diet can include multiple small meals per day. In one example, the caloric restricted diet can include 5 meals a day plus or including snacks. In another example, the caloric restricted diet can include 6 meals a day plus or including snacks.

The subject's daily protein intake can also vary. In some embodiments, the caloric restricted diet can include a minimum daily protein intake of about 6 oz. In another embodiment, the caloric restricted diet can include a minimum daily protein intake of about 9 oz. In a further embodiment, the caloric restricted diet can include a minimum daily protein intake of about 12 oz. In some embodiments, the protein can be consumed in increments or servings of about 3 oz. In some embodiments, multiple 3 oz. servings can be given at each meal and/or snack, for example, two 3 oz. servings for a total of 6 oz. per meal. In some embodiments, the caloric restricted diet can include a minimum daily protein intake of about 6 oz. to about 80 oz. of protein.

In some embodiments, the caloric restricted diet can include a set amount of servings from different food groups. In one example, the caloric restricted diet can include a daily vegetable intake of about 3 cups to about 6 cups of vegetables, a daily minimum fresh greens intake of 5 ounces, and a daily minimum fluid intake of 48 fluid ounces. In one embodiment, the caloric restricted diet can include a daily vegetable intake of 4 servings, a daily minimum fresh greens intake of 7 ounces, and a daily minimum fluid intake of 64 ounces. In another embodiment, the caloric restricted diet further include a single serving of fruit and/or legumes. In yet another embodiment, the caloric restricted diet can include a serving of dairy. In other embodiments, the caloric restricted diet can include a maximum of 5 total daily servings of oils and/or fats. Table 3 shows the different food groups and daily servings for one exemplary caloric restricted diet.

TABLE 3

Exemplary Caloric Restricted Diet

| Category | Total Daily Servings | Serving Size |
| --- | --- | --- |
| Meal Protein | 3 | Palm sized |
| Snack Protein | 2 | ½ palm size |
| Vegetables | 6 | ½ cup to 1 cup |
| Fresh Greens | 5 ounces | Varies |
| Fruit | 1 | Varies |
| Legumes | 1 | ½ cup (can replace fruit) |
| Dairy | 1 | Varies (can replace one snack protein) |
| Oils/Fats | 5 | Varies |
| Beverages | At least 6-8 | 8 fluid ounces |

The individual engaging in the weight loss system can be actively engaged in daily physical activity. In some examples, the daily physical activity can include the subject taking at least 5,000 steps per day or engaging in an activity that burns an equivalent amount of calories as the subject taking at least about 5,000 steps per day. In another example, the daily physical activity can include the subject engaging in an activity that burns an equivalent amount of calories the subject taking at least about 7,500 steps per day. In yet another example, the daily physical activity can include the subject engaging in an activity that burns an equivalent amount of calories the subject taking at least about 10,000 steps a day. The physical activity can be any activity that burns an equivalent amount of calories; whether it be, walking, running, lifting weights, hiking, dancing, playing sports, or any other multitude of physical activities, what matter is the extent of caloric expenditure, not the activity.

In some examples, the physical activity can comprise additional activities. In one example, the subject can engage in an activity or exercise activity that expends from about 115 calories to about 300 calories, 5 days a week. In another example, the subject can engage in an activity or exercise activity that expends from about 150 calories to about 500 calories at least 3 days a week. In yet another example, the subject can engage in an activity or exercise activity that expends from about 325 calories to about 600 calories at least 3 days a week. The physical activity can comprise aerobic activity, resistance training, strength training, and/or flexibility exercises.

Turning now to the weight loss system, in one example the weight loss system can include an effective or therapeutically effective amount of an antimicrobial component including berberine, *cinnamon*, curcumin, or a combination thereof; fish oil; a probiotic component including at least one of *Lactobacillus* spp., *Bifidobacterium* spp., *Bacillus* spp., and *Streptococcus* spp.; an antioxidant phytochemical component including apple extract, grape extract, green tea extract, and olive extract; and a vitamin component that includes vitamins A, B, C, D, and E. The antimicrobial component, fish oil, probiotic component, antioxidant phytochemical component and vitamin component can be combined in a single composition or can be multiple separate compositions.

The antimicrobial component can include berberine, *cinnamon*, curcumin, or a combination thereof. In one example, the berberine can be an extract from the Indian barberry root, *Berberis aristata*. In another example, the berberine can be an extract of Oregon grape (*Mahonia aquifolium*). In yet another example, the berberine can be an extract of Goldenseal (*Hydrastis canadensis*). In another embodiment, the berberine can be an extract of Chinese goldthread (*Coptis chinensis*). In a further embodiment, the berberine can be an extract of prickly poppy (*Argemone* spp). In some embodiments, the berberine extract can be an extract from two or more of Indian barberry root, Oregon grape, Goldenseal, Chinese goldthread, and prickly poppy. The extract can be derived from any part of these plants. In some embodiments, the extract can be derived from the root, rhizome, bark tissue, leaves, fruits or a combination thereof. In another example, the extract can be derived from the root, rhizome, bark tissue, or a combination thereof.

Consuming an effective amount of berberine can have benefits other than weight loss or a simple contribution thereto. In one example, the berberine can maintain healthy blood glucose levels when administered in an effective amount to a subject. In another example, the berberine can support healthy gut performance when administered in an effective amount to a subject. In yet another example, when administered the berberine can up-regulate enzymes that trigger blood glucose metabolism when administered in an effective amount to a subject. In a further embodiment, the berberine can combat endotoxins in the subject's gut, when administered in an effective amount to a subject. In yet another embodiment the berberine can reduce lipopolysaccharides levels in a subject when administered in an effective amount to a subject.

An effective amount of berberine can vary from subject to subject based on factors such as weight, age, and overall health. In one example, an effective daily dose of berberine can range from about 300 mg to about 1,500 mg. In another example, an effective daily dose of berberine can range from about 750 mg to about 1,250 mg. In yet another example, an effective daily of berberine can range from about 1,000 mg to about 1,300 mg. In a further example an effective daily dose of berberine can be about 999 mg.

*Cinnamon* (*Cinnamomum zeylanicum* and/or *Cinnamon cassia*) belongs to the Lauraceae family. Shoots from *cinnamon* tree stumps are cut and dried to produce one of the most important spices used daily by people all over the world. These dried shoots contain vital oils and other derivatives, such as cinnamaldehyde, cinnamic acid, and cinnamate. Beyond the three unique compounds listed, *cinnamon* also contains tannins, flavonoids, glycosides, terpenoids and anthraquinones. Cinnamon may exhibit antioxidant, anti-inflammatory, antidiabetic, antimicrobial, lipid-lowering, and cardiovascular-disease-lowering prosperities. Exemplary doses of cinnamon for positive health benefits, including such effects range from about 0.5 g to about 6.0 g daily, taken with meals.

Curcumin is a yellow pigment associated with the curry spice, turmeric (*Curcuma longa*), and to a far lesser extent ginger (*Zingiber officinale*). The putative bioactive molecules are thought to be the curcuminoids and commercial curcumin generally contains up to 95% pure curcuminoids. These molecules have potent anti-microbial as well as anti-inflammatory activity and can serve as a functional substitute for berberine or cinnamon at a dose of about 1,500 mg/day divided over two or three even doses (e.g. about 750 or 500 mg/dose, respectively).

As used herein curcumin can exist as simple ground turmeric or any modification of an extract of turmeric containing the putative bioactive curcuminoids. Such non-limiting modification would include nanoformulations, simple physical or chemical combinations with molecules designed to enhanced absorption and systemic distribution or limit metabolism and excretion.

In one example, the fish oil can comprise a component of oils derived from the tissues of fish. In one example, the fish oil can be derived from oils of mackerel, tuna, halibut, cod, salmon, sturgeon, mullet, bluefish, anchovy, sardines, herring, trout, menhaden, or any combination thereof. In another example, the fish oil can be derived from a combination of the tissues of anchovies, sardines, and mackerels. In a further example, the fish can be derived from cod. In yet another example, the fish oil can be derived from the liver of any of the fish previously mentioned. In some embodiments, fish oil can comprise the omega-3 fatty acids known as eicosapentaenoic acid (EPA) and docosahexaenoic acid (DHA). In one example, the fish oil can comprise a weight ratio of EPA to DHA of about 33:16. In other examples, the fish oil can comprise a weight ratio of EPA to DHA of about 1:1, 2:1, 3:1, 4:1, 1:2, 1:3, or about 1:4. In some embodiments, the fish oil can comprise lemon oil.

In some instances consuming fish oil can improve the health of the subject. In one example, taking an effective amount of fish oil can improve the cardiovascular heath of a subject. In another example, an effective amount of fish oil can protect cellular membranes. In yet another example, an effective amount of fish oil can benefit the strength and resiliency of an individual's skin.

An effective amount of fish oil can vary from subject to subject based on factors such as weight, age, and overall health. In general in one example, an effective daily dose of fish oil can comprise from about 1,000 mg to about 3,000 mg. In another example, an effective daily dose of fish oil can comprise from about 1,500 mg to about 2,500 mg. In yet another example, an effective daily dose of fish oil can comprise about 2,000 mg.

Turning to the probiotic component, in one example the probiotic component can comprise *Lactobacillus* spp., *Bifidobacterium* spp., and *Streptococcus* spp. In one embodiment, the probiotic component can be a blend. In one aspect, the *Lactobacillus* spp. can be selected from the group consisting of *L. rhamnosus, L. acidophilus, L. brevis, L. bulgaricus, L. plantarum, L. casei, L. salivarius*, and combinations thereof. In another example, the *Bifidobacterium* spp. can be selected from the group consisting of *B. bifidum, B. infantis, B. longum*, and combinations thereof. In yet another example, the *Streptococcus* spp. can be *Streptococcus thermophilus*. In a further example, the probiotic component can consist of 3 to 9 billion cfu of *Bacillus coagulans*. The probiotic component can comprise individual supplements of each of the species or a single composition. In some embodiments, the probiotic component can further comprise inulin, fructooligosaccharide, prebiotic fibers, and combinations thereof. In one example, the probiotic can comprise living cultures. In another example, the probiotic can comprise freeze-dried cultures.

The probiotic component can comprise different daily doses. In one example, the probiotic component can comprise a daily dose of about 30 billion to 40 billion colony forming units (cfu) of probiotic. In another example, the probiotic component can include a daily dose of about of about 15 billion to 25 billion cfu. In yet another example, the probiotic component can include a daily dose of about 35 billion to 45 billion cfus. In a further example, the probiotic component can include a daily dose of about 36 billion cfu. Consuming a probiotic can have additional benefits to the subject. In some instances, a daily dose of probiotics can regulate the microbiome of the users intestinal and digestive systems. In another example, consuming probiotics can help aid in the elimination of toxins from the body. In yet other examples, consuming probiotics can support healthy immune functions.

In one aspect, the antioxidant phytochemical component can comprise apple, grape, green tea, and olive extracts. In one example, the apple extract can comprise an extract derived from a member selected from the group consisting of *Malus domestica, Malus sieversii, Malus sylvestris, Malus pumila*, and combinations thereof. In one example, the apple extract can be derived from the species *Malus pumila*. In another example, the apple extract can be derived from a combination of *Malus domestica* and *Malus pumila*. In some embodiments, the apple extract can comprise any or all parts of the apple, including but not limited to the skin, flesh/fruit (exocarp, mesocarp, and/or endocarp), seed, stalk, stem, leaf, or a combination thereof. In one example, the apple extract comprises the skin and fruit of the apple. In some embodiments, the extract can be derived from immature apples. In one embodiment, an extraction solvent can be ethanol.

In one example, the grape extract can include a member selected from the group consisting of *Vitis vinifera, Vitis labrusca, Vitis riparia, Vitis rotundifolia, Vitis rupestris, Vitis aestivalis, Vitis mustangensis*, and combinations thereof. In one example, the grape extract can be derived from *Vitis vinifera*. In some embodiments, the grape extract can include any or all parts of the grape, including but not limited to, the skin, flesh/fruit, seed, vascular bundles, vine, leaves, or combinations thereof. In one embodiment, the grape extract can be derived from the seeds. In another embodiment, the grape extract can be derived from the skin. In yet another embodiment, the grape extract can be derived from the seeds and skin of the grape. In some embodiments, the grape extract comprises from about 75 wt % to about 95 wt % phenolics on a dry weight basis. In other embodiments, the grape extract can include from about 80 wt % to 97 wt % phenolics on a dry weight basis. In one example, the extraction solvent can be ethanol, water, or a mixture thereof.

In one example, the green tea extract can be derived from *Camellia sinensis*. In some embodiments, the green tea extract can comprise any or all parts of the tea including but not limited to the leaf, seed, stem, flower, or combination thereof. In one embodiment, the green tea extract can be derived from the leaves. In another example, the extract solvent can be water, ethanol, ethyl acetate, or combinations thereof.

In one example, the olive extract can include a subspecies of *Olea europea* selected from the group consisting of the subspecies *europea, cuspidiata, guanchica, cerasiformis, maroccana, laperrinei, cerasiformis*, or a combination thereof. In some embodiments, the olive extract can include any or all parts of the olive including but not limited to the leaf, seed, pulp, fruit, stem, or combinations thereof. In one embodiment, the olive extract can be derived from the leaves. In another example, the extraction solvent can be an ethanol and water solution.

In some embodiments, the plant or herb to extract ratio can range from about 1 to about 10. In other examples, the raw plant or herb to extract ratio can be from about 2 to about 5, from about 4 to about 7, or from about 8 to about 10. In one example, at least one of the extracts in the antioxidant phytochemical component can be present in a different amount than the other extracts. In another example, the extracts can all be present in the antioxidant phytochemical component at the same amount.

By way of example, in some embodiments, each extract can be present at a ratio of from about 1 to about 50 times the amount of another extract. In one aspect, the apple extract can be present in the formulation at a ratio of from 1 to 50 times the amount of a grape, green tea, or olive extract. In another aspect, the apple extract can be present in the formulation at a ratio of from about 1 to 25 times the amount of a grape, green tea, or olive extract. In a further aspect, the apple extract in the formulation can be present at a ratio of from 1 to 10 times the amount of a grape, green tea, or olive extract. In an additional aspect, the apple extract can be present in at a ratio of from 1 to 5 times the amount of a grape, green tea, or olive extract. In yet another aspect, the apple extract can be present in the formulation at a ratio of 1 times the amount of a grape, green tea, or olive extract. Any specific numerical value within the numerical range is included. In fact, each of the apple, grape, green tea, and olive extracts may be present in a ratio of anywhere between 1 to 50 times and 1 times the amount of the other extracts. For example, the amount of apple extract to grape extract to green tea extract to olive extract may in some embodiments be 1-25:1-25:1-25:1-25 respectively. In one example, the apple, grape, green tea, and olive extracts in the antioxidant phytochemical component can be present at a weight ratio of about 1:1:1:1. In another example, the apple, grape, green tea, and olive extracts in the antioxidant phytochemical component can be present at a weight ratio of about 6:1:3:1.

In some embodiments, the antioxidant phytochemical component can further include blueberry extract/concentrate, *capsicum* extract, and turmeric extract. In one example, the blueberry extract/concentrate can be obtained from *Vaccinium angustifolium*. In another example, the blueberry concentrate can be a dried powder created without the use of a solvent. In one embodiment, it can take about 5 kg, about 8 kg, about 10 kg, or about 12 kg of blueberries to obtain 1 kg of dried powder. In another embodiment, the *capsicum* extract can be obtained from *Capsicum annuum*. In some embodiments, *capsicum* extract can be derived from powdered dried ripe fruits. In one example, the turmeric extract can be obtained from *Curcuma longa*. In some embodiments, the turmeric extract can comprise an extract of the root, the rhizome, or a combination thereof. In another embodiment, the turmeric extract can be derived from a turmeric powder. In on embodiment, the turmeric powder can have from about 1 to about 10% curcuminoids, from about 3 to about 5% curcuminoids, from about 2% to about 8% curcuminoids, or from about 4% to about 12% curcuminoids. In some embodiments, the grape extract can comprise an extract of a grape skin and a grape seed extract.

In one embodiment, the antioxidant phytochemical composition can further include mangosteen extract, bergamot extract, or a combination thereof. The mangosteen extract can comprise a *Garcinia mangostana* extract and can be a fruit extract, a pericarp extract, or a combination thereof. In one embodiment, the mangosteen extract can be derived from *Garcinia mangosana*. The fruit extract can be derived from any part of the fruit, including but not limited to, the pulp, the rind, the seeds, or a combination thereof. In one embodiment, a mangosteen pericarp extract can be derived solely from the rind of the fruit. In one embodiment, the bergamot extract can be derived from Citrus bergamia Risso. In some examples, the antioxidant phytochemical composition can further comprise blueberry extract/concentrate, *capsicum* extract, turmeric extract, mangosteen extract, and bergamot extract.

The antioxidant phytochemical component can have a variety of mechanisms of action in addition to inducing weight loss. In one embodiment, the antioxidant phytochemical component can quench free radicals. In another embodiment, the antioxidant phytochemical component can modulate peroxynitrate formation. In one example, the antioxidant phytochemical component can modulate stress-signaling enzymes such as matrix metalloproteinases and myeloperoxidase. In yet another example, the antioxidant phytochemical component can be used for modulating oxidative stress in a mammal in need thereof. In some embodiments, the antioxidant phytochemical component can synergistically provide antioxidant support for gut microbiota and inhibition of peroxynitrite formation and gut inflammation.

The antioxidant phytochemical component can be administered at any effective dose. In one embodiment, the antioxidant phytochemical component can include a daily dose ranging from about 500 mg to about 1,000 mg. In another embodiment, the antioxidant phytochemical component can include a daily dose ranging from about 250 mg to about 750 mg. In yet another embodiment, the antioxidant phytochemical component can include a daily dose ranging from about 800 mg to about 1,200 mg. In one example, the antioxidant phytochemical component can be at a dose of about 750 mg. Turning now to the vitamin component, in one example the vitamin component can comprise vitamins A, B, C, D, and E. In one example, the B vitamins can be selected from the group consisting of Vitamin $B_1$, $B_2$, $B_6$, $B_{12}$, and combinations thereof. In some embodiments, the B vitamins can further include Vitamin $B_3$, $B_7$, $B_9$, or combinations thereof. In another example, the vitamin component can include vitamin $D_3$. In some embodiments, the vitamin component can further include vitamin K, calcium, iron, zinc, magnesium, chromium, panthenoic acid, biotin, and combinations thereof. In some examples, the vitamin component can be in a blend. In one example, the vitamin component can include individual vitamins at the daily recommended values established by the Food and Drug Administration (FDA). In another example, the vitamin component can include individual vitamins at more or less than the daily recommended values established by the FDA.

In one example, the weight loss system can include a phytosterol component in addition to the antimicrobial component, fish oil, probiotic component, antioxidant phytochemical component, and vitamin component. An effective daily dose of phytosterols can vary based on the subject; however, in one example, an effective daily dose of phytosterols can be about 4 g. In another example, an effective daily dose of phytosterols can be about 2 g. In yet another example, an effective daily dose of phytosterols can be about 6 g.

In some examples, the weight loss system can include additional ingredients/components. The additional ingredients/components can be found in any or all of the antimicrobial component, fish oil, probiotic component, antioxidant phytochemical component, and vitamin components when the antimicrobial component, fish oil, probiotic component, antioxidant phytochemical component, and vitamin component are separate supplements. In one example, the additional ingredients/components can include iron, docosahexaenoic acid (DHA), eicosapentaenoic acid (EPA), calcium, niacin, folic acid, biotin, panthothenic acid, phosphorus, iodine, magnesium, zinc, selenium, copper, manganese, chromium, potassium, inositol, p-Aminobenzoic acid (PABA), choline, bitartrate, lycopene, lutein, antioxidants, dandelion root, alfalfa aerial parts, asparagus stem, broccoli flowers, cabbage leaf, hesperidin bioflavonoid extract, lemon bioflavonoid extract, rutin, rose hips extract, chlorophyll, kelp leaf and stem, cranberry fruit, mangosteen fruit, carrot root, spinach leaf and stem, tomato fruit, acai berry, pomegranate fruit extract, I-leucine, I-lysine, I-valine, I-isoluecine, I-phenylanine, I-threonine, I-arginine, I-methionine, I-tyrosine, I-cysteine, and combinations thereof.

The amount of additional ingredients/components per unit serving are a matter of design and will depend upon the total number of unit servings of each of the antimicrobial component, fish oil probiotic component, antioxidant phytochemical component, and vitamin component administered to the subject. The total amount of additional ingredients/components can also depend in part, upon the health of the subject. In some embodiments, the additional ingredients/components can be chosen such that the additional ingredients/components do not exceed the FDA daily recommended values for the additional ingredients/components. In some examples, the amount of other ingredients/components can be a fraction or multiplier of the Reference Daily Allowance (RDA) or Reference Daily Intake (RDI) amounts.

The antimicrobial component, fish oil, probiotic component, antioxidant phytochemical component, vitamin component, and/or other ingredients/components can be administered in any suitable form. The antimicrobial component, fish oil, probiotic component, antioxidant phytochemical component, and vitamin components can include those suitable for oral, enteral, inhalation, rectal, ophthalmic (including intravitreal or intracameral), nasal, topical (including buccal and sublingual), vaginal, or parenteral (including subcutaneous, intramuscular, intravenous, intradermal, and intratracheal). In addition, the antimicrobial component, fish oil, probiotic component, antioxidant phytochemical component, vitamin component and/or other ingredients/components can be formulated as a depot preparation. Such long-acting compositions may be administered by implantation (e.g. subcutaneously, intra-abdominally, or intramuscularly) or by intramuscular injection. Thus, for example, the active ingredient may be formulated with suitable polymeric or hydrophobic materials (for example, as an emulsion in a pharmaceutically acceptable oil), or an ion exchange resin.

In one example, the antimicrobial component, fish oil, probiotic component, antioxidant phytochemical component, and/or vitamin component can be in oral formulations. In one example, the oral formulation can be in a capsule or tablet form. In another example, the oral formulation can be in the form of a liquid, capsule, powder, or a bar. In other examples an oral formulation can be formulated into a food or drink, and provided, for example, as a snack bar, a cereal, a drink, a gum, or in any other easily ingested form. In one embodiment, the nutritional supplement can be formulated into a nutritional beverage. Nutritional beverages can have consumer appeal, be easy to administer and incorporate into one's daily regimen. To manufacture the beverage, the ingredients are dried and made readily soluble in water. In some embodiments, the berberine, fish oil, probiotic component, antioxidant phytochemical component, and/or vitamin component can be in a topical formulation. In some examples, the topical formulation can be a cream, lotion, or a patch. One trained in the art can readily formulate the present composition into any of these convenient forms for oral or topical administration.

In some aspects the antimicrobial component, fish oil, probiotic component, antioxidant phytochemical component, vitamin component, and/or other ingredients/components can further include a pharmaceutically acceptable excipient. In one example, pharmaceutically acceptable excipients can be in the form of a coating, an isotonic and absorption delaying agent, a binder, an adhesive, a lubricant, a disintergrant, a coloring agent, a flavoring agent, a sweetening agent, an absorbent, a detergent, an emulsifying agent, a diluent, an excipient, and combinations thereof While the type of pharmaceutically acceptable carrier/vehicle employed in generating the compositions of the invention will vary depending upon the mode of administration of the composition to a mammal, generally pharmaceutically acceptable carriers are physiologically inert and non-toxic.

In some embodiments, the antimicrobial component, fish oil, probiotic component, antioxidant phytochemical component, vitamin component, and/or other ingredients/components can further include flavoring, coloring agent, spice, nut, and the like. Flavorings can be in the form of flavored extract, volatile oil, chocolate flavoring (e.g., non-caffeinated cocoa or chocolate, chocolate substitutes such as carob), peanut butter flavoring, cookie crumb, crisp rice, vanilla, or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch, or toffee. In one embodiment, the nutritional supplement can contain berry or other fruit flavor. The food compositions may further be coated, for example with a yogurt coating if it is as a bar.

An emulsifying agent/emulsifier can be added for stability of the final product. Examples of suitable emulsifying agents can include, but are not limited to, lecithin (e.g., from egg or soy), or mono- and di-glycerides. Other emulsifying agents are readily apparent to the skilled artisan and selection of suitable emulsifier(s) will depend, in part, upon the formulation and final product.

Preservatives can be added to the nutritional supplement to extend product shelf life. Exemplary preservatives can include potassium sorbate, sodium sorbate, potassium benzoate, sodium benzoate, or calcium disodium EDTA.

The nutritional supplement can further contain natural or artificial sweeteners, e.g., glucose, sucrose, fructose, saccharides, cyclamates, aspartamine, sucralose, aspartame, acesulfame K, or sorbitol.

In one example, the antimicrobial component, fish oil, probiotic component, antioxidant phytochemical component, vitamin component, and/or other ingredients/components are in a single formulation. In another example, the fish oil, probiotic component, antioxidant phytochemical component, vitamin component, and/or other ingredients/components are in multiple separate formulations. In some examples, some or all of the antimicrobial component, fish oil, probiotic component, antioxidant phytochemical component, vitamin component, and/or other ingredients/components can be combined in single formulation. When combined in a single formulation, the formulation can include any combination of the antimicrobial component, fish oil, probiotic component, antioxidant phytochemical component, vitamin component, and/or other ingredients/components.

In some embodiments, the antimicrobial component, fish oil, probiotic component, antioxidant phytochemical component, and vitamin component are in a co-formulation. A co-formulation is a single unit containing all active ingredients. A co-formulation can be a single powder in a container, or all actives in a pill, softgel or capsule. In some embodiments, the antimicrobial component, fish oil, probiotic component, antioxidant phytochemical component, vitamin component, and/or other ingredients/components are in the form of multiple formulations in a kit.

In some embodiments, the individual engaging in the weight loss system can replace one or multiple meals with a meal replacement component. In one example, the meal replacement component can include a protein supplement. In another example, the meal replacement component can be a weight loss shake. In one example, the meal replacement component can include about 20 g protein, from about 3 g to about 5 g fat, about 16 g carbohydrate, about 2 g of phytosterols, and about 180 calories. In another example, the meal replacement component can include about 20 g protein to about 60 g protein, from about 3 g to about 15 g fat, from about 32 g to about 96 g carbohydrate, from about 2 g to about 4 g of phytosterols, and from about 180 to about 540 calories. In yet another example, the meal replacement component can include about 40 g protein, from about 6 g to about 10 g fat, about 32 g carbohydrate, about 4 g of phytosterols, and about 360 calories. This is approximately a meal replacement amount, but can also be considered a snack.

In some examples, the individual engaging in the weight loss system can be further engaged in a cognitive behavioral program. The cognitive behavioral program can be any activity designed to change the cognitive processes of the user with respect to dieting, health, and/or exercise. In one example, the cognitive behavioral program can comprise a weekly seminar on mindfulness and teaching visualization techniques for stress reduction, relaxation, mind-body connectivity, and combinations thereof.

When administered in an individual engaging in a caloric restricted diet and daily physical activity the weight loss system can stimulate weight loss in excess of the weight loss resulting from the caloric restricted diet and daily physical activity. In one example, the weight loss system can stimulate weight loss of at least 3% more than if not administered to the subject. In another example, the weight loss system can stimulate weight loss of at least 4% more than if not administered to the subject. In yet another example, the weight loss system can stimulate weight loss of at least 5% more than if not administered to the subject. In some examples, the weight loss system can provide the subject with an amount of weight loss that is greater than an amount attributable to the additive effect of eating the caloric restricted diet, engaging in the daily physical activity, and administering the weight loss system.

Further presented herein, is a method of facilitating weight loss in a subject, including co-administering to the subject: an effective amount of the antimicrobial component; an effective amount of fish oil; an effective amount of a probiotic component that includes *Lactobacillus* spp., *Bifidobacterium* spp., *Bacillus* spp. and *Streptococcus* spp; an effective amount of an antioxidant phytochemical component that includes apple extract, grape extract, green tea extract, and olive extract; and an effective amount of a vitamin component that includes vitamins A, B, C, D, and E. The berberine, fish oil, probiotic component, antioxidant phytochemical component, and vitamin component can be as discussed above.

The antimicrobial component can be administered to the subject at a variety of doses. In some examples, the administered daily dose can be any of the daily doses discussed above. In one example, the berberine, cinnamon or curcumin can be administered to the subject at a daily dose ranging from about 300 mg to about 1,500 mg. In another example, the antimicrobial component can be administered to the subject at a daily dose of about 500 mg to about 1,000 mg. In yet another example, the antimicrobial component can be administered to the subject at a daily dose of about 750 mg to about 1,250 mg. In yet another example, the antimicrobial component can be administered to the subject at a daily dose of about 999 mg.

The quantity of daily doses of the antimicrobial component can vary based on the formulation. In one example, the antimicrobial component can be administered to the subject once a day. In another example, the antimicrobial component can be administered to the subject twice a day. In yet another example, the antimicrobial component can be administered to the subject three times a day. In some embodiments, the antimicrobial component can be administered with meals. In one embodiment, the antimicrobial component can be administered with breakfast, lunch, and dinner.

The administration of the fish oil component can also vary. The administered daily dose can be any of the daily doses discussed above. In one example, the fish oil can be administered to the subject at a daily dose of about 1,000 mg to about 2,000 mg. In another example, the fish oil component can be administered to the subject at a daily dose of about 1,250 mg to about 1,750 mg. In yet another example, the fish oil further comprises eicosapentaenoic acid (EPA) and docosahexaenoic acid (DHA) and the daily dose of the EPA administered to the subject can be about 760 mg and the daily dose of DHA administered to the subject can be about 380 mg.

The quantity of daily doses of the fish oil can vary based on the formulation. In one example, the fish oil can be administered to the subject once a day. In another example, the fish oil can be administered to the subject twice a day. In some embodiments, the fish oil can be administered in the morning and in the evening.

The administration of the probiotic component can be administered to the subject in a variety of doses. In some examples the administered daily dose can be any of the daily doses discussed above. In one example, the probiotic component can be administered to the subject at a daily dose of about 25 billion to about 50 billion colony forming units (cfu). In another example, the probiotic component can be administered to the subject at a daily dose of about 30 billion to about 40 billion cfu. In another example, the probiotic component can be administered to the subject at a daily dose of about 36 billion cfu.

The quantity of daily doses of the probiotic component can vary based on the formulation. In one example, the probiotic component can be administered to the subject once a day. In another example, the probiotic component can be administered to the subject twice a day. In some embodiments, the probiotic component can be administered to the subject three times a day.

The administration of the antioxidant phytochemical component can vary. The administered daily dose can be any of the daily doses discussed above. In one example, the antioxidant phytochemical component can be administered to the subject at a daily dose ranging from about 500 mg to about 1,000 mg. In another example, the antioxidant phytochemical component can be administered to the subject at a daily dose ranging from about 700 mg to about 900 mg. In yet another example, the antioxidant phytochemical component can be administered to the subject at a daily dose of about 750 mg.

The quantity of daily doses of the antioxidant phytochemical component can vary based on the formulation. In one example, the antioxidant phytochemical component can be administered to the subject once a day. In another example, the antioxidant phytochemical component can be administered in the morning. In yet another example, antioxidant phytochemical component can be administered in the evening. In a further example, the probiotic component can be administered to the subject twice a day. In some embodiments, the probiotic component can be administered to the subject three times a day.

The administration of the vitamin component can also vary. In some examples, the administered daily dose can be any of the daily doses discussed above. The quantity of daily doses of the vitamin component can vary based on the formulation. In one example, the vitamin component can be administered to the subject once a day. In another example, the vitamin component can be administered in the morning. In yet another example, the vitamin component can be administered in the evening. In a further example, the vitamin component can be administered to the subject twice a day.

In some examples, the co-administration of the antimicrobial component, fish oil, the probiotic component, antioxidant phytochemical component, and the vitamin component can be in a co-formulation.

In some embodiments, the method of facilitating weight loss in a subject can further include administering a meal replacement, or a snack formulation to the subject. In other embodiments, the method of facilitating weight loss in the subject can further include the subject participating in at least one of consuming a caloric restricted diet, engaging in moderate physical activity, engaging in a cognitive behavioral program, and combinations thereof. The meal replacement formulation, caloric restricted diet, moderate physical activity, and cognitive behavioral program can be as discussed above.

The method of facilitating weight loss in the subject can occur for a period of time. In one example, the method can occur for a period of at least 8 weeks. When the method occurs for a period of at least 8 weeks, the subject can experience an average weight reduction of about 5%. In another example, the method can occur for a period of at least 12 weeks. When the method occurs for a period of at least 12 weeks, the subject can experience an average of a 10% weight reduction in some examples and in other examples the subject can experience an average of about a 12% weight reduction after 12 weeks. In another embodiment, the subject can experience an average of an 8% weight reduction after 12 weeks. In yet another example, the method can occur for a period of at least 24 weeks. Regardless of the period of time administered, the longer the administration period, the greater the benefit. In one example, the subject can continue to experience a reduction in weight until an equilibrium is reached in which the subject consumes an amount equal to or greater than the calories the individual burns each day. In some examples, the method can provide the subject with an amount of weight loss that is greater than an amount of weight loss attributable to the additive effect of eating the caloric restricted diet, engaging in the daily physical activity, engaging in the cognitive behavioral program, and co-administering the berberine, fish oil, probiotic component, antioxidant phytochemical component, and vitamin component.

Also presented herein is a method of improving the health of a subject participating in a weight loss program. In one example, the method can include co-administering to the subject: an effective amount of an antimicrobial component; an effective amount of fish oil; an effective amount of a probiotic component that includes *Lactobacillus* spp., *Bifidobacterium* spp., *Bacillus* spp. and *Streptococcus* spp; an effective amount of an antioxidant phytochemical component that includes apple extract, grape extract, green tea extract, and olive extract; and an effective amount of a vitamin component that includes vitamins A, B, C, D, and E. The berberine, fish oil, probiotic component, antioxidant phytochemical component, and vitamin component can be as discussed above and can be administered in the doses and quantities discussed above.

In some embodiments, the method of improving health of a subject participating in a weight loss program can further comprise administering a meal replacement or snack formulation to the subject. In one example, the method can further include the subject subject participating in at least one of, consuming a caloric restricted diet, engaging in moderate physical activity, engaging in a cognitive behavioral program, and combinations thereof. The meal replacement formulation, caloric restricted diet, moderate physical activity, and cognitive behavioral program can be as discussed above. In one embodiment, the method of improving health of the subject can include the subject consuming a caloric restricted diet with a minimum daily protein intake of at least 9 oz. and engaging in daily physical activity equivalent to at least 5,000 steps per day.

The method of improving the health of a subject participating in a weight loss program can have a variety of health benefits. The improvement of health can be measured as determined by the health of the subject prior to participating in the weight loss program.

In some instances, the improvement in health can be an improvement in the subject's cardiovascular health. In one example, the subject can experience a reduction in blood pressure that is greater than a reduction attributable to the weight loss program alone. In one embodiment, the subject can experience about a 10% reduction in blood pressure after about four weeks of participating in the program. In another example, the subject can experience about an 11% reduction in blood pressure after about four to nine weeks of participating in the program. In yet another example, the subject can experience about a 12% reduction in blood pressure after about four to 13 weeks of participating in the program. The reduction in blood pressure can be to one or both of the subject's systolic and/or diastolic blood pressure.

In another example, the subject can experience an improvement in blood triglyceride and/or lipoprotein levels. In one example, the subject can experience a reduction in blood triglyceride levels that is greater than a reduction attributable to the weight loss program alone. In one embodiment, the subject can experience about a 50% reduction in blood triglyceride levels after 13 weeks of participating in the program. In another embodiment, the subject can experience about a 60% reduction in blood triglyceride levels after 13 weeks of participating in the program. In yet another example, the subject can experience a reduction in blood triglyceride high density lipoprotein (HDL) levels that is greater than a reduction attributable to the weight loss program alone. In one embodiment, the subject can experience about a 45% reduction in blood triglyceride levels after about nine to 13 weeks of participating in the program. In another embodiment, the subject can experience about an 80% improvement in blood triglyceride levels after 13 weeks of participating in the program.

In yet another example, the subject can experience a reduction in blood cholesterol levels. In one example, the subject can experience an improvement in total cholesterol levels. In one embodiment, the subject can experience a reduction in total cholesterol levels that is greater than a reduction attributable to the weight loss program alone. In one example, the subject can experience a reduction in total cholesterol levels of about 15% after about nine to 13 weeks of participating in the program. In another example, the subject can experience a reduction in total cholesterol levels of about 18% after about nine to 13 weeks of participating in the program. In yet another example, the subject can experience a reduction in total cholesterol levels of about 20% after about nine to 13 weeks of participating in the program. In other examples, the subject can experience a reduction in LDL cholesterol levels that is greater than a reduction attributable to the weight loss program alone. In one example, the subject's LDL cholesterol levels can reduce by about 15%, about 16%, about 17%, about 18%, about 19% or about 20% by engaging in the weight loss system for a period of about about nine to 13 weeks. In one embodiment, the subject can experience a reduction in HDL cholesterol levels that is greater than a reduction attributable to a weight loss program alone. In one example, the reduction in the subject's HDL cholesterol level can be about 15%, 16%, 17%, 18%, 19%, or about 20% after participating in the program for about nine to 13 weeks.

The subject can also experience a reduction in the subject's overall fat mass. In one example, the subject can experience a reduction in a mass of fat that is greater than a reduction attributable to the weight loss program alone. In one embodiment, the subject can experience about a 15% reduction in fat after 13 weeks of participating in the program. In another embodiment, the subject can experience about a 20% reduction in fat after 13 weeks of participating in the program. In yet another embodiment, the subject can experience about a 25% reduction in fat after 13 weeks of participating in the program. In one example, the reduction in the mass of fat can be a change in subject's visceral fat mass. In another example, the reduction in the individual's visceral fat mass can range from about 10 to about 14% following 13 weeks of participating in the program.

In some cases, the actual length of time to achieve the degree of change for a given health parameter stated herein is a function of the initial values for a given subject. Hypertensive subjects may respond with the stated degree of change in a shorter time than exemplified herein, while insensitive subjects may respond with the stated degree of change in a longer time than exemplified herein.

The subject can also experience an improvement in gut bacteria biome. In one example, the subject can experience a modification in gut bacteria biome that is greater than a modification attributable to the weight loss program alone. In one example, the subject can experience a reduction in nitrate gut levels that is greater than a reduction attributable to the weight loss program alone. In one example, the reduction in nitrate gut levels can occur by regulation of the nitric oxide pathway.

The subject can also experience a reduction in the subject's metabolic age. In one example the subject can experience a reduction of about 3 to 5 years after 2 weeks of participating in the program. In another example, the subject can experience a reduction in their metabolic age of between 7 to 10 years after 5 weeks of participating in the program. In yet another example, the subject can experience a reduction in their metabolic age of about 10 to 15 years after about 13 weeks of participating in the program. In one embodiment, the subject can experience a reduction in their metabolic age that averages about 13 years after participating in the program.

In a further example, the subjects can experience an improvement in systemic inflammation through a reduction in HsCRP (High sensitivity C-Reactive Protein) between 20 to 30% from their initial levels about in nine to 13 weeks.

The subject can also experience an improvement in other faucets of their overall health. In one example, the subject can experience improved function in at least one of the cardiovascular, nervous, pulmonary, gastrointestinal, renal, and immune system that is greater than a an improvement attributable to the weight loss program alone. In another example, the subject can experience a reduction in their body mass index.

In one embodiment, the method can be utilized in a subject that is suffering from a physical ailment. In one example, the subject can be suffering from or the subject can be prophylactically treating at least one of Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, coronary artery disease, heart attack, heart failure, hypertension, immune deficiency, inflammatory bowel disease, leaky gut, macular degeneration, monocyte-mediated arterial plaque formation, motor dysfunction, oxidation of LDL, peridontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, vasculitis and diseases associated with skin such as slow wound healing, wrinkles, and premature signs of aging.

In another embodiment, the method can occur in an individual at risk for or is currently obese. In one example, the co-administering the antimicrobial component, fish oil, probiotic component, antioxidant phytochemical component, and vitamin component; consuming the caloric restricted diet; engaging in the moderate physical activity; engaging in the cognitive behavioral program; and substituting at least one of breakfast, lunch, or dinner with the meal replacement formulation can prevent the onset of a metabolic disorder associated with obesity. In another example, the metabolic disorder associated with obesity can be a member selected from the group consisting of: Alzheimer's disease, Crohn's disease, diabetes (types, 1, 2 and 3), diminished exercise capacity, endothelial dysfunction, endotoxemia, inflammatory bowel disease, leaky gut, oxidation of LDL, and renal failure.

Embodiments

In one embodiment, a weight loss system that accelerates weight loss in a subject eating a caloric restricted diet with a minimum daily protein intake of about 3 oz. and engaging in daily physical activity equivalent to about 5,000 steps per day is presented. The weight loss system can comprise an effective amount of: the antimicrobial component; fish oil; a probiotic component that includes *Lactobacillus* spp., *Bifidobacterium* spp., *Streptococcus* spp., or *Bacillus* spp.; an antioxidant phytochemical component that includes apple extract, grape extract, green tea extract, and olive extract; and a vitamin component that includes vitamins A, B, C, D, and E. The weight loss system can stimulate a weight loss of at least 3% more than if not administered to the subject.

In one embodiment of the system, the caloric restricted diet can comprise a total daily caloric intake of from about 1,250 calories to about 1,700 calories.

In one embodiment of the system, the caloric restricted diet can comprise a total daily caloric intake of at least 1,350 calories.

In one embodiment of the system, the minimum daily protein intake can comprise 12 oz.

In one embodiment of the system, the caloric restricted diet can comprise: a daily vegetable intake of about 3 cups to about 6 cups of vegetables, a daily minimum fresh greens intake of 5 ounces, and a daily minimum fluid intake of 48 fluid ounces.

In one embodiment of the system, the caloric restricted diet can further comprise a daily intake of a single serving of fruit or legumes.

In one embodiment of the system, the daily physical activity can further comprise the subject engaging in an activity that expends from about 115 calories to about 300 calories 5 days a week.

In one embodiment of the system, the antimicrobial component can comprise an extract from the Indian barberry root, *Berberis aristata*, dried shoots of the cinnamon tree from the genus *Cinnamomum* or the curcuminoid fraction of turmeric (*Curcuma longa*).

In one embodiment of the system, the antimicrobial component can comprise a daily dose ranging from about 300 mg to about 1,500 mg.

In one embodiment of the system, the antimicrobial component can comprise a daily dose of about 1,000 mg.

In one embodiment of the system, the fish oil can comprise a component of oils derived from anchovies, sardines, and mackerels.

In one embodiment of the system, the fish oil can comprise a component of the oils derived only from the livers of fish, preferably cod.

In one embodiment of the system, the fish oil can comprise a daily dose of about 1,000 mg to about 3,000 mg.

In one embodiment of the system, the fish oil can comprise a daily dose of about 2,000 mg.

In one embodiment of the system, the probiotic component can comprise *Lactobacillus* spp. are selected from the group consisting of *L. rhamnosus, L. acidophilus, L. brevis, L. bulgaricus, L. plantarum, L. casei, L. salivarius*, and combinations thereof.

In one embodiment of the system, the probiotic component can comprise the *Bifidobacterium* spp. selected from the group consisting of *B. bifidum, B. infantis, B. longum*, and combinations thereof.

In one embodiment of the system, the probiotic component can comprise *Streptococcus thermophilus*.

In one embodiment of the system, the probiotic component can comprise *Bacillus coagulans*.

In one embodiment of the system, the probiotic component can further comprise a member selected from the group inulin, fructooligosaccharide, prebiotic fibers, and combinations thereof.

In one embodiment of the system, the probiotic component can comprise a daily dose of about 30 billion to 40 billion cfu of probiotic.

In one embodiment of the system, the probiotic component can comprise a daily dose of about 36 billion cfu of probiotic.

In one embodiment of the system, the apple, grape, green tea, and olive extracts in the antioxidant phytochemical component can be present at a weight ratio of about 1:1:1:1.

In one embodiment of the system, the apple, grape, green tea, and olive extracts in the antioxidant phytochemical component can be present at a weight ratio of about 6:1:3:1.

In one embodiment of the system, the antioxidant phytochemical component can further comprise blueberry concentrate, *capsicum* extract, and turmeric extract.

In one embodiment of the system, the antioxidant phytochemical component can further comprise mangosteen pericarp extract and bergamot extract.

In one embodiment of the system, the antioxidant phytochemical component can be at a daily dose ranging from about 500 mg to about 1,000 mg.

In one embodiment of the system, the antioxidant phytochemical component can be at a dose of about 750 mg.

In one embodiment of the system, the vitamin component can comprise B vitamins selected from the group consisting of Vitamin $B_1$, $B_2$, $B_6$, $B_{12}$, and combinations thereof.

In one embodiment of the system, the vitamin component can comprise vitamin $D_3$.

In one embodiment of the system, the system can further comprise a member selected from the group consisting of: iron, docosahexaenoic acid (DHA), eicosapentaenoic acid (EPA), calcium, niacin, folic acid, biotin, panthothenic acid, phosphorus, iodine, magnesium, zinc, selenium, copper, manganese, chromium, potassium, inositol, p-Aminobenzoic acid (PABA), choline, bitartrate, lycopene, lutein, antioxidants, dandelion root, alfalfa aerial parts, asparagus stem, broccoli flowers, cabbage leaf, hesperidin bioflavonoid extract, lemon bioflavonoid extract, rutin, rose hips extract, chlorophyll, kelp leaf and stem, cranberry fruit, mangosteen fruit, carrot root, spinach leaf and stem, tomato fruit, acai berry, pomegranate fruit extract, l-leucine, l-lysine, l-valine, l-isoluecine, l-phenyalanine, l-threonine, l-arginine, l-methionine, l-tyrosine, l-cysteine, and combinations thereof.

In one embodiment of the system, the system can further comprise an amount of a phytosterol.

In one embodiment of the system, the phytosterols can comprise a daily dose of about 4 g.

In one embodiment of the system, the caloric restricted diet can include a meal replacement component.

In one embodiment of the system, the meal replacement component can comprise about 20 g protein, from about 3 g to about 5 g fat, about 16 g carbohydrate, about 2 g of phytosterols, and about 180 calories.

In one embodiment of the system, the meal replacement/shake-snack component can comprise a daily dose of about 20 g to about 60 g protein, from about 3 g to about 15 g fat, from about 32 g to about 96 g carbohydrate, from about 2 g to about 4 g of phytosterols, and from about 180 to about 540 calories.

In one embodiment of the system, the meal replacement/shake-snake component can comprise a daily dose of about 40 g protein, from about 6 g to about 10 g fat, about 32 g carbohydrate, about 4 g of phytosterols, and about 360 calories.

In one embodiment of the system, the system can further comprise a cognitive behavioral program component.

In one embodiment of the system, the cognitive behavioral program can comprise a weekly seminar on mindfulness and teaching visualization techniques for stress reduction, relaxation, and mind-body connectivity.

In one embodiment of the system, the antimicrobial component, fish oil, probiotic component, antioxidant phytochemical component, and vitamin component can be in oral formulations.

In one embodiment of the system, the oral formulations can be in the form of a liquid, capsule, powder, or a bar.

In one embodiment of the system, the antimicrobial component, fish oil, probiotic component, antioxidant phytochemical component, and vitamin component can be in a single formulation.

In one embodiment of the system, the antimicrobial component, fish oil, probiotic component, antioxidant phytochemical component, and vitamin component can be in a co-formulation In one embodiment of the system, the system can provide the subject with an amount of weight loss that is greater than an amount attributable to the additive effect of eating the caloric restricted diet, engaging in the daily physical activity, and administering the weight loss system.

In one embodiment, a method of facilitating weight loss in a subject is presented. The method can comprise co-administering to the subject: an effective amount of and antimicrobial component that includes berberine, cinnamon, or a combination thereof; an effective amount of fish oil; an effective amount of a probiotic component that includes *Lactobacillus* spp., *Bifidobacterium* spp., *Streptococcus* spp; and *Bacillus* spp; an effective amount of an antioxidant phytochemical component that includes apple extract, grape extract, green tea extract, and olive extract; and an effective amount of a vitamin component that includes vitamins A, B, C, D, and E.

In one embodiment of the method, the antimicrobial component can be administered to the subject at a daily dose ranging from about 300 mg to about 1,500 mg.

In one embodiment of the method, the antimicrobial component can be administered to the subject at a daily dose of about 1,000 mg.

In one embodiment of the method, the antimicrobial component can be administered to the subject three times a day.

In one embodiment of the method, the antimicrobial component can be administered with breakfast, lunch, and dinner.

In one embodiment of the method, the fish oil can be administered to the subject at a daily dose of about 1,000 mg to about 2,000 mg.

In one embodiment of the method, the fish oil can further comprise eicosapentaenoic acid (EPA) and docosahexaenoic acid (DHA) and the daily dose of the EPA administered to the subject can be about 760 mg and the daily dose of DHA administered to the subject can be about 380 mg.

In one embodiment of the method, the fish oil can be administered to the subjected twice a day.

In one embodiment of the method, the probiotic component can be administered to the subject at a daily dose of about 30 billion to 40 billion cfu.

In one embodiment of the method, the probiotic component can be administered to the subject at a daily dose of about 36 billion cfu.

In one embodiment of the method, the probiotic component can be administered to the subject twice a day.

In one embodiment of the method, the antioxidant phytochemical component can be administered to the subject at a daily dose ranging from about 500 mg to about 1,000 mg.

In one embodiment of the method, the antioxidant phytochemical component can be administered to the subject at a daily dose of about 750 mg.

In one embodiment of the method, the antioxidant phytochemical component can be administered to the subject in the evening.

In one embodiment of the method, the vitamin component can be administered to the subject twice a day.

In one embodiment of the method, the antioxidant phytochemical component, the antimicrobial component, fish oil, the probiotic component, and the vitamin component can be administered in a co-formulation.

In one embodiment of the method, the method can further comprise administering a meal replacement/snack formulation to the subject.

In one embodiment of the method, the meal replacement/snack formulation can replace at least one of breakfast, lunch, and dinner.

In one embodiment of the method, the meal replacement/snack formulation can be administered to the subject at a daily dose of from about 20 g to about 60 g protein, from about 3 g to about 15 g fat, from about 32 g to about 96 g carbohydrate, from about 2 g to about 4 g of phytosterols, and from about 180 calories to about 540 calories.

In one embodiment of the method, the meal replacement/snack formulation can be administered to the subject at a daily dose of about 40 g protein, from about 6 g to about 10 g fat, about 32 g carbohydrate, about 4 g of phytosterols, and about 360 calories.

In one embodiment of the method, the method can further comprise the subject consuming a caloric restricted diet, engaging in moderate physical activity, and engaging in a cognitive behavioral program.

In one embodiment of the method, the caloric restricted diet can comprise a total daily caloric intake of from about 1,200 calories to about 2,000 calories.

In one embodiment of the method, the caloric restricted diet can comprise a total daily caloric intake of at least 1,350 calories.

In one embodiment of the method, the caloric restricted diet can comprise a minimum daily protein intake comprises 12 oz.

In one embodiment of the method, the caloric restricted diet can comprise: a daily vegetable intake of about 3 cups to about 6 cups of vegetables, a daily minimum fresh greens intake of 5 ounces, and a daily minimum fluid intake of 48 fluid ounces.

In one embodiment of the method, the caloric restricted diet can further comprise a daily intake of a single serving of fruit or legumes.

In one embodiment of the method, the method can further comprise the subject limiting at least one of sugars, refined carbohydrates, and grains in their caloric restricted diet.

In one embodiment of the method, the moderate physical activity can comprise the subject taking at least 5,000 steps per day or the equivalent of 5,000 steps per day.

In one embodiment of the method, the moderate physical activity can further comprise the subject engaging in an activity that expends from about 115 calories to about 300 calories 5 days a week.

In one embodiment of the method, the cognitive behavioral program can comprise a weekly seminar on mindfulness and teaching visualization techniques for stress reduction, relaxation, and mind-body connectivity.

In one embodiment of the method, the steps of administering the antioxidant phytochemical component, the antimicrobial component, the fish oil, the probiotic component, and the vitamin component to the subject can occurs for a period of at least 12 weeks.

In one embodiment of the method, 50% of the subjects can experience a 12% weight reduction after 12 weeks.

In one embodiment of the method, the method can provide the subject with an amount of weight loss that is greater than an amount of weight loss attributable to the additive effect of eating the caloric restricted diet, engaging in the daily physical activity, engaging in the cognitive behavioral program, and co-administering the antimicrobial component, fish oil, probiotic component, antioxidant phytochemical component, and vitamin component.

In one embodiment a method of improving the health of a subject participating in a weight loss program is presented. The method of improving health can comprise co-administering to the subject: an effective amount of the antimicrobial component; an effective amount of fish oil; an effective amount of a probiotic component that includes *Lactobacillus* spp., *Bifidobacterium* spp., *Streptococcus* spp., and *Bacillus* spp.; an effective amount of an antioxidant phytochemical component that includes apple extract, grape extract, green tea extract, and olive extract; and an effective amount of a vitamin component that includes vitamins A, B, C, D, and E.

In one embodiment of the method of improving health in the subject, the co-administering of the antimicrobial component, fish oil, probiotic component, antioxidant phytochemical component, and vitamin component to the subject can occur for a period of at least 12 weeks.

In one embodiment of the method of improving health in the subject, the weight loss program can include a caloric restricted diet with a minimum daily protein intake of at least 9 oz. and engaging in daily physical activity equivalent to at least 5,000 steps per day.

In one embodiment of the method of improving health in the subject, the subject can experience a reduction in blood pressure that is greater than a reduction attributable to the weight loss program alone.

In one embodiment of the method of improving health in the subject, the subject can experience a reduction in blood triglyceride levels that is greater than a reduction attributable to the weight loss program alone.

In one embodiment of the method of improving health in the subject, the subject can experience a reduction in LDL cholesterol levels that is greater than a reduction attributable to the weight loss program alone.

In one embodiment of the method of improving health in the subject, the subject can experience a reduction in total cholesterol levels that is greater than a reduction attributable to the weight loss program alone.

In one embodiment of the method of improving health in the subject, the subject can experience a reduction in a mass of fat that is greater than a reduction attributable to the weight loss program alone.

In one embodiment of the method of improving health in the subject, the reduction in the mass of fat is a change in visceral fat mass.

In one embodiment of the method of improving health in the subject, the subject can experience a modification in gut bacteria biome that is greater than a modification attributable to the weight loss program alone.

In one embodiment of the method of improving health in the subject, the subject can experience a modification in nitrate gut levels that is greater than the modification attributable to the weight loss program alone.

In one embodiment of the method of improving health in the subject, the modification in nitrate gut levels can occur by regulation of the nitric oxide pathway.

In one embodiment of the method of improving health in the subject, the subject can experience improved function in at least one of the cardiovascular, nervous, pulmonary, gastrointestinal, renal, and immune system that is greater than a an improvement attributable to the weight loss program alone.

In one embodiment of the method of improving health in the subject, the subject can be suffering from or can be prophylactically treating at least one of Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, coronary artery disease, heart attack, heart failure, hypertension, immune deficiency, inflammatory bowel disease, leaky gut, macular degeneration, monocyte-mediated arterial plaque formation, motor dysfunction, oxidation of LDL, periodontal disease, peripheral arterial disease, platelet stickiness, portal hypertension, pregnancy/preeclampsia, premature ejaculation, pulmonary hypertension, Raynaud's disease, renal failure, sleep apnea, smooth muscle cell proliferation, stroke, vasculitis and diseases associated with skin such as slow wound healing, wrinkles, and premature signs of aging.

In one embodiment of the method of improving health in the subject, co-administering the antimicrobial component, fish oil, probiotic component, antioxidant phytochemical component, and vitamin component; consuming the caloric restricted diet; engaging in the moderate physical activity; engaging in the cognitive behavioral program; and substituting at least one of breakfast, lunch, or dinner with the meal replacement formulation can prevent the onset of a metabolic disorder associated with obesity.

In one embodiment of the method of improving health in the subject, the metabolic disorder associated with obesity can be a member selected from the group consisting of: Alzheimer's disease, Crohn's disease, diabetes (types, 1, 2 and 3), diminished exercise capacity, endothelial dysfunction, endotoxemia, inflammatory bowel disease, leaky gut, oxidation of LDL, and renal failure.

EXAMPLES

Example 1

Evaluation of a Program (InForm1.1) for Healthy Weight and Cardiometabolic Function This trial was a randomized, two-arm, open-label study of diet and lifestyle modification (Arm A) against the same diet and lifestyle modification administered with a group of weight loss stimulating dietary supplements (Arm B) in generally healthy overweight subjects with cardiometabolic risk factors.

TABLE 4

Study Design Contrasting Arm A and Arm B in InForm1.1

| Activity | Details | |
|---|---|---|
| Recruiting and Screening | Recruit generally healthy, overweight and obese adults Measure waist, hip circumference, blood pressure, lipids and glucose. Randomize to an open-label, 2-arm study | |
| | Arm A | Arm B |
| Weeks 1-13 | High photonutrient protein rich food plan Physical activity Cognitive behavioral program | High photonutrient protein rich food plan Physical activity Cognitive behavioral program SNACK REPLACEMENT 40 g Protein 4 g Phytosterols 3 capsules Berberin-IR ® 2 capsules CardioxLDL ® (night) 2 capsules Probiotic 11 ® 2 softgels Super Omega-3 EPA ® 4 tablets Super Supplemental ® |

Volunteers were first screened to determine volunteer eligibility for study participation. Screening included a review and signing of the Screening Informed Consent form; measurement of height, weight, waist circumference and vital signs; completion of medical history questionnaire; review of medical history and current medications by clinician; and collection of fasting blood for testing of: Complete Blood Count (CBC), Comprehensive Metabolic Profile (CMP), standard lipid panel, insulin and hemoglobin A1c (HbA1c) as well as a pregnancy test in females of childbearing potential. Screening labs were performed within 8 weeks of beginning the trial. Fasting was defined as greater than 8 hours and less than 12 hours of refraining from consumption of food and beverages though unlimited consumption of water was allowed and encouraged. Upon review of screening data acceptable for inclusion, a telephone interview with a study investigator was completed to confirm eligibility, and document absence of contraindications to participation.

High Phyto-Nutrient Protein Rich Food Plan—

Both Arms A and B were provided with information on a specific food plan to be followed through the 12-week study. The plan promoted achieving health goals by counting servings of food and not calories. The food plan ensures that the required number of servings each day provide a balanced blend of protein, carbohydrates and fat and that the subjects received a diet packed with vitamins, minerals and nutrients from plants. The plan encompassed five meals and snacks daily along with limiting sugars, refined carbohydrates, and grains to provide an estimated 1,635 calories per day. See Table 5.

TABLE 5

Representative Diets† and Supplementation*
Followed in A and B Arms

| A | B |
|---|---|
| Breakfast | |
| Eggs (2 large) Peppers (0.5 cup) Olive oil (1 tsp) | Eggs (2) Peppers (0.5 cup) Olive oil (1 tsp) Super Supplemental ® (2 tablets); Super Omega 3 EPA ® (1 capsule containing 380 mg EPA, 190 mg DHA); Probiotic Eleven ® (1); Berberine IR ® (1 capsule 333 mg) |
| Snack | |
| Mixed greens (2.5 oz) Olive oil (1 tsp) Almonds (16) Olives (6) | Protein Supplement Shake (Soy, Pea, or Whey) Phytosterols (1 scoop 2 - g) Mixed greens (2.5 oz) Olive oil (1 tsp) |
| Lunch | |
| Chicken breast (1 palm size) Broccoli (2 cups) Olive oil (1 tsp) | Chicken breast (1 palm size) Broccoli (2 cups) Olive oil (1 tsp) Olives (6) Berberine IR ® (1 capsule 333 mg) |
| Snack | |
| 1 Chicken leg (1) Apple (1, small) | Protein Supplement Shake (Soy, Pea, or Whey) Phytosterols (1 scoop - 2 g) |
| Dinner | |
| Turkey breast (1 palm sized) Bok choy (1 cup) Carrots (0.5 cup) Mixed greens (2.5 oz) Olive oil (1 tsp) Cucumber (6 slices) Avocado (⅛) | Turkey breast (1 palm sized) Bok choy (1 cup) Carrots (0.5 cup) Mixed greens (2.5 oz) Olive oil (1 tsp) Cucumber (6 slices) Avocado (⅛) Super Supplemental ® (2 tablets); Super Omega 3 EPA ® (1 capsule containing 380 mg EPA, 190 mg DHA); Probiotic Eleven ® (1); Berberine IR ® (1 capsule 333 mg); CardioxLDL ® (2 capsules) |
| Beverages | |
| Water and Herbal teas: unlimited; coffee or tea (black, green, white): 1 cup caffeinated or decaffeinated | |
| Condiments/Sweeteners | |
| All fresh/dry herbs: dill, oregano, basil, lavender, tarragon, etc. All spices: cinnamon, chili powder, pepper, ginger, etc. Mustards, horseradish, lemon/lime juice, salsa, vinegars (all types) (unsweetened), soy sauce, fish sauce (unsweetened). Stevia. | |

†Vegetables could be eaten raw or steamed and dressed with one of their fats as primary cooking method.
*Shaded areas denote differences between arms.

Moderate Physical Activity—

All subjects received instruction and were required to follow the lifestyle change program consisting of the food plan (above) and exercise recommendations. The exercise requirements included (1) using a pedometer, (2) keeping a log of daily steps aiming for at least 5,000 steps per day (about 2.5 miles), with at least 30 minutes of moderate intensity focusing on aerobic movement exercising, and (3) adding resistance training and flexibility exercises at least twice a week.

Cognitive Behavioral Program—

All subjects were required to attend weekly, short seminars on mindfulness and visualization techniques designed for stress reduction, relaxation and mind-body connectivity.

TABLE 6

Snack Replacement and Weight Loss Stimulating Supplements for Arm B Only

|  | Daily Servings | Function |
|---|---|---|
| PROG Supplementation | | |
| Snack Replacement | 2 scoops 2x | Amino acids/antioxidants |
| Weight Loss Stimulating Supplements | | |
| Phytosterols | 1 scoop 2x | Biomatrix enrichment |
| Berberine IR | 3 capsules at dinner | Antimicrobial |
| CardioxLDL ® | 2 capsules/dinner | Antioxidant |
| Probiotic 11 | 1 capsule 2x | Repairing dysbiosis |
| Super Omega-3 EPA | 1 capsule 2x | Anti-inflammatory |
| Super Supplemental Vitamins & Minerals and Minerals | 2 tablets 2x | Biomatrix enrichment |

Phytosterols -The phytosterol supplement was manufactured by Nature's Sunshine Products in Spanish Fork, Utah and contained 2000 mg phytosterols per serving.
Berberine IR ® - The berberine IR supplement was manufactured by Nature's Sunshine Products in Spanish Fork, Utah. It contained: 333 mg berberine HCl. Subjects in Arm B were instructed to take 3 capsules per day at dinner (total = 1 g berberine)
CardioxLDL - The cardiox LDL supplement was manufactured by Nature's Sunshine Products in Spanish Fork, Utah. It contained: blueberry fruit concentrate, apple fruit extract, capsicum fruit, bergamot orange fruit extract, grape seed extract, grape skin extract, green tea leaf extract (decaffeinated), olive leaf extract, turmeric root & rhizome extract, and mangosteen pericarp extract. Subjects were instructed to take two capsules per day with a meal.
Probiotic 11 - The probiotic 11 supplement was manufactured by Nature's Sunshine Products in Spanish Fork, Utah. It contained: Bifidobacterium bifidum, B. infantis, B. longum, Lactobacillus rhamnosus, L. acidophilus, L. bulgaricus, L. brevis, L. plantarum, L. salivarius, L. casei, Streptococcus thermophiles, inulin, fructooligosaccharide, and prebiotic fibers. Subjects were instructed to take one capsule two times per day.
Super Omega-3 EPA - The super omega 3-EPA supplement was manufactured by Nature's Sunshine Products in Spanish Fork, Utah, it contained 360 mg eicosapentaenoic acid (EPA and 190 mg docosahexaenoic acid (DHA).
Super Supplemental Vitamins and Minerals- The super supplemental vitamin and mineral supplement was manufactured by Nature's Sunshine Products in Spanish Fork, Utah. It contained biotin, chromium amino acid chelate, copper gluconate, vitamin B12 (cyanocobalamin), cellulose, folic acid, magnesium amino acid chelate, manganese amino acid chelate, potassium iodide, vitamin B6 (pyridoxine hydrochloride), riboflavin (B2), selenium amino acid chelate, thiamin (B1) (thiamine mononitrate), vitamin A Palmitate, vitamin D3 (cholecalciferol), asparagus stem/Asparagus officinalis, acai berry/Euterpe oleracea, broccoli flowers/Brassica oleracea, carrot root/Daucus carota, cranberry fruit/Vaccinium macrocarpon, L-arginine, L-isoleucine, L-leucine, L-lysine, L-methionine, L-tyrosine, L-phenylalanine, L-threonine, L-valine, Pomegranate fruit extract/Punica granatum, fruit blend eight, spinach leaf & stem/Spinacia oleracea, tomato fruit Solanum lycopersicum, choline bitartrate, L-cysteine HCl [anhydrous], inositol, mangosteen fruit [freeze dried]/Garcinia mangostana, alfalfa aerial parts/Medicago sativa, cabbage leaf/Brassica oleracea var. capitata, kelp leaf & stem/Ascophyllum nodosum, Laminaria digitata, hesperidin bioflavonoid extract, cellulose, lemon bioflavonoid extract, magnesium stearate (vegetable), rose hips extract [4:1]/Rosa canina, rutin, dandelion root/Taraxacum officinale, lutein, cellulose [croscarmellose sodium, modified cellulose gum], dicalcium phosphate, vitamin C, beta-carotene, calcium amino acid chelate, pantothenic acid, calcium citrate, choline bitartrate, vitamin E (d-alpha tocopheryl acetate), ferrous fumarate, stearic acid (vegetable), inositol, lycopene, magnesium oxide, magnesium stearate (vegetable), niacinamide, para-aminobenzoic acid (PABA), potassium citrate, sodium copper chlorophyllin, silicon dioxide, and zinc gluconate.

High Protein, Low Glycemic Index Snack/Meal Formulation—

Subjects in Arm B substituted 2 snacks with a snack/meal replacement formulation (MR). The meal replacement formulation provides a minimum of 40 g protein, about 6 to 10 g fat, about 32 g carbohydrate, about 4 g of phytosterols and about 360 calories per day (Table 7) and contained the following ingredients: ascorbic acid, biotin, Chlorella/Chlorella vulgaris, chromium nicotinate, copper citrate, D-calcium pantothenate, cyanocobalamin, flax seed/Linum usitatissimum, folic acid, fructooligosaccharide (fiber), magnesium oxide, manganese citrate, maltodextrin, medium chain triglycerides, natural vanilla flavor, niacinamide, nondairy creamer (contains milk, soy), potassium citrate potassium iodide, riboflavin, sugar cane (Saccharum officinarum), sodium molybdate dihydrate, sodium selenate (selenium), stevia leaf extract/Stevia rebaudiana, thiamin HCl, tricalcium phosphate, vitamin a palmitate, vitamin D3, xanthan gum, zinc citrate, cellulose gum, guar gum, pyridoxine hydrochloride, salt, and vitamin E tocopherol.

TABLE 7

Snack/Meal Replacement Formulations (SR) Used in Arm B†

| Ingredient | SR1 | SR2 | SR3 | % Daily Value |
|---|---|---|---|---|
| Serving Size (g) | 46 | 45 | 45 | |
| Calories | 184 | 180 | 173 | |
| Fat (g) | 5 | 3 | 5 | |
| Saturated Fat (g) | 2 | 1 | 1 | |
| Trans Fat (g) | 0 | 0 | 0 | |
| Cholesterol (mg) | 32 | 0 | 0 | |
| Sodium (mg) | 104 | 150 | 307 | |
| Potassium (mg) | 368 | 95 | 187 | |
| Carbohydrate (g) | 14 | 16 | 16 | |
| Dietary Fiber (g) | 5 | 3 | 3 | |
| Sugars (g) | 5 | 9 | 8 | |
| Protein (g) | 20 | 20 | 20 | |
| Phytosterols (mg) | 2000 | 2000 | 2000 | * |
| Vitamin A (IU) | 48 | 75 | 47 | 35% |
| Vitamin C (mg) | 48 | 75 | 47 | 100% |
| Calcium (mg) | 96 | 2 | 33 | 60% |
| Iron (mg) | 0 | 0 | 0 | 20% |
| Vitamin A (IU) | 48 | 75 | 47 | 35% |
| Vitamin D (IU) | 0 | 75 | 47 | 10% |
| Vitamin E (IU) | 48 | 0 | 47 | 35% |
| Vitamin K (mcg) | 0 | 0 | 0 | |
| Thiamin (mg) | 48 | 75 | 47 | 50% |
| Riboflavin (mg) | 48 | 75 | 47 | 50% |
| Niacin (mg) | 48 | 75 | 47 | 50% |
| Vitamin B6 | 48 | 75 | 47 | 1250% |
| Folate (as folic acid and L-5-methyltetrahydrofolate) (mcg) | 104 | 75 | 47 | 100% |
| Vitamin B12 (as cyanocobalamin) (mcg) | 48 | 75 | 47 | 500% |
| Biotin (mcg) | 48 | 75 | 47 | 50% |
| Pantothenic Acid (mg) | 48 | 75 | 47 | 50% |
| Phosphorus (mg) | 48 | 0 | 20 | 55% |
| Iodine (mcg) | 0 | 75 | 47 | 50% |
| Magnesium (mg) | 72 | 0 | 33 | 60% |
| Zinc (mg) | 0 | 75 | 47 | 60% |
| Selenium (mcg) | 0 | 75 | 47 | |
| Copper (mg) | 0 | 75 | 47 | 50% |
| Manganese (mg) | 0 | 75 | 47 | 25% |
| Chromium (mcg) | 176 | 75 | 47 | 80% |
| Molybdenum | 0 | 75 | 0 | |
| Chloride (mg) | 0 | 0 | 0 | 10% |

†Taken twice per day; values in table represent single serving amounts and should be multiplied by two to determine total daily supplementation (e.g. calories per day = 368, 360 and 348, respectively).

Clinical Visits—

During the study subjects in both arms A and B participated in clinical visits. Clinical visits took place once weekly during the 13 weeks of the study. Three of the clinical visits were individual appointments and 11 visits were group appointments. The individual clinical visits were visits 1, 10, and 14. The focus of the individual visits was the collection of safety, tolerance and acceptability data, and individually focused lifestyle instruction and counseling. Group clinical visits were visits 2, 3, 4, 5, 6, 7, 8, 9, 11, 12, and 13. The focus of the group visits was group focused lifestyle instruction and counseling. Attendance at the 14 clinical visits was required. Total length of participation in the study, including screening (up to 8 weeks) and optional follow-up for Adverse Events (AE) (up to 4 weeks), was approximately 25 weeks.

Individual Clinical Visits (Visits 1, 10, and 14):

Subjects met with the study clinician. During the clinical visits, the study clinician reviewed questionnaires, assessed for signs and symptoms of adverse events, reviewed compliance to the study product and the dietary program and answered any questions from the subjects. Data collection (including physical measurements and phlebotomy for fasting laboratory assessments) was conducted at Visits 1, 10, and 14. Subjects received individual counseling and education pertinent to their assigned arm and the lifestyle change program at Visits 1 and 10.

Group Clinical Visits (Visits 2, 3, 4, 5, 6, 7, 8, 9, 11, 12, and 13):

Subjects met collectively with the study clinician in small groups. During these visits, study staff presented education and experiential content to support healthy lifestyle change. Data collection (limited to weight measurement) was conducted at Visits 2, 3, 4, 5, 6, 7, 8, 9, 11, 12, and 13.

All concomitant medications taken during study participation were recorded on the visit progress note. A prescription medication was defined as a medication that can be prescribed only by a properly authorized/licensed clinician. Medications to be reported were concomitant prescription medications, over-the-counter medications, medical foods, and nutritional supplements taken during the course of the study.

No concomitant prescription medications, over-the-counter medications, medical foods, and nutritional supplements were to be started or doses changed during the study unless they were prescribed by the PI (or the subject's primary care giver) for treatment of a specific clinical event. Acetaminophen, however, was allowed for mild headache or myalgia at a dose of 650 mg three times daily as needed.

Inclusion criteria included: (1) Men and women ≥18 and ≤65 years old; (2) Generally healthy yet meeting criteria; (3) Body Mass Index (BMI)≥28.5 kg/m2 and ≤42 kg/m2. (4) Visceral adiposity defined as a waist circumference ≥35 inches for women and ≥40 inches for men; and (5) Elevated LDLc≥130 mg/dl.

In addition, subjects must have exhibited one of the following criteria: (1) decreased high density lipoprotein cholesterol (HDLc) defined as HDLc<50 mg/dl for women and <40 mg/dl for men; (2) elevated TG defined as TG≥130 mg/dl; (3) increased blood glucose defined as blood glucose ≥100 mg/dl; (4) elevated HbA1c defined as HbA1C≥5.7%; (5) elevated Homeostatic Model Assessment of Insulin Resistance (HOMA) score defined as ≥2.0; and (6) ability to understand and the willingness to sign a written informed consent document.

Exclusion criteria included: (1) change in prescription medications, over-the-counter medications, medical foods, and nutritional supplements within 30 days prior to Day 1 and for the duration of the study; (2) use of medications classified as narcotics 15 days prior to Day 1 and for the duration of the study; (3) use of prescription medications and/or over-the-counter medications (Acetaminophen permitted) for acute and semi-acute medical conditions 15 days prior to Day 1 and for the duration of the study (use of acetaminophen was permitted on an as-needed basis); (4) use of an investigational drug or participation in an investigational study within 30 days prior to Day 1 and for the duration of the study; (5) use of oral or injectable corticosteroids within 30 days prior to Day 1 and for the duration of the study; (6) use of anticoagulant medications (heparin compounds, platelet inhibitors or warfarin) within 30 days prior to Day 1 and for the duration of the study (use of aspirin 81 mg or 325 mg once daily is permitted); (7) use of neuro-active prescription medications including major and atypical antipsychotic medications, anti-depressants, anti-anxiolytics, and epilepsy medications within 30 days prior to Day 1 and for the duration of the study; (8) use of prescription medications, over-the-counter medications, medical foods, and nutritional supplements for the treatment of hyperlipidemia within 30 days prior to Day 1 and for the duration of the study: and (9) use of prescription medications, over-the-counter medications, medical foods, and nutritional supplements for the treatment of hyperglycemia within 30 days prior to Day 1 and for the duration of the study.

Subjects were not allowed to discontinue prohibited prescription medications, over-the-counter medications, medical foods, and nutritional supplements to meet enrollment criteria.

Exclusionary criteria relating to medical history included: (1) a history of allergy or intolerance to study products; (2) clinically significant vital sign abnormalities (systolic blood pressure <90 mm Hg or >160 mm Hg, diastolic blood pressure <50 mm Hg or >100 mm Hg or resting heart rate of <50 or >100 bpm) at Screening; (3) a serious, unstable illness including cardiac, hepatic, renal, gastrointestinal, respiratory, endocrinologic, neurologic, immunologic, or hematologic disease; (4) known infection with HIV, TB or Hepatitis B or C; and (5) a current diagnosis or personal history of: (i) any cardiovascular disease including myocardial infarction, angina, cardiovascular surgery, congestive heart failure, cardiac arrhythmias or conduction abnormalities, cerebrovascular accident, transient ischemic attack (TIA), or peripheral vascular disease, deep vein thrombosis or pulmonary embolus; (ii) type 1 or type 2 Diabetes Mellitus; (iii) any autoimmune disease such as inflammatory bowel disease (including Crohn's Disease and/or ulcerative colitis), multiple sclerosis, rheumatoid arthritis, systemic lupus erythematosus, polymyositis, scleroderma and/or thyroiditis; (iv) any significant liver or kidney disease such as cirrhosis or non-alcoholic fatty liver disease, glomerulonephritis, and/or ongoing dialysis treatment; (v) any malignancy (with the exception of basal or squamous cell carcinoma of the skin if adequately treated and no recurrence for >5 years); (vi) any serious mental illness including a history of attempted suicide.

Exclusionary substance use included: (1) use of drugs of abuse (such as marijuana, cocaine, phencyclidine [PCP] and methamphetamine) 15 days prior to Day 1 and for the duration of the study; or (2) history of regular intake of >14 alcoholic drinks per week for females, and >21 drinks per week for males (1 drink=12 oz. beer, 4 oz. wine, or 1.0 oz. hard liquor).

Other exclusionary criteria included: (1) inability to comply with study and/or follow-up visits; (2) any concurrent condition (including clinically significant abnormalities in medical history, physical examination or laboratory evaluations) which, in the opinion of the PI, would preclude safe participation in this study or interfere with compliance; (3) any sound medical, psychiatric and/or social reason which, in the opinion of the PI, would preclude safe participation in this study or interfere with compliance; and (4) abnormal laboratory findings including: Abnormal blood counts (Hematocrit ≤33% or >47%; WBC<3.0 or >12.0×103/mm3; platelets <140 or >500×109/L); abnormal kidney function test(s) (BUN>30 mg/dL or creatinine >1.5 mg/dL) or liver function test(s) (AST, ALT)>3× the upper limit of normal; serum calcium (≥11 mg/dL); serum K≤3.5 mEq/L; Na≤134 or ≥148 mEq/L.

Subject Recruitment and Disposition—

Figure 3:
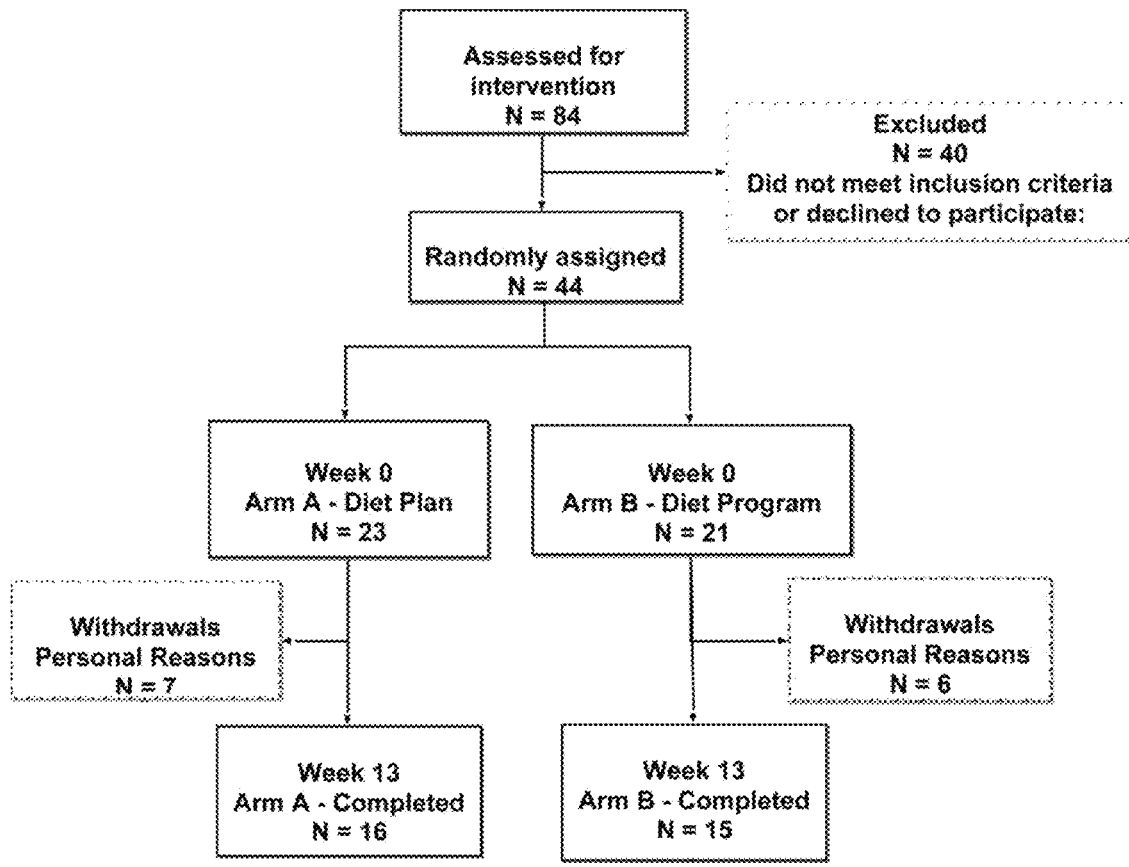
FIG. 3 is a schematic illustration of the subject selection and randomization into the InForm1.1 Diet (Arm A) and InForm1.1 Program (Arm B) in the open-labeled clinical trial conducted.

FIG. 3 graphically displays the subject selection and randomization into the DIET (Arm A) and PROG (Arm B) treatments.

Over the course of the study nitrite and nitrate levels were evaluated.

Assay of Nitrite in Saliva—

Salivary NO strips, which detect salivary $NO_2$ as a biomarker for NO, have been shown to be useful as a reliable indicator of physiological NO levels. Nitric Oxide Test Strips (Berkeley Test, Berkeley, Calif.) were used in this study to measure the appearance of the NO biomarker $NO_2$ in saliva. Subjects recorded morning, lunch and dinner strip scores one hour post meal-time once per week on the day of the clinical visit.

Assay of Nitrate in Plasma—

Nitrate/Nitrite (NOx) fluorometric assays were performed according to the manufacturer's instructions (Cayman Chemicals, Item No. 780051, Ann Arbor, Mich.). Plasma was filtered with 10 kDa MWCO VivaSpin 500 columns (Sartorius Stedim, VS0102). The microplate, with 10 μL of plasma per well, was incubated with nitrate reductase and cofactors at room temperature for 45 minutes before adding the 2,3-diaminonaphthalene (DAN) reagent. After a 10 minute incubation, 2.8 M sodium hydroxide was added and fluorescence was measured on a Cytation 5 plate reader (BioTek Instruments) with excitation and emission wavelengths of 375 and 417 nm, respectively.

Results Weight and Fat Loss—

Figure 4A:
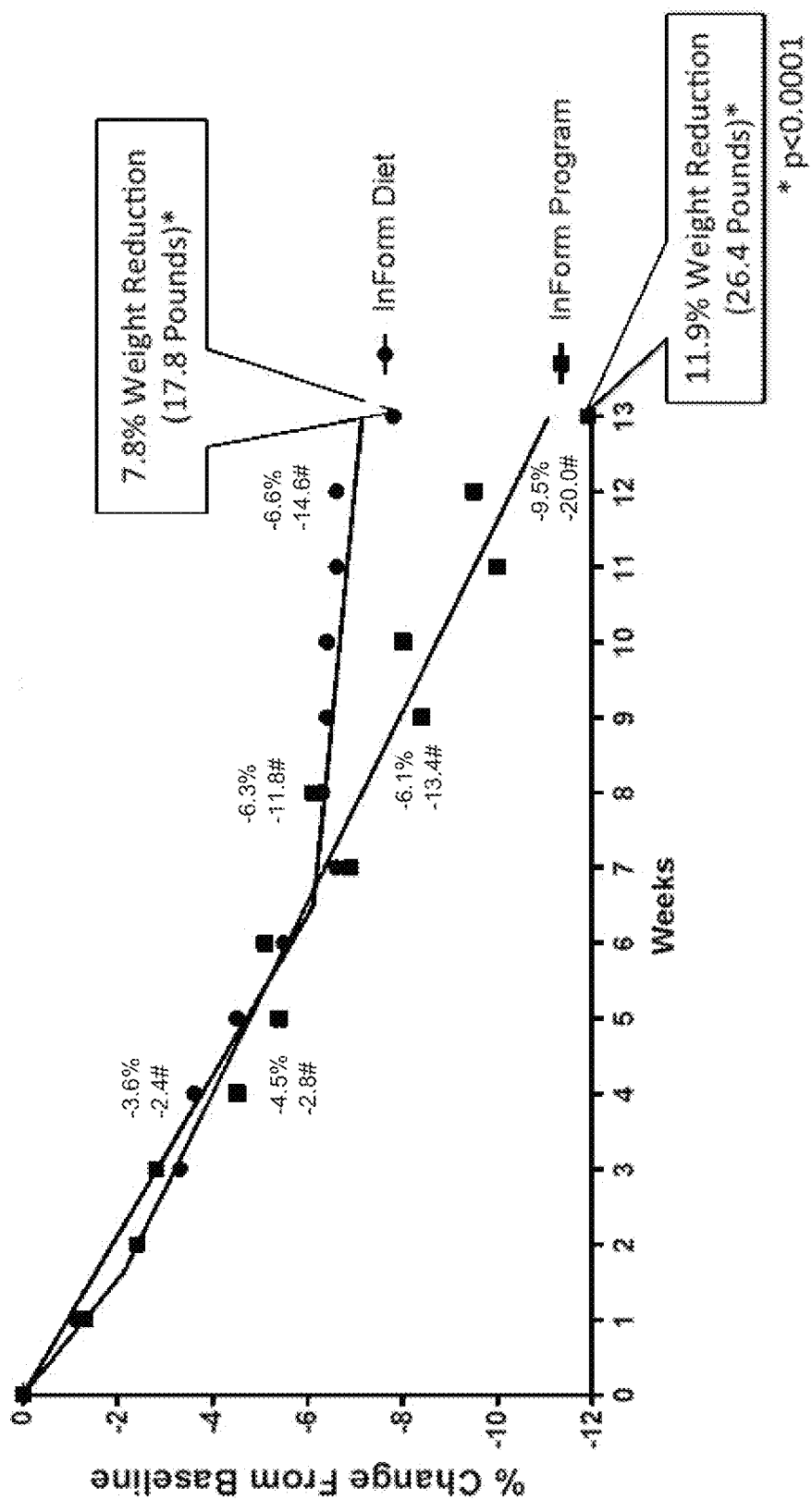
FIG. 4A graphically depicts the median percent change from baseline of weight loss of Arm A and Arm B subjects over the 13 weeks of the InForm1.1 clinical trial.
Figure 4B:
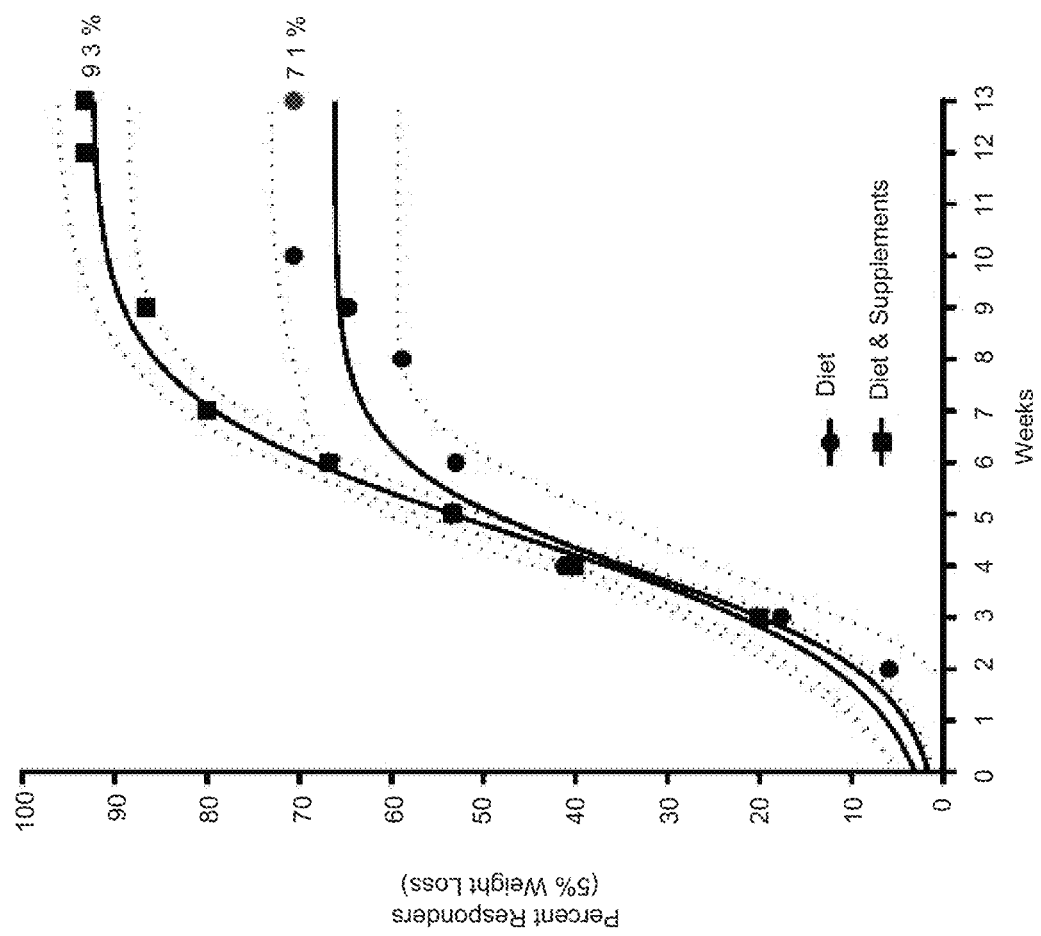
FIG. 4B graphically depicts the percent of Arm A and Arm B subjects that achieved a 5% reduction in weight over the 13 weeks of the InForm1.1 clinical trial.

Supplementation with the meal replacement formulation and weight loss stimulating dietary supplements, Arm B (InForm1.1 System) produced an 11.9% weight loss (26.4 pounds) versus a 7.8% weight loss (17.8 pounds) in the non-supplemented, Arm A, a 56% difference in result with p=0.0172. See FIG. 4A. Ninety-three percent of the supplement group achieved the benchmark 5% body weight loss over the study, while only 71% of the non-supplement group was able to attain the 5% level of weight reduction (p-0.05 for group difference). See FIG. 4B. Current treatment guidelines recommend that obese individuals lose 5% to 10% of their starting weights to minimize the risk factors for cardiovascular disease and reduce the risk for developing type 2 diabetes or hypertension. Globally, regulatory agencies set this 5% figure above placebo as absolute criteria for approval. Table 8 illustrates the superior performance of the InForm1.1 Program (Arm B) relative to weight loss drugs in achieving the 5% weight loss response among subjects.

TABLE 8

Contrasting Percent Responders for Program, Diet and Prescription Products

| Test Material | Evaluation | Responders |
|---|---|---|
| Arm A - InForm Diet | 8 weeks | 59% |
| Arm B - InForm System | 8 weeks | 80% |
| Placebo† | 8 weeks | 8% |
| Bupropion (400 mg) | 8 weeks | 48% |
| Placebo†† | 12 weeks | 12% |
| Lorcaserin BID (10 mg) | 12 weeks | 36% |
| Arm A - InForm Diet | 12 weeks | 71% |
| Arm B - InForm System | 12 weeks | 93% |

Further, the number of subjects achieving either a 5% or 10% weight loss was substantially better for the Arm B versus prescription drugs. See Table 9. With 93% of the subjects exhibiting a 5% or greater weight loss during the trial period, the InForm1.1 System (Arm B) was 55% better than the next best performing agent liraglutide at 60% and 121% better than orlistat at 42%. Arm B showed even greater benefits versus prescription drugs when the number of subjects achieving a 10% or greater weight loss was considered; the InForm1.1 System was 300% better than orlistat and 94% better than liraglutide.

TABLE 9

Five and Ten Percent Responders for Program and Three Prescription Products

| Test Material | Period | ≥5% | ≥10% |
|---|---|---|---|
| Placebo | 56 weeks | 23% | 9% |
| Orlistat (Alli ®) | 24 weeks | 42% | 15% |
| Lorcaserin (Belviq ®) | 56 weeks | 47% | 22% |
| Liraglutide (Victoza ®) | 56 weeks | 60% | 31% |
| Arm B - InForm1.1 System | 12 weeks | 93% | 60% |

Figure 5:
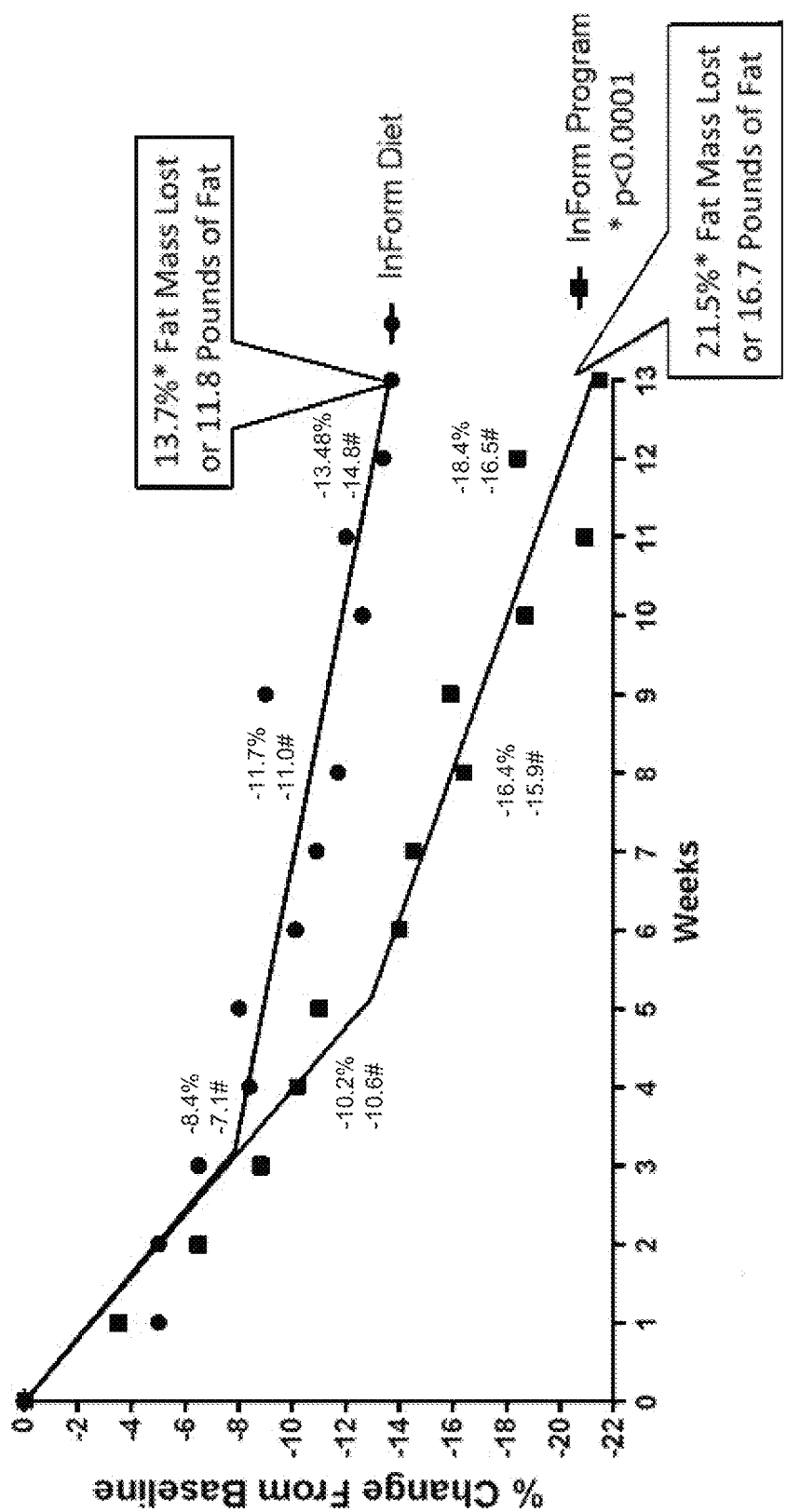
FIG. 5 graphically depicts the median percent change from baseline of fat mass loss of Arm A and Arm B subjects over the 13 weeks of the InForm1.1 clinical trial.

Similarly, the InForm1.1 System, Arm B, experienced a median 21.5% (16.7 pounds) fat mass loss over the study compared with a median 13.7% (11.8 pounds) for the non-supplemented group, Arm A, with p<0.0001. (See FIG. 5).

Results Nitric Oxide Biomarker Levels—

Figure 6:
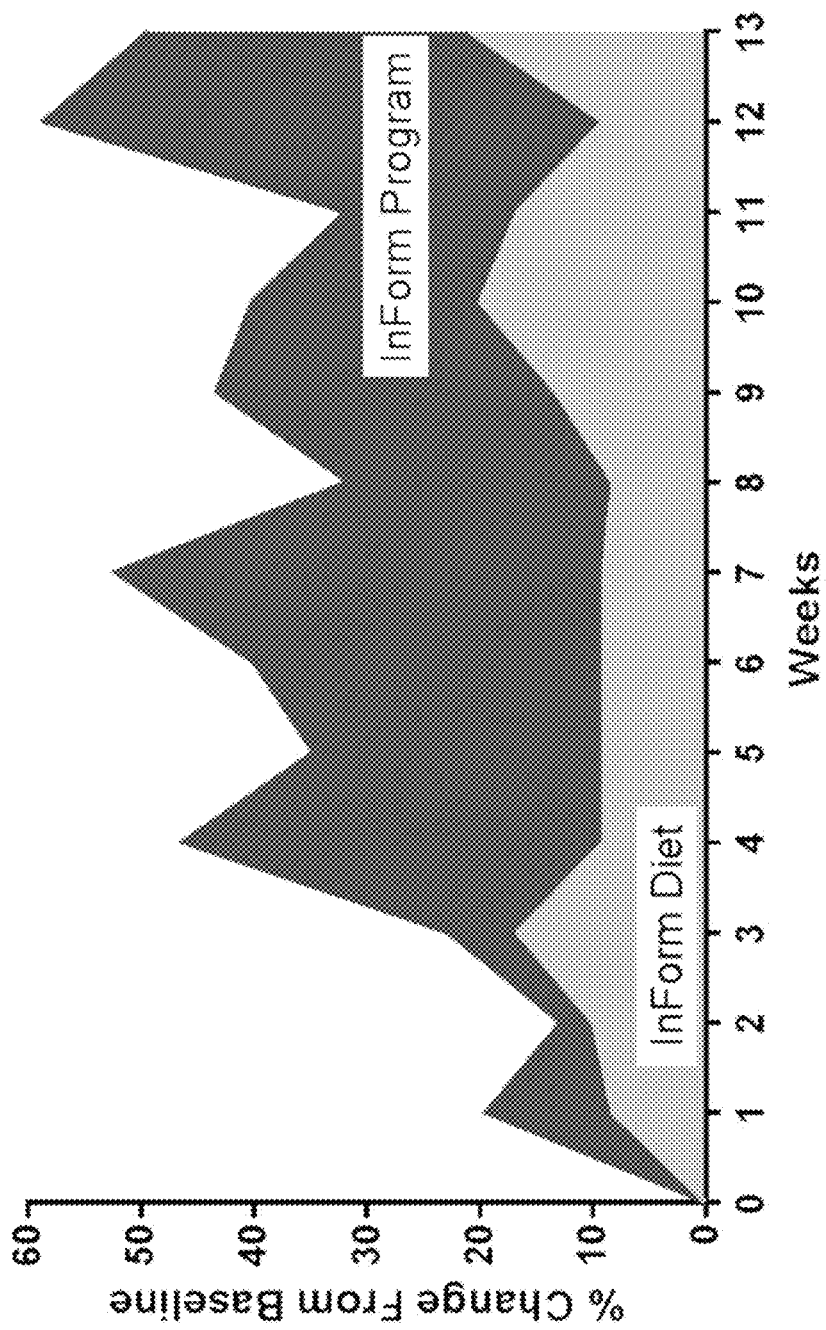
FIG. 6 graphically depicts the median percent change from baseline of salivary nitrite of Arm A and Arm B subjects over the 13 weeks of the InForm 1.1 clinical trial.
Figure 7:
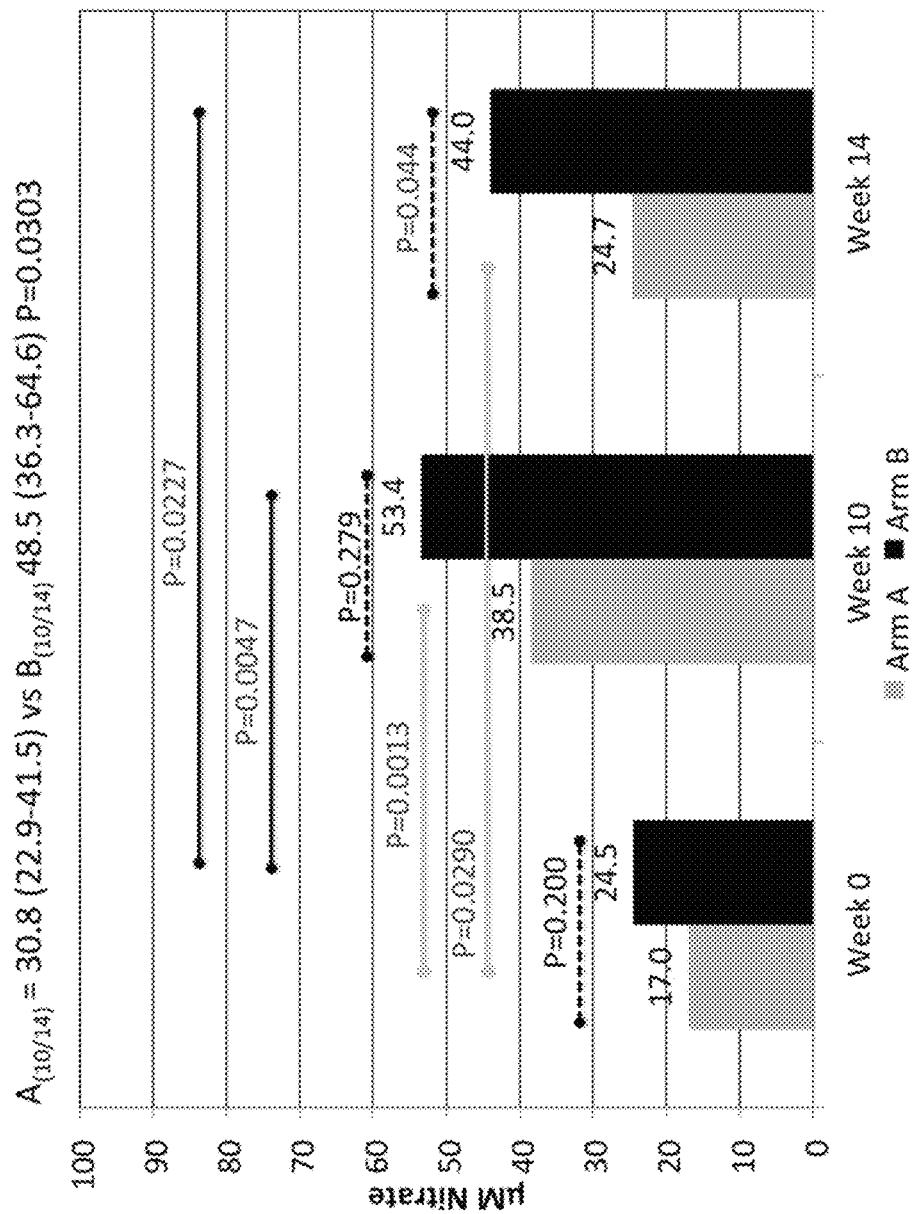
FIG. 7 graphically depicts the mean morning plasma nitrate concentrations at week 0, week 10 and week 14 clinic visits for Arm A and Arm B subjects in the clinical trial.

While both arms of the study exhibited an increase in the salivary NO biomarker nitrite, supplementation with the weight loss stimulating dietary supplements resulted in a median percent increase of 110 percent in salivary NO biomarker production in Arm B over Arm A. See Table 10; FIG. 6. Similarly, plasma nitrate was increased by dietary modification in both arms at 10 and 14 weeks, but supplementation with the weight loss stimulating dietary supplements produced a 1.6-fold increase in overall mean plasma nitrate concentration over the study –30.8 μM (95% confidence interval: 22.9-41.5) vs 48.5 μM (36.3-64.6) with p=0.030. See FIG. 7.

TABLE 10

Median Salivary NO Biomarker Increase

| Treatment Arm | Median % Increase | P-Value |
|---|---|---|
| Arm A (Diet Only) | 21 | 0.0471 |
| Arm B (Diet and Program) | 49 | 0.0004 |
| Arm A vs B | 110 | 0.0003 |

Thus, it has been demonstrated that healthy gut modification through supplementation with the group of weight loss stimulating dietary supplements has led to increased plasma $NO_3$ and salivary $NO_2$, precursors of NO.

FIG. 6 schematically represents week 13 to baseline comparison of subjects scored NO biomarker strips one hour after dinner weekly.

Results Blood Pressure Changes—

Coincident with increases in plasma $NO_3$ and the salivary NO biomarker $NO_2$, both diets decreased blood pressure values from week 1 initial clinic visits. See Table 11. There was a trend for a greater decrease in Arm B over Arm A, but the differences did not reach statistical significance.

TABLE 11

Median Percent Changes in Blood Pressure from Baseline

| | Median % Change† | | Median % Change | |
|---|---|---|---|---|
| | Systolic | Diastolic | Systolic | Diastolic |
| Arm A | −5* | −7* | — | |
| Arm B | −11† | −12† | −125 | −62§ |

From Baseline to Week 13;
*p < 0.05;
†p < 0.01;
§p = 0.06

Results Lipid Biomarker Changes—

Overall, lipid biomarkers were more favorably improved in the Arm B than Arm A. See Table 12. Thus, in addition to increased weight loss, Arm B was more effective in the reduction of cardiovascular risk factors associated with lipid biomarkers. The improvement in TG/HDL ratio also indicates the potential of the diet program to modify risk of developing metabolic syndrome and type 2 diabetes.

TABLE 12

Median Percent Changes of Lipid Biomarkers (Arm A) versus (Arm B)

| Lipid Biomarker | Arm A | Arm B | Improvement |
|---|---|---|---|
| Total Cholesterol (TC) | −8.0** | −18** | −129** |
| LDL Cholesterol (LDL) | −10* | −19** | −80** |
| Triglycerides (TG) | −31** | −51** | −66* |
| High Density Lipoprotein (HDL) | −6 | −3 | −54 |
| TC/HDL | −4.0 | −16** | −268** |
| LDL/HDL | −0.9 | −16 | −1751** |
| TG/HDL | −26* | −47** | −80* |

*$p < 0.05$;
**$p < 0.01$ vs baseline within Arms and Program v Diet alone

Example 2

Individual Case Management of Subject J in InForm1.1

Subject J in InForm1.1 followed the Program for Healthy Weight and Cardiometabolic Function (Arm B) as described in Example 1 with the changes in diagnostic criteria for metabolic syndrome listed in Table 13.

TABLE 13

Changes in Diagnostic Criteria for Metabolic Syndrome during InForm1.1

| Risk Factor† | Start | 9 Weeks | 13 Weeks |
|---|---|---|---|
| Metabolic Syndrome Criteria | 4 | 2 | 2 |
| Metabolic Syndrome (≥3 of 5 criteria) | Yes | No | No |
| Triglycerides ≥150 mg/dL | 171† | 84 | 80 |
| HDL Cholesterol <40 mg/dL men or <50 mg/dL women | 46† | 47† | 48† |
| Fasting glucose ≥100 mg/dL | 99 | 89 | 83 |
| Abdominal obesity as waist circumference in inches >40 inches (men) or >35 inches (women) | 37.5† | 34.4 | 32.5 |
| Blood pressure: Systolic ≥130 mm Hg/ Dystolic ≥85 mm Hg | 159/98† | 148/87† | 136/78† |

†Positive diagnostic criteria

After only 9 weeks on the InForm1.1 Program for healthy weight and cardiometabolic function, Subject J was no longer diagnostic of metabolic syndrome.

Example 3

Individual Case Management of Subject SAF in InForm1.1

Subject SAF followed the Inform1.1 program for healthy weight and cardiometabolic function (Arm B) as described in Example 1 with the changes in diagnostic criteria for metabolic syndrome listed in Table 14.

TABLE 14

Subject SAF Changes in Diagnostic Criteria for Metabolic Syndrome

| Risk Factor† | Start | 9 Weeks | 13 Weeks |
|---|---|---|---|
| Metabolic Syndrome Criteria | 3 | 1 | 2 |
| Metabolic Syndrome (≥3 of 5 criteria) | Yes | No | No |
| Triglycerides ≥150 mg/dL | 163† | 75 | 67 |
| HDL Cholesterol <40 mg/dL men or <50 mg/dL women | 47† | 50 | 48† |
| Fasting glucose ≥100 mg/dL | 86 | 80 | 80 |
| Abdominal obesity as waist circumference in inches >40 inches (men) or >35 inches (women) | 44.5† | 40.0† | 38.5 |
| Blood pressure: Systolic ≥130 mm Hg/ Dystolic ≥85 mm Hg | 118/80 | 117/76 | 107/73 |

†Positive diagnostic criteria

After only 9 weeks on the InForm1.1 Program for Healthy Weight and Cardiometabolic Function, Subject SAF was no longer diagnostic of metabolic syndrome.

Example 4

Evaluation of a Secondary Program for Healthy Weight and Cardiometabolic Function The Program as described in Example 1 is replicated with the substitution of three capsules of CurcuminBP per day for a total dose of about 1,568 mg total curcumiinoids for the BerberineIR used in Example 1. This substitution produces similar positive effects on health, cardiometabolic and body weight variables as described in Example 1.

Example 5

InForm1.2 an Additional Program for Healthy Weight and Cardiometabolic Function

The Program as described in Example 1 was replicated with the following modifications: (1) the trail was a single-arm, observational study, (2) 1,000 mg of cinnamon divided over two doses was substituted for the 999 mg of berberine, and (3) one to three capsules of *Bacillus coagulans* per day for a total dose of about 3 to 9 billion cfu per day was substituted for the Probiotic 11 used in Examples 1 and 4. A complete outline of the clinical protocol is presented in Table 15. The food plan was that as described previously in Table 5.

TABLE 15

InForm1.2 Observational Study Design

| Activity | Details |
|---|---|
| Recruiting and Screening | Recruit generally healthy overweight and obese adults. Physical Measurements (height, weight and waist circumference). Clinical assessment (completion of medical history questionnaire, and visit with study clinician including limited physical examination) Phlebotomy for complete metabolic profile (CMP), HbA1c, insulin and serum pregnancy test for women of child bearing potential. |
| Week 0/ Visit 1 | Confirm cardiometabolic syndrome with repeat physical and clinical variables. Measurements included: Physical measurements (Height, Weight and Waist Circumference), Vital signs (including blood Pressure and heart Rate), Body Impedance Analysis, Peripheral Artery Tonometry, Metabolic age, Clinical assessment (completion of |

TABLE 15-continued

InForm1.2 Observational Study Design

| Activity | Details |
|---|---|
| | medical history questionnaire, and visit with study clinician), Urine pregnancy test for women of child bearing potential, Fasting phlebotomy for CBC, CMP, insulin, HbA1c, oxidized LDLc (oxLDL), myeloperoxidase (MPO), high sensitivity C-reactive protein (hs-CRP), advanced lipid panel including standard lipid panel, particle sizes and particle numbers (NMR) for all subjects. |
| Weeks 1-13 | Low-glycemic food plan<br>Physical activity<br>Cognitive Behavioral Program<br>Protein Shakes (bid)<br>20 g protein<br>2 g Phytosterols<br>Supplements<br>Antioxidant formulation<br>Probiotic<br>Fish oil capsules<br>Cinnamon<br>Fiber drinks |
| Weeks 1-8 and 10-13 | All subjects met collectively with the study clinician for a cognitive behavioral program at 11 didactic/experiential group visits, the body weight, body composition and blood pressures were measured weekly. |
| Weeks 9 and 13 | Review questionnaires, assess for signs and symptoms of adverse events, review compliance to the study products and answer any participant questions. Measurements of baseline variables repeated. |

TABLE 16

Meal Replacement and Weight Loss Stimulating Supplements for InForm1.2

| | Daily Servings | Function |
|---|---|---|
| Meal Supplement | | |
| Meal Replacement | 2 scoops 2x | Amino acids/antioxidants |
| Weight Loss Stimulating Supplements | | |
| Phytosterols | 1 scoop 2x | Biomatrix enrichment |
| Cinnamon | 500 mg bid with shake | Antimicrobial |
| CardioxLDL ® | 2 capsules/dinner | Antioxidant |
| Bacillus coagulans | 1 capsule 3 billion CFU/meal | Repairing dysbiosis |
| Super Omega-3 EPA | 1 capsule 2x | Anti-inflammatory |
| Super Supplemental Vitamins & Minerals and Minerals | 2 tablets 2x | Biomatrix enrichment |

Figure 8:
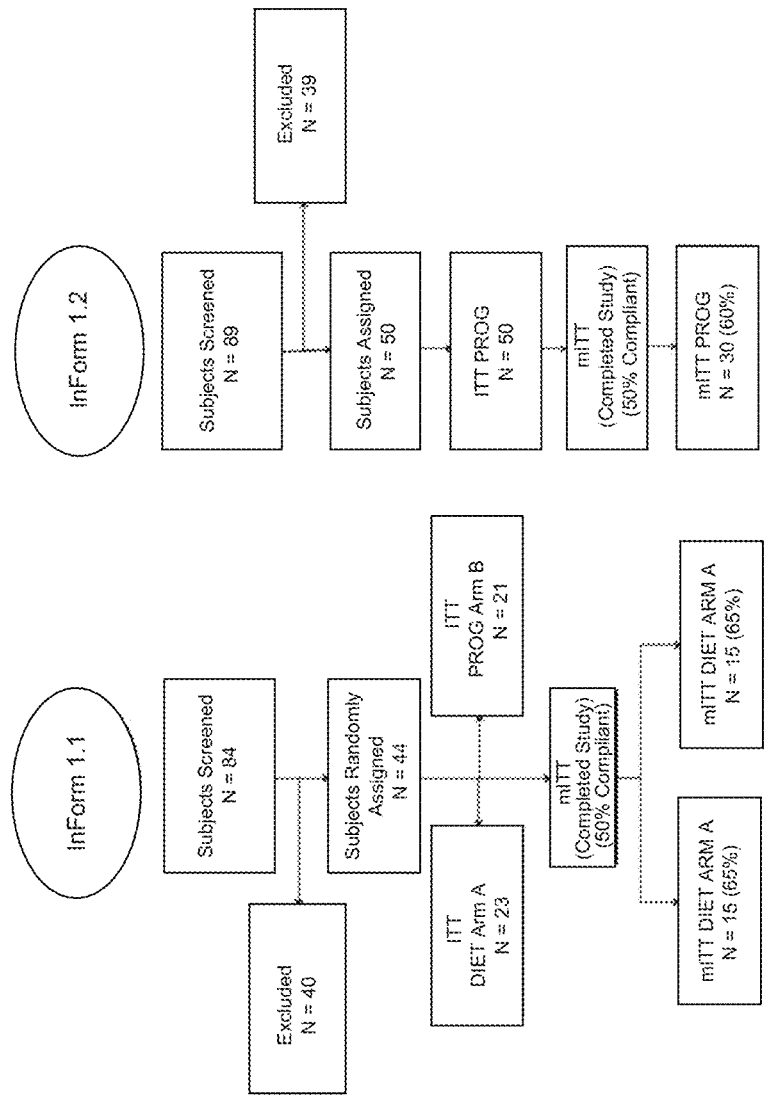
FIG. 8 is a schematic illustration of the disposition of subjects in both the InForm1.1 and InFrom1.2 clinical trials on the intent-to-treat and modified intent-to-treat basis.

The clinical data from both studies were analyzed on both an intent-to-treat (ITT) and modified intent-to treat (mITT) basis (cf FIG. 8 for disposition of subjects by study and method of analysis).

Intent-To-Treat (ITT) Data Analysis—

This analysis considers all subjects randomized into their respective treatments and estimates responses from dropouts through the last-observation-carry forward method. The ITT analysis is considered the most conservative estimate of effectiveness as it reflects conditions likely to be encountered in the market.

TABLE 17

Baseline Median Cardiometabolic Profiles of DIET, PROG1.1 and PROG1.2 Subjects for Intent-To-Treat Analysis

| Variable | DIET ONLY† (n = 23) | PROG1.1† (n = 21) | PROG1.2† (n = 50) |
|---|---|---|---|
| Gender, % Female | 60.9 | 66.7 | 60.0 |
| Age (yrs) | 47 (64-33)$^a$ | 46 (64-27)$^a$ | 45 (63-25)$^a$ |
| Weight (lb) | 229 (383-165)$^a$ | 229 (296-170) $^a$ | 231 (343-164) $^a$ |
| BMI (kg/m$^2$) | 34.6 (53.0-26.9)$^a$ | 35.4 (43.0-31.3) $^a$ | 35.9 (50.8-28.6) $^a$ |
| Body Fat Mass (lbs) | 92.8 (149-45.5)$^a$ | 96.7 (131-68.3)$^a$ | 93.9 (168-53.7)$^a$ |
| Waist circumference (in) | 44.0 (61.0-35.5)$^a$ | 44.5 (52.0-35.0) $^a$ | 44.3 (59.5-38.0)$^a$ |
| Systolic BP (mm Hg) | 136 (172-102)$^a$ | 133 (164-115)$^a$ | 130 (167-101)$^a$ |
| Diastolic BP (mm Hg) | 83 (99-71)$^a$ | 83 (99-73)$^a$ | 84 (108-66)$^a$ |
| Salivary Nitrite (Morning units) | 3.0 (7.0-0.10)$^a$ | 3.0 (7.5-1.0)$^a$ | 3.0 (5.0-0.10)$^a$ |
| Salivary Nitrite (Noon units) | 4.5 (6.8-0.10)$^a$ | 3.5 (6.5-0.10)$^a$ | 4.0 (7.0-1.0)$^a$ |
| Salivary Nitrite (Evening units) | 5.3 (7.4-2.0)$^a$ | 4.0 (7.0-0.10$^a$ | 4.4 (7.0-1.5)$^a$ |
| Total Cholesterol (mg/dL) | 199 (256-149)$^a$ | 224 (320-137)$^a$ | 201 (423-139)$^a$ |
| LDL Cholesterol (mg/dL) | 128 (177-76)$^a$ | 138 (217-60)$^a$ | 121 (201-44)$^a$ |
| TG (mg/dL) | 173 (571-77)$^a$ | 184 (332-96)$^a$ | 171 (527-81)$^a$ |
| HDL Cholesterol (mg/dL) | 43 (67-25)$^a$ | 42 (81-26)$^a$ | 40 (64-24)$^a$ |
| oxLDL (U/L) | 47 (77-32)$^a$ | 50 (79-23)$^a$ | 52 (116-6.1)$^a$ |
| Cholesterol/HDL | 4.7 (7.5-2.7)$^a$ | 5.1 (7.9-3)$^a$ | 5.0 (12.4-2.8)$^a$ |
| LDL/HDL | 2.8 (5.2-1.2) | 2.8 (5.2-1.2) | 3.0 (4.8-1.3) |
| TG/HDL | 4.0 (23-1.5)$^a$ | 4.3 (11.4-1.2)$^a$ | 4.3 (22-1.5)$^a$ |
| oxLDL/HDL | 1.1 (1.9-0.61)$^a$ | 1.2 (1.8-0.36)$^a$ | 1.4 (3.4-0.16)$^a$ |
| Glucose (mg/dL) | 92 (121-71)$^a$ | 90 (103-79)$^a$ | 93 (121-64)$^a$ |
| Insulin (μIU/mL) | 7.5 (18-2.5)$^a$ | 7.5 (27-2.7)$^a$ | 9.4 (31-1.0)$^b$ |
| HbA1C (%) | 5.8 (7.0-5.7)$^a$ | 5.7 (6.2-4.8)$^a$ | 5.8 (6.8-5.2)$^a$ |
| HOMA-IR | 1.78 (4.25-0.50)$^a$ | 1.72 (5.80-0.54)$^a$ | 2.24 (8.21-0.21)$^b$ |
| HOMA-β | 90 (369-50)$^a$ | 104 (427-40.5)$^a$ | 116 (1656-17.1)$^a$ |
| hs-CRP (mg/L) | 2.6 (42-0.60)$^a$ | 2.9 (9.8-0.40)$^a$ | 3.3 (27-0.50)$^a$ |
| 10-Year Cardiac Risk/BMI (%) | 6.9 (23-2.3)$^a$ | 7.1 (23-2.0)$^a$ | 6.9 (19-0.89)$^a$ |
| 10-Year Cardiac Risk/Lipids (%) | 6.1 (15-2.6)$^a$ | 6.5 (18-1.4)$^a$ | 5.7 (20-0.80)$^a$ |

BMI: Body Mass Index; BP = Blood Pressure; LDL: Low Density Lipoprotein; HDL: High Density Lipoprotein; OxLDL: Oxidized Low Density Lipoprotein; Apo A: Apolipoprotein Al; Apo B: Apolipoprotein B; HbA1c: Glycated Hemoglobin; HOMA-IR: Homeostatic Model Assessment Insulin Resistance computed using the formula HOMA-IR = [(Glucose$_{mg/dL}$) × (Insulin$_{μU/mL}$)]/405; hs-CRP: high sensitivity C-reactive protein.
†Tabulated values are medians with parenthetic minimum and maximum values, respectively; common superscript letters indicate P > 0.05 computed from Mann-Whitney U-Test.

Intent-to-Treat Analysis Results—

Groups representing the DIET only and PROG treatments from InForm1.1 and InForm1.2 were similar at baseline (Table 17). Insulin and HOMA-IR scores were statistically elevated compared to DIET and InForm1.1 arms but in the normal range.

Table 18 summarizes the effects of DIET, PROG1.1 and PROG1.2 on the clinical variables as median percent changes from baseline for the ITT analysis.

Overall Results—

In general, the DIET performed well and provided significant improvements from baseline for critical variables such as weight loss, fat mass, select lipid and glucose biomarkers and 10-year cardiovascular risk. Overall, however, PROG1.1 and PROG1.2 dramatically outperformed the DIET ONLY group in all of these variables. Several statistically significant differences between the two programs existed and are detailed in the following sections.

Results Weight and Fat Loss—

Supplementation with the meal replacement formulation and weight loss stimulating dietary supplements, (PROG1.1 and PROG1.2 Systems) produced losses of 7.5% (17 pounds) and 8.4% (20 pounds), respectively versus a 4.4% (9 pounds) weight in the non-supplemented CTRL arm. (cf FIG. 9A). As expected, similar results were seen for BMI.

Figure 9B:
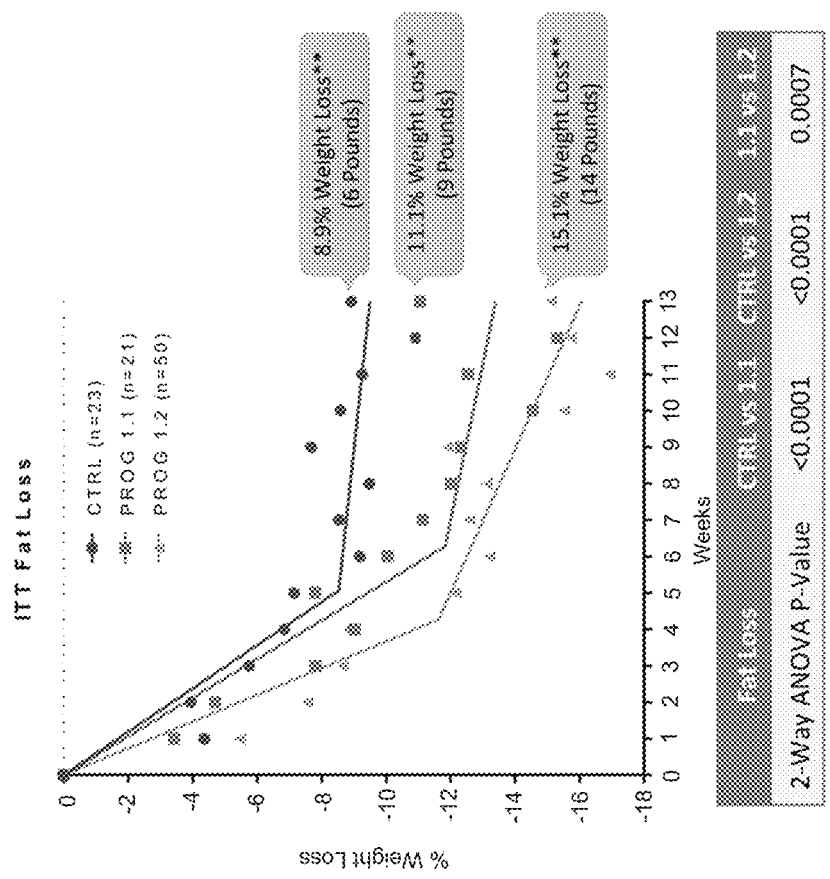
FIG. 9B graphically depicts the median percent change from baseline of fat loss of subjects over 13 weeks of the InForm 1.1 clinical trial, In Form 1.2 clinical trial, and the control as based upon an intent-to-treat analysis.
Figure 9A:
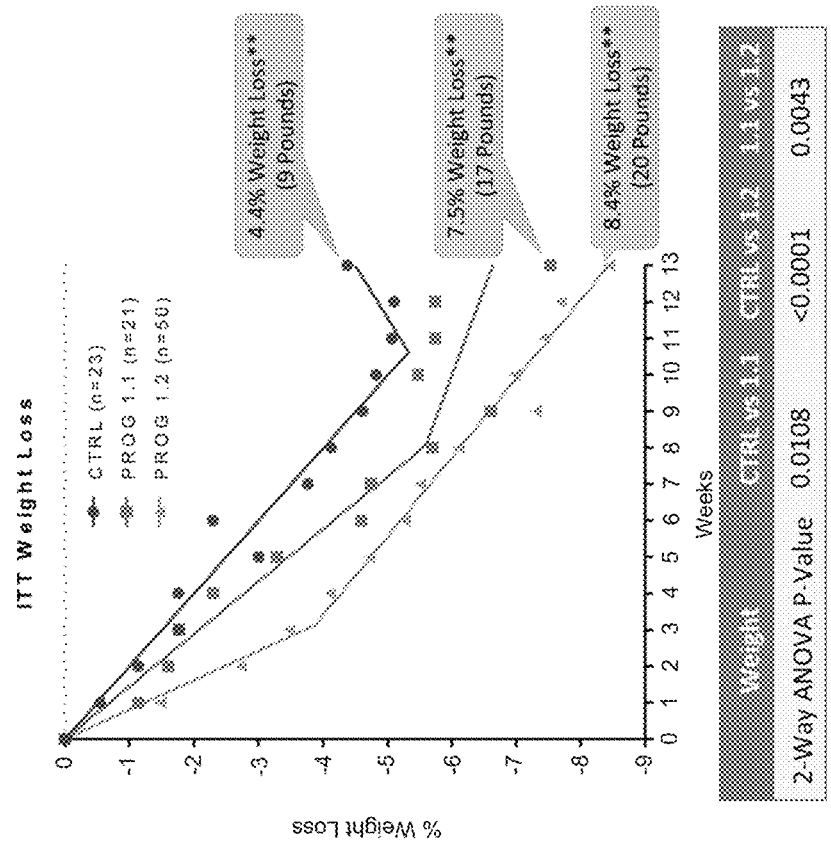
FIG. 9A graphically depicts the median percent change from baseline of weight loss of subjects over the 13 weeks of the InForm 1.1 clinical trial, InForm1.2 clinical trials and the control as based upon an intent-to-treat analysis.

Loss of fat mass (lbs) was also significantly better in the PROG1.1 and PROG1.2 arms compared to the DIET ONLY with median percent decreases from baseline of 11.1% and 15.1%, respectively, compared to 8.9% in the CTRL arm. PROG1.2 was also significantly different from PROG1.1 (P<0.0007; FIG. 9B).

Figure 10B:
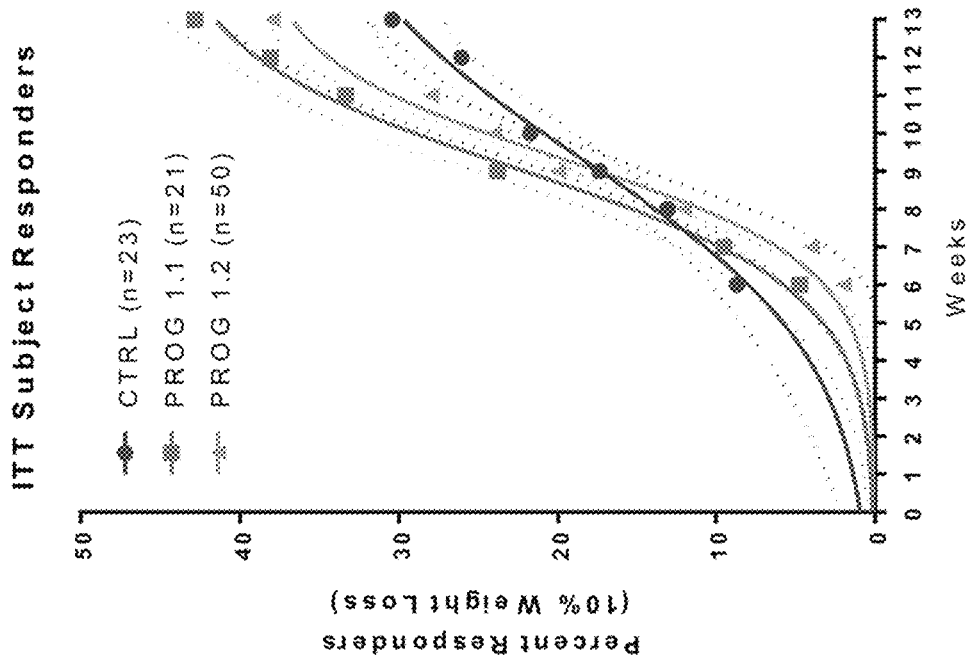
FIG. 10B graphically depicts the number of subjects overall achieving a 10% weight loss as determined from an intent-to-treat analysis.
Figure 10A:
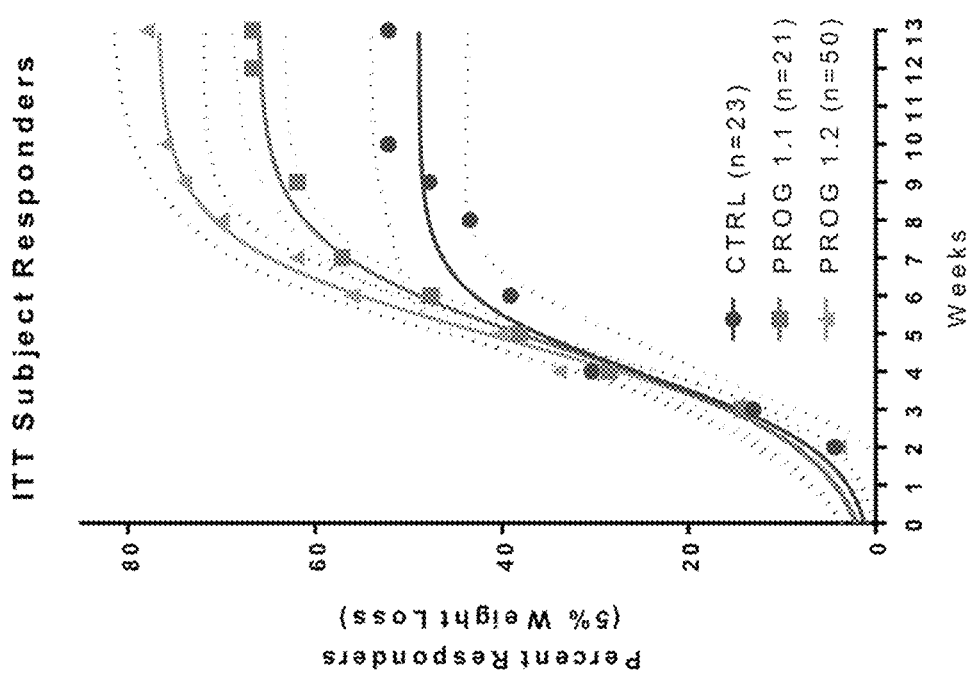
FIG. 10A graphically depicts the number of subjects overall achieving a 5% weight loss as determined from an intent-to-treat analysis.
Figures 11A, 11B:
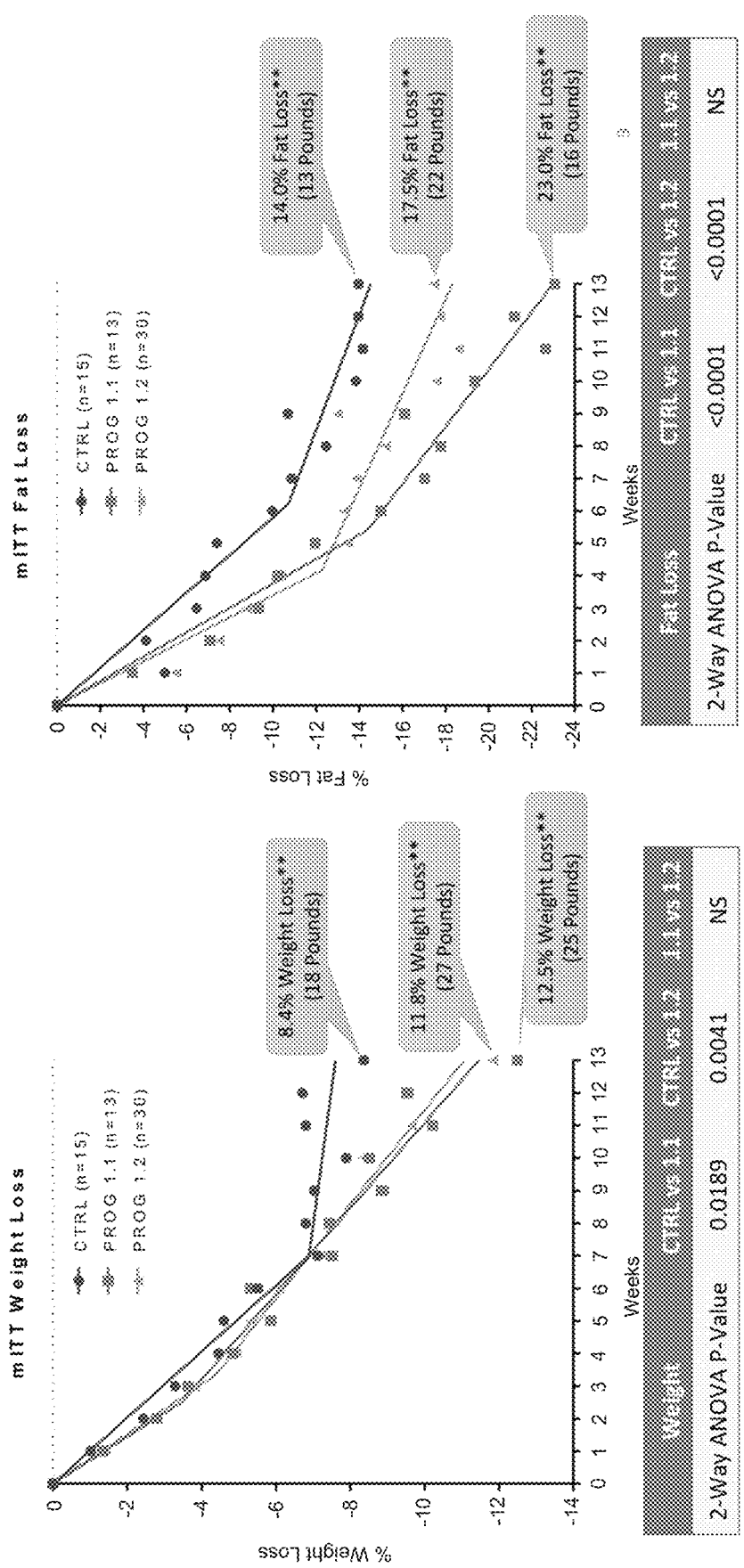
FIG. 11A graphically depicts the median percent change from baseline of weight loss of subjects over the 13 weeks of the InForm 1.1 clinical trial, the Inform 1.2 clinical trials and the control as based upon a modified intent-to-treat analysis.
FIG. 11B graphically depicts the median percent change from baseline of fat loss of subjects over the 13 weeks of the InForm 1.1 clinical trial, the Inform 1.2 clinical trials and the control as based upon a modified intent-to-treat analysis.
Figures 12A, 12B:
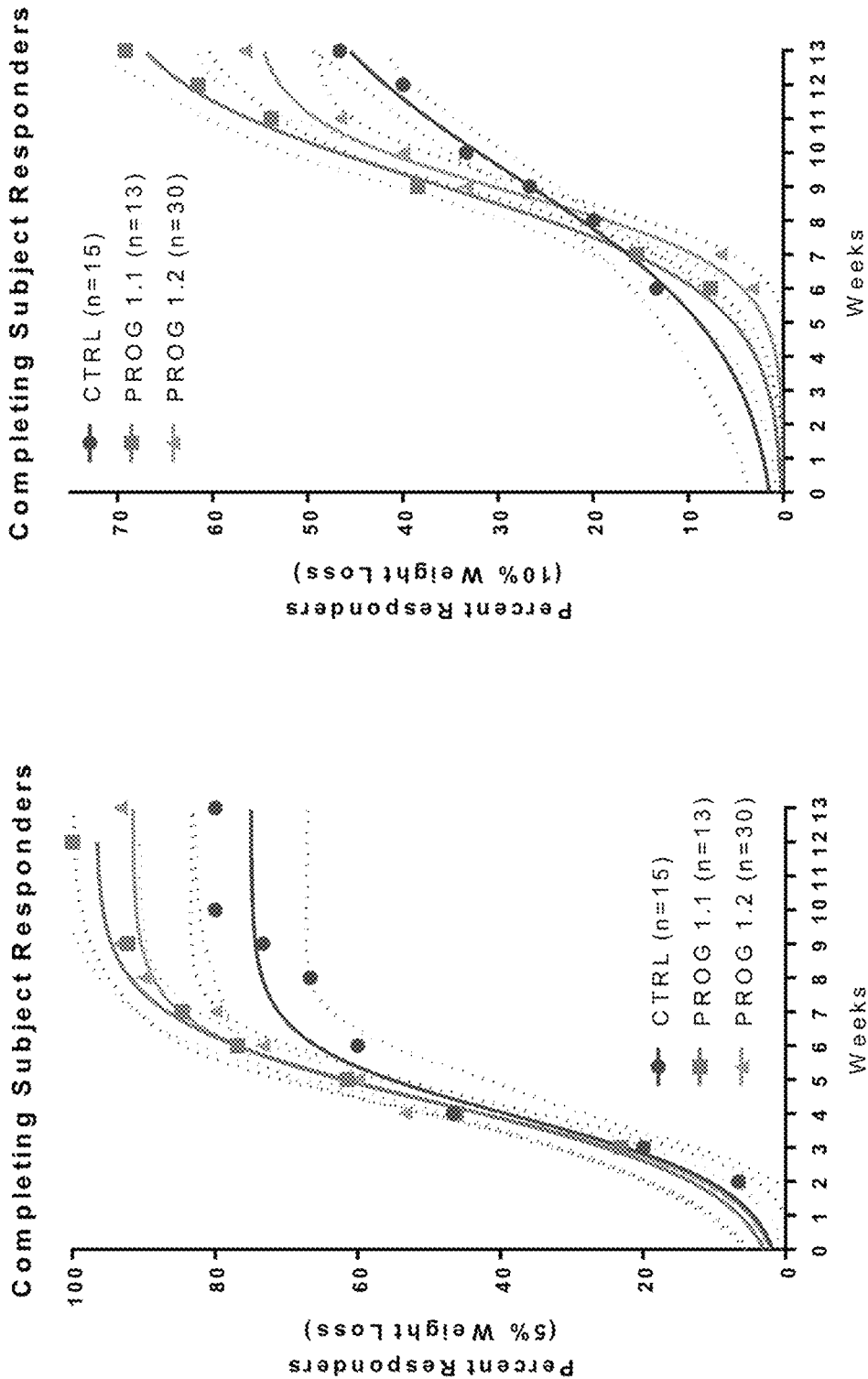
FIG. 12A graphically depicts the number of subjects overall achieving a 5% weight loss as determined from a modified intent-to-treat analysis.
FIG. 12B graphically depicts the number of subjects overall achieving a 10% weight loss as determined from a modified intent-to-treat analysis.

Further, the number of subjects achieving either a 5% or 10% weight loss was substantially better for both PROG arms relative to DIET ONLY, FIG. 10A and FIG. 10B, respectively. A greater number of subjects achieved a 5% weight loss in PROG1.2 than PROG1.1, but these results reversed for the percent of subjects achieving a 10% weight loss.

Results Blood Pressure—

No change from baseline was observed for either systolic or diastolic blood pressure for the DIET ONLY arms, while both PROG1.1 and PROG1.2 produced similar decreases in blood pressure of 7.8% and 6.6% for systolic and 6.7% and 92% for diastolic, respectively. These changes in blood pressure were mirrored by increases in salivary nitrite observed in both PROG arms.

Lipid Biomarkers—

Total and LDL cholesterol were reduced from baseline to a greater extent in the supplement arms than in the DIET ONLY group. Triglycerides were decreases to a similar extent in all three arms, respectively, 27, 31 and 33% for DIET, PROG1.1 and PROG1.2.

Glucose Biomarkers—

Glucose, insulin, HbA1c and HOMA-IR were more dramatically reduced in the PROG1.2 arm than in the PROG1.1 or DIET ONLY arm.

Inflammation Biomarkers— hs-CRP was reduced to a similar extent in the PROG1.1 and PROG1.2 arms, 18 and 19% from baseline respectively, while no change from baseline was noted for the DIET ONLY arm.

10-year Cardiovascular Risk—

The decreases in 10-year cardiovascular risk based on BMI in the PROG1.1 and PROG1.2 arms were 2.9- and 3-fold times the 6.2% decrease in the DIET ONLY arm. Even more dramatic was the decrease seen in 10-year cardiovascular risk seen when estimated from serum lipid changes. PROG1.1 and PROG1.2 were 13- and 14-fold better than diet alone.

TABLE 18

DIET and PROG Cardio-Metabolic Risk Variables for ITT Analysis

| Variable | DIET ONLY (n = 23)† Median % Change† | PROG1.1 (n = 21)† Median % Change† | PROG1.2 (n = 50)† Median % Change† |
|---|---|---|---|
| Weight (lbs) | −4.4**[a] (6 to −19.6) | −7.5**[b] (0.0 to −16) | −8.4**[c] (0.0 to −21) |
| BMI (kg/m$^2$) | −4.4**[a] (6 to −20) | −7.5**[b] (0.0 to −16) | −8.4**[c] (0.0 to −21) |
| Fat Mass (lbs) | −8.9**[a] (3.8 to −27) | −11**[b] (2.7 to −35) | −15**[c] (0.0 to −38) |
| Waist circumference (in) | 6.7**[a] (0.0 to −17) | −9.5**[b] (0.0 to −17) | −7.5**[b] (0 to −20) |
| Systolic BP (mm Hg) | 0.0[a] (13 to −24) | −7.8**[b] (7.1 to −24) | −6.6**[b] (11 to −32) |
| Diastolic BP (mm Hg) | 0.0[a] (8.2 to −19) | −6.7**[b] (2.6 to −21) | −9.2**[b] (7.7 to −27) |
| Nitrate Strip - Morning | 26[a] (1900 to −97) | 33**[b] (140 to −13) | 33**[b] (3900 to −67) |
| Nitrate Strip - Afternoon | 18[a] (5600 to −73) | 25**[b] (7400 to −11) | 25** b (300 to −68) |
| Nitrate Strip - Evening | 9.1[a] (150 to −95) | 27**[b] (7900 to −29) | 29**[b] (233 to −43) |
| Total Cholesterol (mg/dL) | −3.6** (21 to −34) | −9.3** (0.0 to −31) | −12** (54 to −38) |
| LDL Cholesterol (mg/dL) | 0.0 (65 to −37) | −6.8* (33 to −35) | −11** (128 to −37) |
| TG (mg/dL) | −27** (7.7 to −55) | −31** (30 to −68) | −33** (27 to −80) |
| HDL Cholesterol (mg/dL) | 0.0 (18 to −19) | 0.0 (17 to −12) | 0.0 (57 to −34) |
| oxLDL (U/L) | −3.1* (37 to −41) | 0.0 (6.7 to −37) | −12** (507 to −56) |
| Cholesterol/HDL | −2.5 (30 to −41) | −13** (1.3 to −35) | −12** (21 to −55) |
| LDL/HDL | 0.0 (69 to −44) | −9.3** (15 to −42) | −11* (47 to −53) |
| TG/HDL | −25** (15 to −60) | −26** (34 to −73) | −32** (41 to −87) |
| oxLDL/HDL | 0.0 (27 to −45) | −7.8** (19 to −44) | −8.5** (450 to −69) |
| Glucose (mg/dL) | 0.0 (16 to −37) | 0.0 (12 to −16) | −1.6** (28 to −20) |
| Insulin (μIU) | −14* (31 to −72) | −6.7* (57 to −76) | −29** (305 to −82) |
| HbA1c (%) | 0.0 (8.6 to −14) | 0.0 (4.2 to −11) | −3.4** (1.7 to −9.2) |
| HOMA-IR | −8.2* (30 to −82) | −8.9** (69 to −79) | −30** (333 to −84) |
| HOMA-β | −9.2* (60 to −74) | −11** (23 to −69) | −21** (249 to −97) |
| hs-CRP (mg/L) | 0.0 (439 to −63) | −18** (67 to −55) | −19** (471 to −75) |

TABLE 18-continued

DIET and PROG Cardio-Metabolic Risk Variables for ITT Analysis

| Variable | DIET ONLY (n = 23)† Median % Change† | PROG1.1 (n = 21)† Median % Change† | PROG1.2 (n = 50)† Median % Change† |
|---|---|---|---|
| 10-Year Cardiac Risk/BMI (%) | −6.2* (35 to −54) | −18** (3.5 to −56) | −19** (17 to −67) |
| 10-Year Cardiac Risk/Lipids (%) | −1.8* (29 to −57) | −26** (3.6 to −69) | −28** (22 to −62) |

Note:
BMI: Body Mass Index; BP: blood pressure; LDL: Low Density Lipoprotein; HDL: High density lipoprotein; TG: triglycerides; High Density Lipoprotein; OxLDL: Oxidized Low Density Lipoprotein; Apo A: Apolipoprotein A1; Apo B: Apolipoprotein B HbA1c: Glycated Hemoglobin; HOMA-IR: Homeostatic Model Assessment Insulin Resistance computed using the formula HOMA-IR = [(Glucose$_{mg/dL}$) × (Insulin$_{\mu U/mL}$)]/405; HOMA-β = [(360x Insulin$_{\mu u/mL}$)/(Glucose$_{mg/dL}$)]%; hs-CRP: high sensitivity C-reactive protein.
†Tabulated values are medians with parenthetic maximum and minimum values, respectively
*P < 0.05 and **P < 0.01 for % change between baseline and week 13 within arms computed using the Wilcoxon Rank Sign Test as described in Methods with (a) uncommon superscript letters indicate significant differences among arms with P-values between arms were computed using a 2-way ANOVA of the log (week/baseline) as described in Methods.

Modified Intent-To-Treat (mITT) Data Analysis—

This analysis considers only subjects who completed the study and were judged more than 50% compliant based upon weekly assessment sheets. This resulted in a 35% loss of subjects (n=15 reduced from 23) in the DIET ONLY arm, a 38% loss in the PROG1.1 arm and a 40% loss in the PROG1.2 arm. The mITT analysis is considered the better estimate of efficacy over effectiveness as it assures the subjects adherence to the regimen.

Modified Intent-to-Treat Analysis Results—

Groups representing the DIET and PROG treatments from InForm1.1 and InForm1.2 were similar at baseline (Table 19).

TABLE 19

Baseline median cardiometabolic profiles of DIET and PROG subjects for mITT

| Variable | DIET ONLY† (n = 15) | PROG1.1† (n = 13) | PROG1.2† (n = 30) |
|---|---|---|---|
| Gender, % Female | — | — | — |
| Age (yrs) | — | — | — |
| Weight (lb) | 226 (383-165) | 229 (296-170) | 223 (315-173) |
| BMI (kg/m$^2$) | 37.0 (53.0-26.9) | 34.7 (42.7-31.3) | 36.0 (47.7-28.6) |
| Body Fat (lbs) | 108 (149-45.5) | 91.7 (129-68.3) | 96.7 (145-60.3) |
| Waist circumference (in) | 45.0 (61.0-35.5) | 45.8 (52.0-35.0) | 44.0 (53.0-38.0) |
| Systolic BP (mm Hg) | 129 (172-102) | 133 (160-115) | 131 (167-101) |
| Diastolic BP (mm Hg) | 85 (99-73) | 83 (99-78) | 85.8 (108-66) |
| Salivary Nitrite (Morning units) | 3.0 (5-1) | 3.5 (7.5-10) | 3.0 (5.0-0.10) |
| Salivary Nitrite (Noon units) | 5.0 (6.8-2.3) | 3.5 (6.0-0.10) | 4.0 (7.0-1.0) |
| Salivary Nitrite (Evening unit | 5.5 (7.4-2) | 4.0 (7.0-0.10) | 5.0 (7.0-1.5) |
| Total Cholesterol (mg/dL) | 198 (256-173) | 192 (242-137) | 200 (423-153) |
| LDL Cholesterol (mg/dL) | 122 (169-83) | 119 (152-60) | 117 (201-69) |
| TG (mg/dL) | 162 (284-95) | 184 (332-96) | 171 (491-81) |
| HDL Cholesterol (mg/dL) | 46 (67-32) | 38 (80-26) | 42 (64-28) |
| oxLDL (U/L) | 47 (63-35) | 42 (55-23) | 50 (116-6.1) |
| Cholesterol/HDL | 4.7 (7.5-2.7) | 5.1 (7.9-3) | 5.1 (12.4-2.8) |
| LDL/HDL | 2.7 (5.2-1.2) | 3 (4.6-1.4) | 3 (4.8-1.3) |
| TG/HDL | 3.3 (8.6-1.5) | 4.3 (11.4-1.2) | 4.3 (14.4-1.5) |
| oxLDL/HDL | 1.1 (1.8-0.6) | 1.1 (1.8-0.4) | 1.4 (3.4-0.2) |
| Glucose (mg/dL) | 92 (121-71) | 92 (99-84) | 92 (109-64) |
| Insulin (μIU/mL) | 8.2 (18-2.5) | 9.3 (27-3.1) | 9.0 (31-4.6) |
| HbA1C (%) | 5.8 (7-5.1) | 5.8 (6.2-4.8) | 5.8 (6.8-5.4) |
| HOMA-IR | 2 (4.2-0.5) | 2 (5.8-0.7) | 2.1 (8.2-0.7) |
| HOMA-β | 90 (369-50) | 120 (427-46.5) | 127 (1656-61.2) |
| hs-CRP (mg/L) | 2.6 (41.7-0.8) | 3.6 (9.8-0.4) | 3.3 (15.4-0.5) |
| 10-Year Cardiac Risk/BMI (%) | 7.0 (23-2.3) | 7.1 (23.4-2) | 6.7 (14.5-0.9) |
| 10-Year Cardiac Risk/Lipids (%) | 6.4 (15.4-2.6) | 6.5 (18.4-1.4) | 5.8 (19.9-0.8) |

BMI: Body Mass Index; BP = Blood Pressure; LDL: Low Density Lipoprotein; HDL: High Density Lipoprotein; OxLDL: Oxidized Low Density Lipoprotein; Apo A: Apolipoprotein A1; Apo B: Apolipoprotein B; HbA1c: Glycated Hemoglobin; HOMA-IR: Homeostatic Model Assessment Insulin Resistance computed using the formula HOMA-IR = [(Glucose$_{mg/dL}$) × (Insulin$_{\mu U/mL}$)]/405; HOMA-β = [(360x Insulinμ UmL)/(Glucosemg/dL)]%; hs-CRP: high sensitivity C-reactive protein. hs-CRP: high sensitivity C-reactive protein.
†Tabulated values are medians with parenthetic maximum and minimum values, respectively; common superscript letters indicate P > 0.05 computed from Mann-Whitney U-Test Overall Results—

Table 20 summarizes the effects of DIET, PROG1.1 and PROG1.2 on the clinical variables as median percent changes from baseline for the modified intent-to-treat analysis. In general, the results of the mITT analysis were similar to those of the ITT analysis for the majority of clinical variables as well as weight loss, fat loss, and 5 or 10% responders (Table 20, FIG. 11A, 11B, FIG. 12A, 12B). Changes from baseline were more often greater for all arms reflecting the efficacy of the DIET ONLY and PROG arms when subject are compliant. For example, weight loss for the DIET, PROG1.1 and PROG1.2 was 8.4, 11.8, and 12.5% from baseline, respectively in the mITT analysis versus the 4.4, 7.5 and 8.4% in the ITT analysis.

TABLE 20

DIET and PROG Effects on Cardio-Metabolic Risk Variables for Modified Intent-To-Treat Analysis

| Variable | DIET (n = 15)† Median % Change† | PROG1.1 (n = 13)† Median % Change† | PROG1.2 (n = 30)† Median % Change† |
|---|---|---|---|
| Weight (lbs) | −8.4** (−0.9 to −20) | −12.5** (−5.8 to −16.3) | −11.8** (−4.3 to −20.5) |
| BMI (kg/m$^2$) | −8.4** (−0.9 to −20) | −12.5** (−5.8 to −16.3) | −11.8** (−4.3 to −20.5) |
| Fat Mass (lbs) | −14** (−2.8 to −27) | −23** (−1.0 to −35) | −18** (−3.7 to −38) |
| Waist circumference (in) | −8.9** (−4.9 to −17) | −11.6** (−4.2 to −16.9) | −8.8** (−2.3 to −20) |
| Systolic BP (mm Hg) | −5.5 (13 to −24) | −12** (7.1 to −24) | −9.0** (7.2 to −32) |
| Diastolic BP (mm Hg) | −7.4* (8.2 to −19) | −12** (2.6 to −21) | −12** (7.7 to −27) |
| Nitrate Strip - Morning | 33** (450 to −33) | 33** (140 to −13) | 33* (3900 to −67) |
| Nitrate Strip - Afternoon | 20 (182.6 to −33) | 67** (7400 to 0.0) | 25** (300 to −17) |
| Nitrate Strip - Evening | 21 (150 to −33) | 63** (7900 to −14) | 20** (133 to −43) |
| Total Cholesterol (mg/dL) | −11* (21 to −34) | −15** (−1.7 to −31) | −19** (54 to −38) |
| LDL Cholesterol (mg/dL) | −11 (65 to −37) | −10 (33 to −31) | −22** (128 to −37) |
| TG (mg/dL) | −32** (7.7 to −55) | −54** (30 to −68) | −40** (8.3 to −80) |
| HDL Cholesterol (mg/dL) | 0.0 (18 to −19) | 0.0 (17 to −12) | −2.9 (56 to −34) |
| oxLDL (U/L) | −20* (37 to −41) | −8.7 (6.7 to −35) | −17** (507 to −56) |
| Cholesterol/HDL | −8.4 (31 to −41) | −19** (1.3 to −27) | −15** (21 to −55.4) |
| LDL/HDL | −6.9 (69 to −44) | −11** (15 to −28) | −14 (47 to −53) |
| TG/HDL | −31** (15 to −60) | −58** (34 −73) | −35** (24 to −87) |
| oxLDL/HDL | −16* (27 to −45) | −14** (19 to −42) | −13* (450 to −69) |
| Glucose (mg/dL) | −2.0 (16 to −37) | −2.3 (12 to −16.2) | −3.2* (28 to −16) |
| Insulin (μIU) | −32* (31 to −71.9) | −30** (42 to −76) | −43** (34 to −82) |
| HbA1c (%) | −1.8 (8.6 to −14) | −1.9 (4.2 to −11) | −4.1** (0.0 to −8.1) |
| HOMA-IR | −29.6* (29.5 to −82.4) | −34.9* (48 to −79.4) | −43.9** (19.8 to −84.1) |
| HOMA-β | −29.6* (59.7 to −74.3) | −26.2** (22.8 to −68.6) | −36.4** (79.7 to −96.5) |
| hs-CRP (mg/L) | −5.2 (439 to −63) | −31** (67 to −55) | −30* (471 to −75) |
| 10-Year Cardiac Risk/BMI (%) | −17* (35 to −54) | −28** (3.5 to −56) | −25** (16 to −67) |
| 10-Year Cardiac Risk/Lipids (%) | −20* (29 to −57) | −36** (3.6 to −69) | −38** (22 to −62) |

Note:

BMI: Body Mass Index; BP: blood pressure; LDL: Low Density Lipoprotein; HDL: High density lipoprotein; TG: triglycerides; High Density Lipoprotein; OxLDL: Oxidized Low Density Lipoprotein; Apo A: Apolipoprotein A1; Apo B: Apolipoprotein B HbA1c: Glycated Hemoglobin; HOMA-IR: Homeostatic Model Assessment Insulin Resistance computed using the formula HOMA-IR = [(Glucose$_{mg/dL}$) × (Insulin$_{\mu U/mL}$)]/405; HOMA-β = [(360× Insulin$_{\mu U/mL}$)/(Glucose$_{mg/dL}$)]%; hs-CRP: high sensitivity C-reactive protein.

†Tabulated values are medians with parenthetic maximum and minimum values, respectively

*P < 0.05 and **P < 0.01 for % change between baseline and week 13 within arms computed using the Wilcoxon Rank Sign Test as described in Methods (a) uncommon superscript letters indicate significant differences among arms with P-values between arms were computed using a 2-way ANOVA of the log (week/baseline) as described in Methods.

This example demonstrates the effectiveness and efficacy of the addition of a group of weight loss supplements to diet and lifestyle modifications for increased weight loss and a decrease in 10-year cardiovascular risk.

Example 6. Contrasting Macronutrient Content of InForm1.1 and 1.2 Versus DIET Tables 21 and 22 describe the macronutrient content of the InForm1.1 and 1.2 PROG as well as the control DIET used in Examples 1 and 5, respectively as percent of daily calories and g macronutrient per day.

TABLE 21

Macronutrient composition of the study diet as percent of daily calories

| Composition | Mean daily % of calories | | |
|---|---|---|---|
| | DIET | InForm1.1 | InForm1.2 |
| Calories (kcal) | 1510 | 1635 | 1715 |
| Protein | 42.1 | 42.1 | 40.3 |
| Available Carbohydrates | 16.2 | 23.8 | 25.5 |
| Sugars | 2.19 | 3.06 | 2.97 |
| Fiber, g/1000 kcal | | | |
| Dietary | 15.2 | 16.5 | 28.0 |
| Viscous | 3.64 | 5.81 | 17.2 |
| Fat | 41.7 | 34.1 | 34.1 |
| Saturated fatty acids | 6.85 | 5.50 | 5.77 |
| Monounsaturated fatty acids | 19.4 | 14.3 | 13.6 |
| Polyunsaturated fatty acids | 7.45 | 6.88 | 6.56 |
| Dietary cholesterol, mg/1000 kcal | 510 | 404 | 385 |
| Alcohol | — | — | |

Macronutrient dietary components generally associated with the favorable metabolic changes seen in the InForm1.1 and InForm1.2 program studies do not exhibit a consistent difference from the control DIET group that could account for the positive changes described herein. For example, while protein is higher in the test diets, so are the available carbohydrates and sugars. Further, saturated, monounsaturated and polyunsaturated fats are similar over the three dietary treatments either as percent of diet or total daily intake.

Dietary and viscous fiber are both elevated in the InForm programs, 1.7- and 5.5-fold respectively, relative to the DIET program. Additionally, cholesterol content of the two test diets is 21 and 24% lower. Together, these changes have been associated with favorable modifications in blood lipid profiles, but not at the extent demonstrated in these examples.

Therefore, it can be concluded that the novel combination of supplementation with an antimicrobial component, EPA/DHA containing fish oil, an antioxidant blend and a potent vitamin mineral supplement functioned interactively to favorably modify body weights, blood lipids and pro-inflammatory biomarkers better than diet, exercise and behavioral modification alone.

TABLE 22

Macronutrient composition of the study diet as total daily intake

| Composition | Total Daily Intake | | |
|---|---|---|---|
| | DIET | InForm1.1 | InForm1.2 |
| Calories (kcal) | 1510 | 1635 | 1715 |
| Fat (kcal) | 635 | 560 | 590 |
| Protein (g) | 159 | 172 | 173 |
| Available Carbohydrates (g) | 69 | 97 | 120 |
| Sugars (g) | 33 | 50 | 51 |
| Fiber | | | |
| Dietary (g) | 23 | 27 | 48 |
| Viscous (g) | 5.5 | 9.5 | 30 |
| Fat (g) | 70 | 62 | 65 |
| Saturated fatty acids (g) | 11.5 | 10.0 | 11.0 |
| Monounsaturated fatty acids (g) | 32.5 | 26.0 | 26.0 |
| Polyunsaturated fatty acids (g) | 12.5 | 12.5 | 12.5 |
| Trans fat | 1.0 | 1.0 | 1.0 |
| Dietary cholesterol (mg) | 770 | 660 | 660 |
| Alcohol (g) | — | — | — |

Thus, there have been disclosed a novel system for weight loss and its method of use. It will be readily apparent to those skilled in the art, however that various changes and modifications of an obvious nature may be made without departing from the spirit of the disclosed invention embodiments, and all such changes and modifications are considered to fall within the scope of the invention as recited herein, including in the appended claim.

What is claimed is:

1. A weight loss product that accelerates weight loss in a human subject eating a caloric restricted diet with a minimum daily protein intake of about 3 oz. and engaging in daily physical activity equivalent to about 5,000 steps per day, wherein the product comprises an effective amount of:
    an antimicrobial composition that includes berberine, cinnamon, curcumin, or a combination thereof;
    a fish oil composition;
    a probiotic composition that includes at least one of *Lactobacillus* spp., *Bifidobacterium* spp., *Bacillus* spp., and *Streptococcus* spp.;
    an antioxidant phytochemical composition that includes apple extract, grape extract, green tea extract, and olive extract; and
    a vitamin composition that includes vitamins A, B, C, D, and E;
    wherein the weight loss product stimulates weight loss of at least 3% more than if not administered to the human subject.

2. The product of claim 1, wherein the caloric restricted diet comprises a total daily caloric intake of from about 1,250 calories to about 1,500 calories.

3. The product of claim 1, wherein the antimicrobial composition comprises a daily dose ranging from about 300 mg to about 1,600 mg.

4. The product of claim 1, wherein the antimicrobial composition comprises berberine and the berberine comprises an extract from the Indian barberry root, *Berberis aristata*.

5. The product of claim 1, wherein the antimicrobial composition comprises berberine and the berberine comprises a daily dose of about 999 mg.

6. The product of claim 1, wherein the antimicrobial composition comprises cinnamon and the cinnamon is derived from the inner bark of one or more tree species from the genus *Cinnamomum*.

7. The product of claim 1, wherein the antimicrobial composition comprises cinnamon and the cinnamon comprises a daily dose ranging from about 250 mg to about 2,000 mg.

8. The product of claim 1, wherein the antimicrobial composition comprises cinnamon and the cinnamon comprises a daily of about 1,000 mg.

9. The product of claim 1, wherein the antimicrobial composition comprises curcumin and the curcumin comprises a daily dose ranging from about 1,500 mg to about 1,600 mg.

10. The product of claim 1, wherein the fish oil composition comprises a daily dose of about 1,000 mg to about 3,000 mg.

11. The product of claim 1, wherein the probiotic composition comprises either:
   Lactobacillus spp. and the Lactobacillus spp. are a member selected from the group consisting of L. rhamnosus, L. acidophilus, L. brevis, L. bulgaricus, L. plantarum, L. casei, L. salivarius, and combinations thereof; or
   Bifidobacterium spp. and the Bifidobacterium spp. are a member selected from the group consisting of B. bifidum, B. infantis, B. longum, and combinations thereof; or
   Bacillus spp. and the Bacillus spp. is Bacillus coagulans; or
   Streptococcus spp. and the Streptococcus spp. is Streptococcus thermophilus or;
   a combination thereof.

12. The product of claim 1, wherein the probiotic composition further comprises a member selected from the group consisting of inulin, fructooligosaccharide, prebiotic fibers, and combinations thereof.

13. The product of claim 1, wherein the probiotic composition comprises a daily dose of about 1 billion to about 50 billion colony forming units (cfu) of probiotic.

14. The product of claim 1, wherein the apple, grape, green tea, and olive extracts in the antioxidant phytochemical composition are present at a weight ratio of either about 1:1:1:1, or a weight ratio of about 6:1:3:1.

15. The product of claim 1, wherein the antioxidant phytochemical composition further comprises blueberry concentrate, capsicum extract, and turmeric extract.

16. The product of claim 1, wherein the antioxidant phytochemical composition further comprises mangosteen pericarp extract and bergamot extract.

17. The product of claim 1, wherein the antioxidant phytochemical composition is at a daily dose ranging from about 500 mg to about 1,000 mg.

18. The product of claim 1, wherein the vitamin composition comprises either B vitamins selected from the group consisting of Vitamin B1, B2, B6, B12, a D3 vitamin, or combinations thereof.

19. The product of claim 1, further comprising a member selected from the group consisting of: iron, docosahexaenoic acid (DHA), eicosapentaenoic acid (EPA), calcium, niacin, folic acid, biotin, panthothenic acid, phosphorus, iodine, magnesium, zinc, selenium, copper, manganese, chromium, potassium, inositol, p-Aminobenzoic acid (PABA), choline, bitartrate, lycopene, lutein, antioxidants, dandelion root, alfalfa aerial parts, asparagus stem, broccoli flowers, cabbage leaf, hesperidin bioflavonoid extract, lemon bioflavonoid extract, rutin, rose hips extract, chlorophyll, kelp leaf and stem, cranberry fruit, mangosteen fruit, carrot root, spinach leaf and stem, tomato fruit, acai berry, pomegranate fruit extract, L leucine, L lysine, L valine, L isoleucine, L phenylalanine, L threonine, L arginine, L-methionine, L tyrosine, L cysteine, and combinations thereof.

20. The product of claim 1, further comprising an amount of a phytosterol.

21. The product of claim 20, wherein the phytosterols comprise a daily dose of about 4 g.

22. The product of claim 1, wherein the antimicrobial composition, the fish oil composition, the probiotic composition, the antioxidant phytochemical composition and the vitamin composition are in oral formulations.

23. The product of claim 22, wherein the oral formulations are in the form of a liquid, capsule, powder, or a bar.

24. The system of claim 1, wherein the antimicrobial composition, fish oil, probiotic composition, antioxidant phytochemical composition, and vitamin composition are in a single formulation.

25. The product of claim 1, wherein the antimicrobial composition, fish oil composition, probiotic composition, antioxidant phytochemical composition, and vitamin composition are in a co-formulation.

26. The product of claim 1, wherein the product provides the human subject with an amount of weight loss that is greater than an amount attributable to the additive effect of eating the caloric restricted diet, engaging in the daily physical activity, and administering the weight loss system.

27. A method of facilitating weight loss in a human subject, comprising co-administering to the human subject:
   an effective amount of an antimicrobial composition that includes berberine, cinnamon, curcumin, or a combination thereof;
   an effective amount of fish oil composition;
   an effective amount of a probiotic composition that includes at least one of Lactobacillus spp., Bifidobacterium spp., Bacillus spp., and Streptococcus spp;
   an effective amount of an antioxidant phytochemical composition that includes apple extract, grape extract, green tea extract, and olive extract; and
   an effective amount of a vitamin composition that includes vitamins A, B, C, D, and E, wherein the method stimulates weight loss of at least 3% more than if not administered to the human subject.

28. The method of claim 27, wherein the antimicrobial composition is administered to the human subject at a daily dose ranging from about 300 mg to about 1,600 mg.

29. The method of claim 27, wherein the fish oil composition is administered to the human subject at a daily dose of about 1,000 mg to about 2,000 mg.

30. The method of claim 27, wherein the probiotic composition is administered to the human subject at a daily dose of about 1 billion to about 50 billion colony forming units (cfu).

31. The method of claim 27, wherein the antioxidant phytochemical composition is administered to the human subject at a daily dose ranging from about 500 mg to about 1,000 mg.

32. The method of claim 27, wherein the antimicrobial composition, the fish oil composition, the probiotic composition, the antioxidant phytochemical composition, and the vitamin composition are administered in a co-formulation.

33. The method of claim 27, further comprising administering a meal replacement formulation to the human subject.

34. The method of claim 33, wherein the meal replacement formulation that is administered to the human subject comprises from about 20 g. to about 60 g. protein, from about 3 g. to about 15 g. fat, from about 32 g. to about 96 g. carbohydrate, from about 2 g. to about 4 g. of phytosterols, and from about 180 to about 540 calories.

35. The method of claim 27, further comprising the human subject:
consuming a caloric restricted diet, engaging in moderate physical activity, and engaging in a cognitive behavioral program.

36. The method of claim 35, wherein the caloric restricted diet comprises a total daily caloric intake of from about 1,250 calories to about 1,500 calories.

37. The method of claim 35, wherein the moderate physical activity comprises the human subject taking at least 5,000 steps per day or the equivalent of 5,000 steps per day.

38. The method of claim 35, wherein the method provides the human subject with an amount of weight loss that is greater than an amount of weight loss attributable to the additive effect of eating the caloric restricted diet, engaging in the daily physical activity, engaging in the cognitive behavioral program, and co-administering the antimicrobial composition, fish oil composition, probiotic composition, antioxidant phytochemical composition, and vitamin composition.

\* \* \* \* \*